(12) United States Patent
Pfister et al.

(10) Patent No.: US 10,711,068 B2
(45) Date of Patent: Jul. 14, 2020

(54) ANTI-CD133 MONOCLONAL ANTIBODIES AND RELATED COMPOSITIONS AND METHODS

(71) Applicant: THE UNITED STATES OF AMERICA, AS REPRESENTED BY THE SECRETARY, DEPARTMENT OF HEALTH AND HUMAN SERVICES, Rockville, MD (US)

(72) Inventors: Thomas D. Pfister, Frederick, MD (US); Robert J. Kinders, Walkersville, MD (US); Tony Navas, Frederick, MD (US)

(73) Assignee: THE UNITED STATES OF AMERICA, AS REPRESENTED BY THE SECRETARY, DEPARTMENT OF HEALTH AND HUMAN SERVICES, Rockville, MD (US)

( * ) Notice: Subject to any disclaimer, the term of this patent is extended or adjusted under 35 U.S.C. 154(b) by 0 days.

(21) Appl. No.: 15/561,403

(22) PCT Filed: Mar. 28, 2016

(86) PCT No.: PCT/US2016/024531
§ 371 (c)(1),
(2) Date: Sep. 25, 2017

(87) PCT Pub. No.: WO2016/154623
PCT Pub. Date: Sep. 29, 2016

(65) Prior Publication Data
US 2018/0105598 A1 Apr. 19, 2018

Related U.S. Application Data

(60) Provisional application No. 62/138,825, filed on Mar. 26, 2015.

(51) Int. Cl.
*C07K 16/30* (2006.01)
*C07K 16/28* (2006.01)
*A61P 35/00* (2006.01)
*A61K 39/00* (2006.01)

(52) U.S. Cl.
CPC .......... *C07K 16/2896* (2013.01); *A61P 35/00* (2018.01); *A61K 2039/505* (2013.01); *C07K 2317/33* (2013.01); *C07K 2317/73* (2013.01)

(58) Field of Classification Search
None
See application file for complete search history.

(56) References Cited

U.S. PATENT DOCUMENTS

| 5,675,063 A | 10/1997 | Knight | |
|---|---|---|---|
| 2008/0254488 A1* | 10/2008 | De Maria | C12N 5/0695 435/7.23 |
| 2013/0067608 A1* | 3/2013 | Domon | G01N 33/57419 800/13 |
| 2013/0224202 A1* | 8/2013 | Ohlfest | C07K 16/2863 424/135.1 |

FOREIGN PATENT DOCUMENTS

| EP | 2175016 | 4/2010 | |
|---|---|---|---|
| EP | 2328923 | 6/2011 | |
| WO | 2011149493 | 12/2011 | |
| WO | WO2011149493 | * 12/2011 | |
| WO | WO-2011149493 A1 | * 12/2011 | ......... C07K 16/2863 |
| WO | 2013065017 | 5/2013 | |

OTHER PUBLICATIONS

Akunuru et al., "Non-small cell lung cancer stem/progenitor cells are enriched in multiple distinct phenotypic subpopulations and exhibit plasticity", Cell Death Dis. Jul. 19, 2012;3:e352. 10 pages.
Bertollini et al., "Highly tumorigenic lung cancer CD133+ cells display stem-like features and are spared by cisplatin treatment", vol. 106 No. 38 pp. 16281-16286, 2009, 6 pages.
Bidlingmaier et al., "The utility and limitations of glycosylated human CD133 epitopes in defining cancer stem cells", J Mol Med (Berl). Sep. 2008;86(9):1025-32. Epub Jun. 6, 2008, 15 pages.
Ernst et al., "A gene signature distinguishing CD133hi from CD133– colorectal cancer cells: essential role for EGR1 and downstream factors", Pathology.,vol. 43, No. 3, published on Apr. 1, 2011, pp. 220-227.
Karimi-Busheri et al., "CD24+/CD38– as new prognostic marker for non-small cell lung cancer", Multidiscip Respir Med. 2013; 8(1): 65. Published online Oct. 5, 2013. 9 pages.
Kemper et al., "The AC133 Epitope, but not the CD133 Protein, Is Lost upon Cancer Stem Cell Differentiation", Cancer Research, vol. 70, No. 2 published on Jan. 12, 2010, pp. 719-729.
Lai et al., "CD133+ Melanoma Subpopulations Contribute to Perivascular Niche Morphogenesis and Tumorigenicity through Vasculogenic Mimicry", Cancer Res. Oct. 1, 2012; 72(19):5111-8. Epub Aug. 3, 2012., 14 pages.
Miraglia et al., A Novel Five-Transmembrane Hematopoietic Stem Cell Antigen: Isolation, Characterization, and Molecular Cloning, Blood. Dec. 15, 1997;90(12):5013-21, 10 pages.
Osmond et al., "Glioblastoma cells negative for the anti-CD133 antibody AC133 express a truncated variant of the CD133 protein", Int J Mol Med. Jun. 2010 ;25(6):883-8.
International Patent Application No. PCT/US2016/024531 , "International Preliminary Report on Patentability", dated Oct. 5, 2017, 13 pages.

(Continued)

*Primary Examiner* — Lei Yao
(74) *Attorney, Agent, or Firm* — Kilpatrick Townsend & Stockton LLP

(57) ABSTRACT

Anti-CD133 monoclonal antibodies having advantageous properties; products, compositions and kits comprising the monoclonal antibodies; methods (processes) of making the monoclonal antibodies and related compositions, as well as methods of using the monoclonal antibodies in analytical, diagnostic and therapeutic applications.

13 Claims, 40 Drawing Sheets

Specification includes a Sequence Listing.

(56) References Cited

OTHER PUBLICATIONS

International Patent Application No. PCT/US2016/024531, "International Search Report and Written Opinion", dated Dec. 13, 2016, 22 pages.
International Patent Application No. PCT/US2016/024531, "Invitation to Pay Add'l Fees and Partial Search Report", dated Oct. 5, 2016, 8 pages.
Swaminathan et al., "Identification of a novel monoclonal antibody recognizing CD133", J Immunol Methods. Sep. 30, 2010;361(1-2):110-5. Epub Jul. 30, 2010.
Taieb et al., "The first extracellular domain of the tumour stem cell marker CD133 contains an antigenic ganglioside-binding motif", Cancer Letters, vol. 278, No. 2, published on Jun. 18, 2009, pp. 164-173.
Wang et al., "Two Novel Monoclonal Antibodies Against Human CD133-2: Distinct Epitopes and Agonist Activity to Enhance Growth of CD133 Expression Cells in Vitro", Hybridoma (Larchmt). Jun. 2010; 29(3):241-9.
Yin et al., "AC133, a Novel Marker for Human Hematopoietic Stem and Progenitor Cells", Blood. Dec. 15, 1997; 90(12):5002-12., 12 pages.

\* cited by examiner

FIGURE 2 A,B.

A. SEQ ID NO:1 aa

| | | | | | | |
|---|---|---|---|---|---|---|
| 1 | MALVLGSLLL | LGLCGNSFSG | GQPSSTDAPK | AWNYELPATN | YETQDSHKAG | PIGILFELVH |
| 61 | IFLYVVQPRD | FPEDTLRKFL | QKAYESKIDY | DKPETVILGL | KIVYYEAGII | LCCVLGLLFI |
| 121 | ILMPLVGYFF | CMCRCCNKCG | GEMHQRQKEN | GPFLRKCFAI | SLLVICIIIS | IGIFYGFVAN |
| 181 | HQVRTRIKRS | RKLADSNFKD | LRTLLNETPE | QIKYILAQYN | TTKDKAFTDL | NSINSVLGGG |
| 241 | ILDRLRPNII | PVLDEIKSMA | TAIKETKEAL | ENMNSTLKSL | HQQSTQLSSS | LTSVKTSLRS |
| 301 | SLNDPLCLVH | PSSETCNSIR | LSLSQLNSNP | ELRQLPPVDA | ELDNVNNVLR | TDLDGLVQQG |
| 361 | YQSLNDIPDR | VQRQTTTVVA | GIKRVLNSIG | SDIDNVTQRL | PIQDILSAFS | VYVNNTESYI |
| 421 | HRNLPTLEEY | DSYWWLGGLV | ICSLLTLIVI | FYYLGLLCGV | CGYDRHATPT | TRGCVSNTGG |
| 481 | VFLMVGVGLS | FLFCWILMII | VVLTFVFGAN | VEKLICEPYT | SKELFRVLDT | PYLLNEDWEY |
| 541 | YLSGKLFNKS | KMKLTFEQVY | SDCKKNRGTY | GTLHLQNSFN | ISEHLNINEH | TGSISSELES |
| 601 | LKVNLNIFLL | GAAGRKNLQD | FAACGIDRMN | YDSYLAQTGK | SPAGVNLLSF | AYDLEAKANS |
| 661 | LPPGNLRNSL | KRDAQTIKTI | HQQRVLPIEQ | SLSTLYQSVK | ILQRTGNGLL | ERVTRILASL |
| 721 | DFAQNFITNN | TSSVIIEETK | KYGRTIIGYF | EHYLQWIEFS | ISEKVASCKP | VATALDTAVD |
| 781 | VFLCSYIIDP | LNLFWFGIGK | ATVFLLPALI | FAVKLAKYYR | RMDSEDVYDD | VETIPMKNME |
| 841 | NGNNGYHKDH | VYGIHNPVMT | SPSQH | | | |

B. SEQ ID NO:2

MALVLGSLLLLGLCGNSFSGGQPSSTDAPKAWNYELPATKYETQDSHKAGPIGILFELVHIFLYVVQPRD
FPEDTLRKVIQKAYESKIDYDKIVYYEAGIILCCVLGLLFIILMPLVGYFFCMCRCCNKCGGEMHQRQKE
NGPFLRKCFAISLLVICIIISIGIFYGFVANHQVRTRIKRSRKLADSNFKDLRTLLNETPEQIKYILAQY
NTTKDKAFTDLNSISSVLGGGILDRLRPNIIPVLDEIKSMATAIKETKEALENMNSTLKSLHQQSTQLSS
SLTSVKTSLRSSLNDPLCLVRPSSETCNSIRLSLSQLNSNPELRQLPPVDAELDNVNNVLRTDLDGLVQQ
GYQSLNDIPDRVQRQTTTVVAGIKRVLNSIGSDIDNVTQRLPIQDILSEFSVYVNNTESYIHRNLPTLEE
YDSYWWLGGLVICSLLTLIVIFYYLGLLCGVCGYDRHATPTTRGCVSNTGGIFLMVGVGLSFLFCWILMI
IVVLTFVFGANVEKLICEPYTSKELFRVLDTPYLLNEDWEYYLSGKLFNKSKMKLTFEQVYSDCKKNRGT
YGTLHLQNSFNISERLNINEHTGSISSELESLKVNLNIFLLGAAGRKNLQDFAACGIDRMNYDSYLAQTG
KSPAGVNLLSFAYDLEAKANSLPPGNLRNSLKRDAQTIKTIHQQRVLPIEQSLSTLYQSVKILQRTGNGL
LERVTRILASLDFAQNFITNNTSSVIIEETKKYGRTIIGYFEHYLQWIEFSISEKVASCKPVATALDTAV
DVFLCSYIIDPLNLFWFGIGKATVFLLPALIFAVKLAKYYRRMDSEDVYDDVETIPMKNMENGNNGYHKD
HVYGIHNPVMTSPSQH

FIGURE 2 C, D, E.
C.     SEQ ID NO:3

MALVLGSLLLLGLCGNSFSGGQPSSTDAPKAWNYELPATNYETQDSHKAGPIGILFELVHIFLYVVQPRD
FPEDTLRKVIQKAYESKIDYDKPETVILGLKIVYYEAGIILCCVLGLLFIILMPLVGYFFCMCRCCNKCG
GEMHQRQKENGPFLRKCFAISLLVICIIISIGIFYGFVANHQVRTRIKRSRKLADSNFKDLRTLLNETPE
QIKYILAQYNTTKDKAFTDLNSINSVLGGGILDRLRPNIIPVLDEIKSMATAIKETKEALENMNSTLKSL
HQQSTQLSSSLTSVKTSLRSSLNDPLCLVRPSSEICNSIRLSLSQLNSNPELRQLPPVDAELDNVNNVLR
TDLDGLVQQGYQSLNDIPDRVQRQTTTVVAGIKRVLNSIGSDIDNVTQRLPIQDILSEFSVYVNNTESYI
HRNLPTLEEYDSYWWLGGLVICSLLTLIVIFYYLGLLCGVCGYDRHATPTTRGCVSNTGGVFLMVGVGLS
FLFCWILMIIVVLTFVFGANVEKLICEPYTSKELFQVLDTPYLLNEDWEYYLSGKLFNKSKMKLTFEQVY
SDCKKNRGTYGTLHLQNSFNISERLNINEHTGSISSELESLKVNLNIFLLGAAGRKNLQDFAACGIDRMN
YDSYLAQTGKSPAGVNLLSFAYDLEAKANSLPPGNLRNSLKRDAQTIKTIHQQRVLPIEQSLSTLYQSVK
ILQRTGNGLLERVTRILASLDFAQNFITNNTSSVIIEETKKYGRTIIGYFEHYLQWIEFSISEKVASCKP
VATALDTAVDVFLCSYIIDPLNLFWFGIGKATVFLLPALIFAVKLAKYYRRMDSEDVYDDVETIPMKNME
NGNNGYHKDHVYGIHNPVMTSPSQH

D.     SEQ ID NO:4

MALLLGFLLLLELCWDTSALGPLSSTKGSDGLEFELPATNYETKDSNQAGPISVLFQIVQVFLQVVQPHP
FPEDILRKILQKKFDFSTDYDKIIYYEIGIIICAVLGLLFVILMPLVGFCLGLCRCCNKCGGEMHQRQKK
NGAFLRKYFTVSLLVICIFISVGIIYGFVANHHLRTRIEKTRKLAESNLKDLRTLLIGTPAQINYVLSQY
ASTKEKAFSDLDNIKSLLGGGIHDQLRPKVIPVLDDIKAMAEAIKETREALLNVNNTLKELKMSTAQLNT
SLSDVKRNLEQSLNDPMCSVPPVATTCNNIRMSLGQLDDNTNLGQLPSLDKQIDNINNVLQTDLSSLVQK
GYKSFNDIPEMVQNQTTDIVSDVKRTLNSLGSDIENMSEQIPIQDKLSDFIGYINDTETYIHRNLPTLEE
YDSYRWLGGLIVCCLLTLIVVFYYLGLMCGTFGYDRHATPTRRGCVSNTGGIFLMVGVGISFLFCWILMT
IVVLTFVIGGNMEKLVCEPYQNRKLFQILDTPYLLNENWKYYLSGMVLNKPDINLTFEQVYSDCKENKGI
YSTLKLENTYNISEHLNIQEHARNLSNDFKNMNVNIDNIVLLDAAGRKNLMDFSSSGVDTIDYNVYLAEM
GKTPTKVNLLSFADDLDTKANNLPQGSLKQSLKNNVQNLKTIHHGQVMPLEQSMSTINQSIKELQHKSSG
LRVKVANILSSLDSAQDFLQTRISSVIVKESSKYGNMIIGYFEHYLQWVKISITEQIAACKPVATALDSA
VDVFLCSYIIDPMNLFWFGIGKATIFLLPAIIFAVKLAKYYRRMDSEDVYDDMENGNIGFHRHHSTQTV

E.     SEQ ID NO:5

MALVFSALLLLGLCGKISSEGQPAFHNTPGAMNYELPTTKYETQDTFNAGIVGPLYKMVHIFLNVVQPND
FPLDLIKKLIQNKNFDISVDSKEPEIIVLALKIALYEIGVLICAILGLLFIILMPLVGCFFCMCRCCNKC
GGEMHQRQKQNAPCRRKCLGLSLLVICLLMSLGIIYGFVANQQTRTRIKGTQKLAKSNFRDFQTLLTETP
KQIDYVVEQYTNTKNKAFSDLDGIGSVLGGRIKDQLKPKVTPVLEEIKAMATAIKQTKDALQNMSSSLKS
LQDAATQLNTNLSSVRNSIENSLSSSDCTSDPASKICDSIRPSLSSLGSSLNSSQLPSVDRELNTVTEVD
KTDLESLVKRGYTTIDEIPNTIQNQTVDVIKDVKNTLDSISSNIKDMSQSIPIEDMLLQVSHYLNNSNRY
LNQELPKLEEYDSYWWLGGLIVCFLLTLIVTFFFLGLLCGVFGYDKHATPTRRGCVSNTGGIFLMAGVGF
GFLFCWILMILVVLTFVVGANVEKLLCEPYENKKLLQVLDTPYLLKEQWQFYLSGMLFNNPDINMTFEQV
YRDCKRGRGIYAAFQLENVVNVSDHFNIDQISENINTELENLNVNIDSIELLDNTGRKSLEDFAHSGIDT
IDYSTYLKETEKSPTEVNLLTFASTLEAKANQLPEGKLKQAFLLDVQNIRAIHQHLLPPVQQSLKFVRVR
NTLRQSVWTLQQTSNKLPEKVKKILASLDSVQHFLTNNVSLIVIGETKKFGKTILGYFEHYLHWVFYAIT
EKMTSCKPMATAMDSAVNGILCGYVADPLNLFWFGIGKATVLLLPAVIIAIKLAKYYRRMDSEDVYDDPS
RY

FIGURE 2 F, G, H

F.       SEQ ID NO:6

MALVFSVLLLLGLCGKMASGGQPAFDNTPGALNYELPTTEYETQDTFNAGIIDPLYQMVHIFLNVVQPND
FPQDLVKKLIQKRFDISVDTKEVAIYEIGVLICVILGLLFIFLMPLVGFFFCMCRCCNKCGGEMHQRQKQ
NESCRRKCLAISLLLICLLMSLGIAFGFVANQQTRTRIQRTQKLAESNYRDLRALLTEAPKQIDYILGQY
NTTKNKAFSDLDSIDSVLGGRIKGQLKPKVTPVLEEIKAMATAIRQTKDALQNMSSSLKSLRDASTQLST
NLTSVRNSIENSLNSNDCASDPASKICDSLRPQLSNLGSNHNGSQLPSVDRELNTVNDVDRTDLESLVKR
GYMSIDEIPNMIQNQTGDVIKDVKKTLDSVSSKVKNMSQSIPVEEVLLQFSHYLNDSNRYIHESLPRVEE
YDSYWWLGGLIVCFLLTLIVTFFYLGLLCGVFGYDKRATPTRRGCVSNTGGIFLMAGVGFSFLFCWILMI
LVVLTFVVGANVEKLLCEPYENKKLLQVLDTPYLLNDQWQFYLSGILLKNPDINMTFEQVYRDCKRGRGV
YATFQLENVFNITENFNIERLSEDIVKELEKLNVNIDSIELLDKTGRKSLEDFAQSGIDRINYSMYLQEA
EKPPTKVDLLTFASFLETEANQLPDGNLKQAFLMDAQNIRAIHQQHVPPVQQSLNSLKQSVWALKQTSSK
LPEEVKKVLASLDSAQHFLTSNLSSIVIGETKKFGRTIIGYFEHYLQWVLYAITEKMTSCKPMITAMDSA
VNGILCSYVADPLNLFWFGIGKATMLLLPAVIIAIKLAKYYRRMDSEDVYDDVETVPMKNLENGSNGYHK
DHLYGVHNPVMTSPSRY

G.       SEQ ID NO:7

MALVLGSLLLLGLCGNSFSGGQPSSTDAPKAWNYELPATNYETQDSHKAGPIGILFELVHIFLYVVQPRD
FPEDTLRKFLQKAYESKIDYDKPETVILGLKIVYYEAGIILCCVLGLLFIILMPLVGYFFCMCRCCNKCG
GEMHQRQKENGPFLRKCFAISLLVICIIISIGIFYGFVANHQVRTRIKRSRKLADSNFKDLRTLLNETPE
QIKYILAQYNTTKDKAFTDLNSINSVLGGGILDRLRPNIIPVLDEIKSMATAIKETKEALENMNSTLKSL
HQQSTQLSSSLTSVKTSLRSSLNDPLCLVHPSSETCNSIRLSLSQLNSNPELRQLPPVDAELDNVNNVLR
TDLDGLVQQGYQSLNDIPDRVQRQTTTVVAGIKRVLNSIGSDIDNVTQRLPIQDILSAFSVYVNNTESYI
HRNLPTLEEYDSYWWLGGLVICSLLTLIVIFYYLGLLCGVCGYDRHATPTTRGCVSNTGGVFLMVGVGLS
FLFCWILMIIVVLTFVFGANVEKLICEPYTSKELFRVLDTPYLLNEDWEYYLSGKLFNKSKMKLTFEQVY
SDCKKNRGTYGTLHLQNSFNISEHLNINEHTGSISSELESLKVNLNIFLLGAAGRKNLQDFAACGIDRMN
YDSYLAQTGKSPAGVNLLSFAYDLEAKANSLPPGNLRNSLKRDAQTIKTIHQQRVLPIEQSLSTLYQSVK
ILQRTGNGLLERVTRILASLDFAQNFITNNTSSVIIEETKKYGRTIIGYFEHYLQWIEFSISEKVASCKP
VATALDTAVDVFLCSYIIDPLNLFWFGIGKATVFLLPALIFAVKLAKYYRRMDSEDVYDDSSWVTSVQVN
FFFLVLIFLYLF

H.       SEQ ID NO:8

MALLLGFLLLLELCWDTSALGPLSSTKGSDGLEFELPATNYETKDSNQAGPISVLFQIVQVFLQVVQPHP
FPEDILRKILQKKFDFSTDYDKPENVVLTLKIIYYEIGIIICAVLGLLFVILMPLVGFCFGLCRCCNKCG
GEMHQRQKKNGAFLRKYFTVSLLVICIFISVGIIYGFVANHHLRTRIEKTRKLAESNLKDLRTLLIGTPA
QINYVLSQYASTKEKAFSDLDNIKSLLGGGIHDQLRPKVIPVLDDIKAMAEAIKETREALLNVNNTLKEL
KMSTAQLNTSLSDVKRNLEQSLNDPMCSVPFVATTCNNIRMSLGQLDDNTNLGQLPSLDKQIDNINNVLQ
TDLSSLVQKGYKSFNDIPEMVQNQTTDIVSALPYVKRTLNSLGSDIENMSEQIPIQDKLSDFIGYINDTE
TYIHRNLPTLEEYDSYRWLGGLIVCCLLTLIVVFYYLGLMCGTFGYDRHATPTRRGCVSNTGGIFLMVGV
GISFLFCWILMTIVVLTFVIGGNMEKLVCEPYQNRKLFQILDTPYLLNENWKYYLSGMVLDKPDINLTFE
QVYSDCKENGIYSTLKLENTYNISEHLNIQEHARNLSNDFKNMNVNIDNIVLLDAAGRKNLMDFSSSGV
DTIDYNVYLAEMGKTPTKVNLLSFADDLDTKANNLPQGSLKQSLKNNAQNLKTIHHGQVMPLEQSMKYGK
ARSTINQSIKELQHKSSGLRVKVANILSSLDSAQDFLQTRISSVIVKESSKYGNMIIGYFEHYLQWVKIS
ITEQIAACKPVATALDSAVDVFLCSYIIDPMNLFWFGIGKATIFLLPAIIFAVKLAKYYRRMDSEDVYDD
SSVLGTWHFTL

FIGURE 3
A.
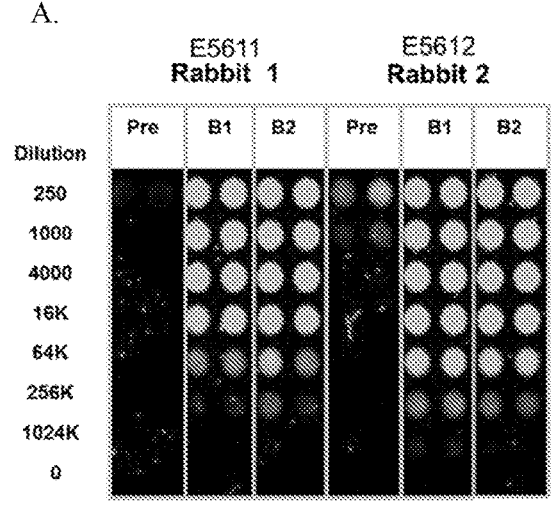
B.
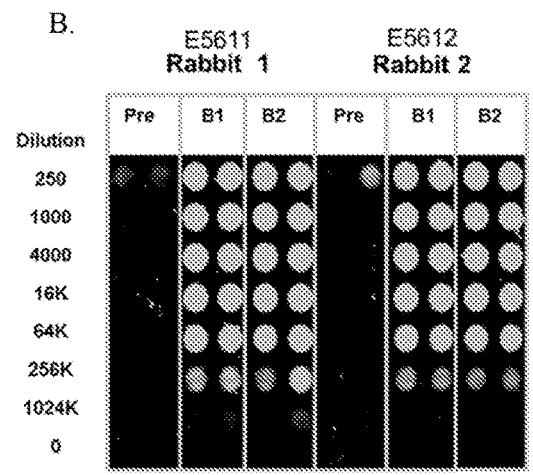

FIGURE 4.
A.
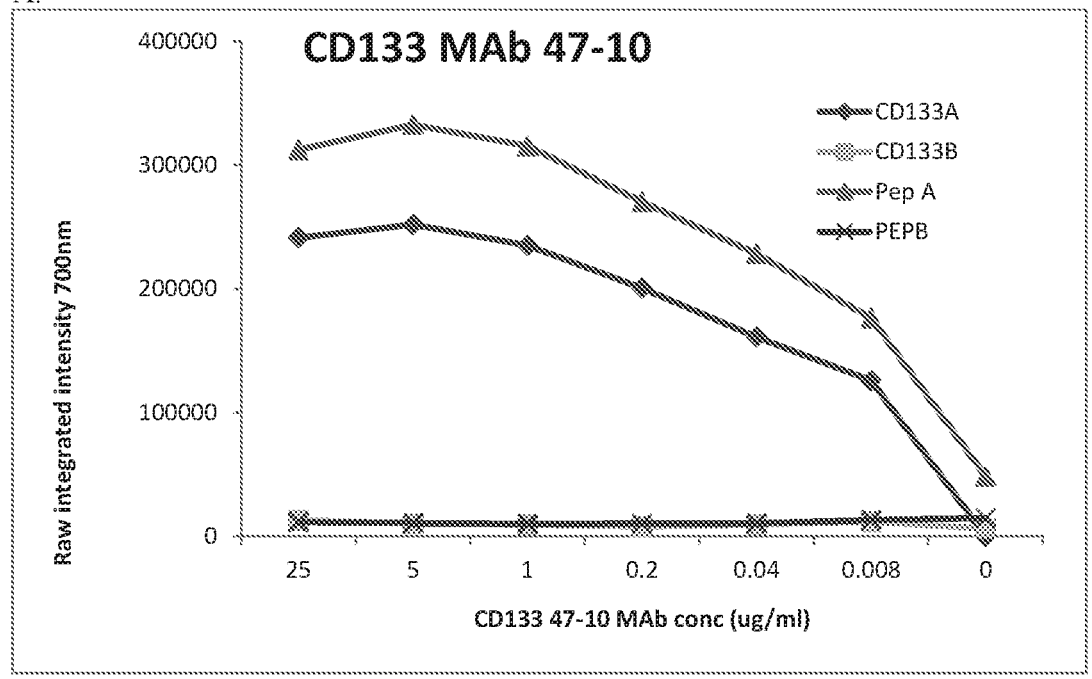
B.
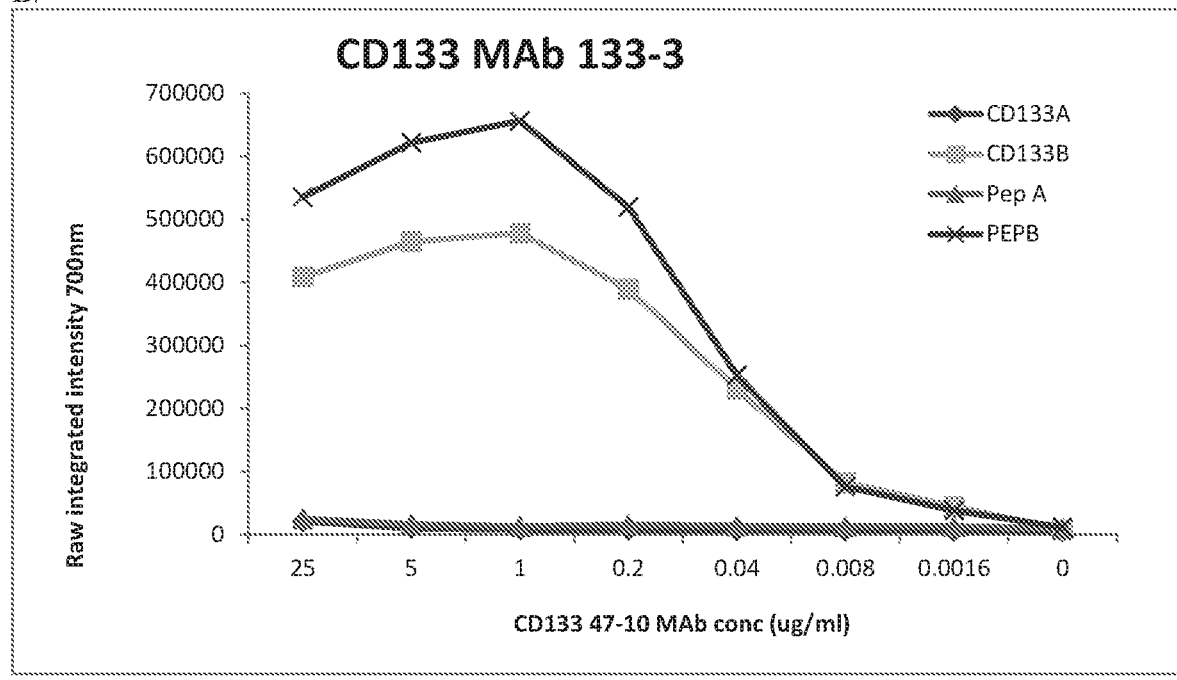

FIGURE 5

A. Heavy Chain

SEQ ID NO:9

```
M E T G L R W L L L V A V L K G V Q C Q S V E E S G G R L V T P
G T P L T L T C T V S G I D L N N Y N M Q W V R Q A P G K G L E
W I G A T F G S D S I Y Y A T W A K G R F T I S K T S T T V D L
K M T S L T T E D T A T Y F C A R G G L W G P G T L V T V S S G
Q P K A P S V F P L A P C C G D T P S S T V T L G C L V K G Y L
P E P V T V T W N S G T L T N G V R T F P S V R Q S S G L Y S L
S S V V S V T S S S Q P V T C N V A H P A T N K V D K T V A P
S T C S K P T C P P P E L L G G P S V F I F P P K P K D T L M I
S R T P E V T C V V V D V S Q D D P E V Q F T W Y I N N E Q V R
T A R P P L R E Q Q F N S T I R V V S T L P I A H Q D W L R G K
E F K C K V H N K A L P A P I E K T I S K A R G Q P L E P K V Y
T M G P P R E E L S S R S V S L T C M I N G F Y P S D I S V E W
E K N G K A E D N Y K T T P A V L D S D G S Y F L Y S K L S V P
T S E W Q R G D V F T C S V M H E A L H N H Y T Q K S I S R S P
G K
```

SEQ ID NO:10

```
ATGGAGACTGGGCTGCGCTGGCTTCTCCTGGTCGCTGTGCTCAAAGGTGTCCAGTGTCAGTCGG
TGGAGGAGTCCGGGGGTCGCCTGGTCACGCCTGGGACACCCCTGACACTCACCTGCACCGTCTC
TGGAATCGACCTCAATAACTATAACATGCAATGGGTCCGCCAGGCTCCAGGGAAGGGGCTGGAA
TGGATCGGGGCCACTTTTGGTAGTGATAGTATATACTACGCGACCTGGGCGAAAGGCCGATTCA
CCATCTCCAAAACCTCGACCACGGTGGATCTGAAAATGACCAGTCTGACAACCGAGGACACGGC
CACCTATTTCTGTGCCAGAGGTGGTCTCTGGGGCCCAGGCACCCTGGTCACCGTCTCCTCAGGG
CAACCTAAGGCTCCATCAGTCTTCCCACTGGCCCCCTGCTGCGGGGACACACCCAGCTCCACGG
TGACCCTGGGCTGCCTGGTCAAAGGGTACCTCCCGGAGCCAGTGACCGTGACCTGGAACTCGGG
CACCCTCACCAATGGGGTACGCACCTTCCCGTCCGTCCGGCAGTCCTCAGGCCTCTACTCGCTG
AGCAGCGTGGTGAGCGTGACCTCAAGCAGCCAGCCCGTCACCTGCAACGTGGCCCACCCAGCCA
CCAACACCAAAGTGGACAAGACCGTTGCGCCCTCGACATGCAGCAAGCCCACGTGCCCACCCCC
TGAACTCCTGGGGGGACCGTCTGTCTTCATCTTCCCCCCAAAACCCAAGGACACCCTCATGATC
TCACGCACCCCCGAGGTCACATGCGTGGTGGTGGACGTGAGCCAGGATGACCCCGAGGTGCAGT
TCACATGGTACATAAACAACGAGCAGGTGCGCACCGCCCGGCCGCCGCTACGGGAGCAGCAGTT
CAACAGCACGATCCGCGTGGTCAGCACCCTCCCCATCGCGCACCAGGACTGGCTGAGGGGCAAG
GAGTTCAAGTGCAAAGTCCACAACAAGGCACTCCCGGCCCCATCGAGAAACCATCTCCAAAG
CCAGAGGGCAGCCCCTGGAGCCGAAGGTCTACACCATGGGCCCTCCCCGGGAGGAGCTGAGCAG
CAGGTCGGTCAGCCTGACCTGCATGATCAACGGCTTCTACCCTTCCGACATCTCGGTGGAGTGG
GAGAAGAACGGGAAGGCAGAGGACAACTACAAGACCACGCCGGCCGTGCTGGACAGCGACGGCT
CCTACTTCCTCTACAGCAAGCTCTCAGTGCCCACGAGTGAGTGGCAGCGGGGCGACGTCTTCAC
CTGCTCCGTGATGCACGAGGCCTTGCACAACCACTACACGCAGAAGTCCATCTCCCGCTCTC
```

FIGURE 5

B. Light Chain

SEQ ID NO:11

M D T R A P T Q L L G L L L L W L P G V T F A Q V L T Q T A S P
V S A A V G A T V T I N C Q S S Q S V Y N N N Y L A W F Q Q K P
G Q P P K L L I Y R A S T L A S G V S S R F K G S G S G T Q F A
L T I S G V Q C D D A G T Y Y C Q G E F S C D S A D C A A F G G
G T E V V V K G D P V A P T V L I F P P A A D Q V A T G T V T I
V C V A N K Y F P D V T V T W E V D G T T Q T T G I E N S K T P
Q N S A D C T Y N L S S T L T L T S T Q Y N S H K E Y T C K V T
Q G T T S V V Q S F N R G D C

SEQ ID NO:12

ATGGACACGAGGGCCCCCACTCAGCTGCTGGGGCTCCTGCTGCTCTGGCTCCCAGGTGTCACAT
TTGCCCAAGTGCTGACCCAGACTGCATCGCCCGTGTCTGCAGCTGTGGGCGCCACCGTCACCAT
CAACTGCCAGTCCAGTCAGAGTGTTTATAATAACAACTACTTAGCCTGGTTTCAGCAGAAACCA
GGGCAGCCTCCCAAGCTCCTGATCTACAGGGCATCCACTCTGGCTTCTGGGGTCTCATCGCGGT
TCAAAGGCAGTGGATCTGGGACACAGTTCGCTCTCACCATCAGCGGCGTGCAGTGTGACGATGC
TGGCACTTACTATTGTCAAGGCGAATTTAGTTGTGATAGTGCTGATTGTGCTGCTTTCGGCGGA
GGGACCGAGGTGGTGGTCAAAGGTGATCCAGTTGCACCTACTGTCCTCATCTTCCCACCAGCTG
CTGATCAGGTGGCAACTGGAACAGTCACCATCGTGTGTGTGGCGAATAAATACTTTCCCGATGT
CACCGTCACCTGGGAGGTGGATGGCACCACCCAAACAACTGGCATCGAGAACAGTAAAACACCG
CAGAATTCTGCAGATTGTACCTACAACCTCAGCAGCACTCTGACACTGACCAGCACACAGTACA
ACAGCCACAAAGAGTACACCTGCAAGGTGACCCAGGGCACGACCTCAGTCGTCCAGAGCTTCAA
TAGGGGTGACTGT

FIGURE 6A.

Heavy Chain

SEQ ID NO:13

M E T G L R W L L L V A V L K G V Q C Q S V E E S G G R L V T P
G T P L T L T C T V S G F S L S R Y A M S W V R Q A P G K G L D
W I G Y I D I G G A Y Y A S W A K G R F T I S E T S T T V Y L
K V N S P T T E D T A T Y F C A R G V A N S D I W G P G T L V T
V S S G Q P K A P S V F P L A P C C G D T P S S T V T L G C L V
K G Y L P E P V T V T W N S G T L T N G V R T F P S V R Q S S G
L Y S L S S V V S V T S S Q P V T C N V A H P A T N T K V D K
T V A P S T C S K P T C P P P E L L G G P S V F I F P P K P K D
T L M I S R T P E V T C V V V D V S Q D D P E V Q F T W Y I N N
E Q V R T A R P P L R E Q Q F N S T I R V V S T L P I A H Q D W
L R G K E F K C K V H N K A L P A P I E K T I S K A R G Q P L E
P K V Y T M G P P R E E L S S R S V S L T C M I N G F Y P S D I
S V E W E K N G K A E D N Y K T T P A V L D S D G S Y F L Y S K
L S V P T S E W Q R G D V F T C S V M H E A L H N H Y T Q K S I
S R S P G K

SEQ ID NO:14

ATGGAGACTGGGCTGCGCTGGCTTCTCCTGGTCGCTGTGCTCAAAGGTGTCCAGTGTCAGTCGG
TGGAGGAGTCCGGGGGTCGCCTGGTCACGCCTGGGACACCCCTGACACTCACCTGCACAGTCTC
TGGATTCTCCCTCAGTAGGTATGCAATGAGCTGGGTCCGCCAGGCTCCAGGGAAGGGACTGGAC
TGGATCGGGTATATTGATATTGGTGGTGGCGCATACTACGCGAGCTGGGCGAAAGGTCGATTCA
CCATCTCCGAGACCTCGACCACGGTGTACCTGAAAGTCAACAGTCCGACAACCGAGGACACGGC
CACCTATTTCTGTGCCAGAGGTGTTGCTAATAGTGACATCTGGGGCCCAGGCACCCTGGTCACC
GTCTCCTCAGGGCAACCTAAGGCTCCATCAGTCTTCCCACTGGCCCCTGCTGCGGGGACACAC
CCAGCTCCACGGTGACCCTGGGCTGCCTGGTCAAAGGGTACCTCCCGGAGCCAGTGACCGTGAC
CTGGAACTCGGGCACCCTCACCAATGGGGTACGCACCTTCCCGTCCGTCCGGCAGTCCTCAGGC
CTCTACTCGCTGAGCAGCGTGGTGAGCGTGACCTCAAGCAGCCAGCCCGTCACCTGCAACGTGG
CCCACCCAGCCACCAACACCAAAGTGGACAAGACCGTTGCGCCCTCGACATGCAGCAAGCCCAC
GTGCCCACCCCCTGAACTCCTGGGGGGACCGTCTGTCTTCATCTTCCCCCCAAAACCCAAGGAC
ACCCTCATGATCTCACGCACCCCCGAGGTCACATGCGTGGTGGTGGACGTGAGCCAGGATGACC
CCGAGGTGCAGTTCACATGGTACATAAACAACGAGCAGGTGCGCACCGCCCGGCCGCCGCTACG
GGAGCAGCAGTTCAACAGCACGATCCGCGTGGTCAGCACCCTCCCCATCGCGCACCAGGACTGG
CTGAGGGGCAAGGAGTTCAAGTGCAAAGTCCACAACAAGGCACTCCCGGCCCCCATCGAGAAAA
CCATCTCCAAAGCCAGAGGGCAGCCCCTGGAGCCGAAGGTCTACACCATGGGCCCTCCCCGGGA
GGAGCTGAGCAGCAGGTCGGTCAGCCTGACCTGCATGATCAACGGCTTCTACCCTTCCGACATC
TCGGTGGAGTGGGAGAAGAACGGGAAGGCAGAGGACAACTACAAGACCACGCCGGCCGTGCTGG
ACAGCGACGGCTCCTACTTCCTCTACAGCAAGCTCTCAGTGCCCACGAGTGAGTGGCAGCGGGG
CGACGTCTTCACCTGCTCCGTGATGCACGAGGCCTTGCACAACCACTACACGCAGAAGTCCATC
TCCCGCTCTCCGGGTAAA

Figure 6B.

Light Chain

SEQ ID NO:15

```
M D T R A P T Q L L G L L L L W L P G A R C A L V M T Q T P S P
V S A A V G G T V T I N C Q S S Q S V F N N K W L S W Y Q Q K P
G Q P P K L L I Y F V S T L A S G V P S R F K G S G S G T Q F T
L T I S G V Q C D D A A T Y Y C Q G S D Y S S G W Y S P F G G G
T E V V V E G D P V A P T V L I F P P A A D Q V A T G T V T I V
C V A N K Y F P D V T V T W E V D G T T Q T T G I E N S K T P Q
N S A D C T Y N L S S T L T L T S T Q Y N S H K E Y T C K V T Q
G T T S V V Q S F N R G D C
```

SEQ ID NO:16

```
ATGGACACGAGGGCCCCCACTCAGCTGCTGGGGCTCCTGCTGCTCTGGCTCCCAGGTGCCAGAT
GTGCCCTTGTGATGACCCAGACTCCATCCCCGTGTCTGCAGCTGTGGGAGGCACAGTCACCAT
CAATTGCCAGTCCAGTCAGAGTGTTTTTAATAATAAATGGTTATCCTGGTATCAGCAGAAACCA
GGGCAGCCTCCCAAGCTCCTGATCTATTTTGTATCCACTCTGGCATCTGGGGTCCCATCGCGGT
TCAAAGGCAGTGGATCTGGGACACAGTTCACTCTCACCATCAGCGGCGTGCAGTGTGACGATGC
TGCCACTTACTACTGTCAAGGCAGTGATTATAGTAGTGGTTGGTATAGTCCTTTCGGCGGAGGG
ACCGAGGTGGTGGTCGAAGGTGATCCAGTTGCACCTACTGTCCTCATCTTCCCACCAGCTGCTG
ATCAGGTGGCAACTGGAACAGTCACCATCGTGTGTGTGGCGAATAAATACTTTCCCGATGTCAC
CGTCACCTGGGAGGTGGATGGCACCACCCAAACAACTGGCATCGAGAACAGTAAAACACCGCAG
AATTCTGCAGATTGTACCTACAACCTCAGCAGCACTCTGACACTGACCAGCACACAGTACAACA
GCCACAAAGAGTACACCTGCAAGGTGACCCAGGGCACGACCTCAGTCGTCCAGAGCTTCAATAG
GGGTGACTGT
```

| Query protein sequence | C | Q | S | V | E | E | S | G | G | R | L | V | T | P | G | T | P | L | T | L |
|---|---|---|---|---|---|---|---|---|---|---|---|---|---|---|---|---|---|---|---|---|
| Kabat numbering | H1 | H2 | H3 | H4 | H5 | H6 | H7 | H8 | H9 | H10 | H11 | H12 | H13 | H14 | H15 | H16 | H17 | H18 | H19 | H20 |

REGIONS: CHOTHIA — HFR1
ABM — HFR1
KABAT — HFR1
CONTACT — HFR1

| T | C | T | V | S | G | I | D | L | N | N | Y | N | M | Q | W | V | R | Q | A | P | G | K |
|---|---|---|---|---|---|---|---|---|---|---|---|---|---|---|---|---|---|---|---|---|---|---|
| H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |

CDR-H1 / HFR2 (Chothia)
CDR-H1 / HFR2 (ABM)
CDR-H1 / HFR2 (Kabat)
CDR-H1 / HFR2 (Contact)

| G | L | E | W | I | G | A | T | F | G | S | D | S | I | Y | Y | A | T | W | A | K | G | R |
|---|---|---|---|---|---|---|---|---|---|---|---|---|---|---|---|---|---|---|---|---|---|---|
| H44 | H45 | H46 | H47 | H48 | H49 | H50 | H51 | H52 | H53 | H54 | H55 | H56 | H57 | H58 | H59 | H60 | H61 | H62 | H63 | H64 | H65 | H66 |

CDR-H2 / HFR3 (Chothia)
CDR-H2 / HFR3 (ABM)
CDR-H2 / HFR3 (Kabat)
CDR-H2 / HFR3 (Contact)

| F | T | I | S | K | T | S | T | T | V | D | L | K | M | T | S | L | T | T | E | D | T | A |
|---|---|---|---|---|---|---|---|---|---|---|---|---|---|---|---|---|---|---|---|---|---|---|
| H67 | H68 | H69 | H70 | H71 | H72 | H73 | H74 | H75 | H76 | H77 | H78 | H79 | H80 | H81 | H82 | H82A | H83 | H84 | H85 | H86 | H87 | H88 |

| T | Y | F | C | A | R | G | G | L | W | G | P | G | T | L | V | T | V | S | S |
|---|---|---|---|---|---|---|---|---|---|---|---|---|---|---|---|---|---|---|---|
| H89 | H90 | H91 | H92 | H93 | H94 | H95 | H101 | H102 | H103 | H104 | H105 | H106 | H107 | H108 | H109 | H110 | H111 | H112 | H113 |

CDR-H3 / HFR4 (Chothia)
CDR-H3 / HFR4 (ABM)
CDR-H3 / HFR4 (Kabat)
CDR-H3 / HFR4 (Contact)

FIGURE 7

| Query protein sequence | A | Q | V | L | T | Q | T | A | S | P | V | S | A | A | V | G | A | T | V | T |
|---|---|---|---|---|---|---|---|---|---|---|---|---|---|---|---|---|---|---|---|---|
| Kabat numbering | L1 | L2 | L3 | L4 | L5 | L6 | L7 | L8 | L9 | L10 | L11 | L12 | L13 | L14 | L15 | L16 | L17 | L18 | L19 | L20 |

REGIONS: CHOTHIA — LFR1
ABM — LFR1
KABAT — LFR1
CONTACT — LFR1

| I | N | C | Q | S | S | Q | S | V | Y | N | N | N | Y | L | A | W | F | Q | Q | K | P | G |
|---|---|---|---|---|---|---|---|---|---|---|---|---|---|---|---|---|---|---|---|---|---|---|
| L21 | L22 | L23 | L24 | L25 | L26 | L27 | L27A | L27B | L28 | L29 | L30 | L31 | L32 | L33 | L34 | L35 | L36 | L37 | L38 | L39 | L40 | L41 |

CDR-L1 — LFR2
CDR-L1 — LFR2
CDR-L1 — LFR2
CDR-L1 — LFR2

| Q | P | P | K | L | L | I | Y | R | A | S | T | L | A | S | G | V | S | S | R | F | K | G |
|---|---|---|---|---|---|---|---|---|---|---|---|---|---|---|---|---|---|---|---|---|---|---|
| L42 | L43 | L44 | L45 | L46 | L47 | L48 | L49 | L50 | L51 | L52 | L53 | L54 | L55 | L56 | L57 | L58 | L59 | L60 | L61 | L62 | L63 | L64 |

CDR-L2 — LFR3
CDR-L2 — LFR3
CDR-L2 — LFR3
CDR-L2 — LFR3

| S | G | S | G | T | Q | F | A | L | T | I | S | G | V | Q | C | D | D | A | G | T | Y | Y |
|---|---|---|---|---|---|---|---|---|---|---|---|---|---|---|---|---|---|---|---|---|---|---|
| L65 | L66 | L67 | L68 | L69 | L70 | L71 | L72 | L73 | L74 | L75 | L76 | L77 | L78 | L79 | L80 | L81 | L82 | L83 | L84 | L85 | L86 | L87 |

| C | Q | G | E | F | S | C | D | S | A | D | C | A | A | F | G | G | G | T | E | V | V | V |
|---|---|---|---|---|---|---|---|---|---|---|---|---|---|---|---|---|---|---|---|---|---|---|
| L88 | L89 | L90 | L91 | L92 | L93 | L94 | L95 | L95A | L95B | L95C | L95D | L96 | L97 | L98 | L99 | L100 | L101 | L102 | L103 | L104 | L105 | L106 |

CDR-L3 — LFR4
CDR-L3 — LFR4
CDR-L3 — LFR4
CDR-L3 — LFR4

| K | G | D | P |
|---|---|---|---|
| L107 | L108 | L109 | L110 |

FIGURE 13.
A.
B.
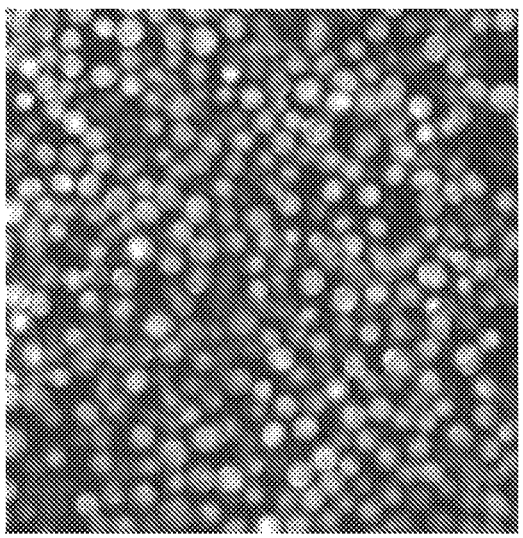
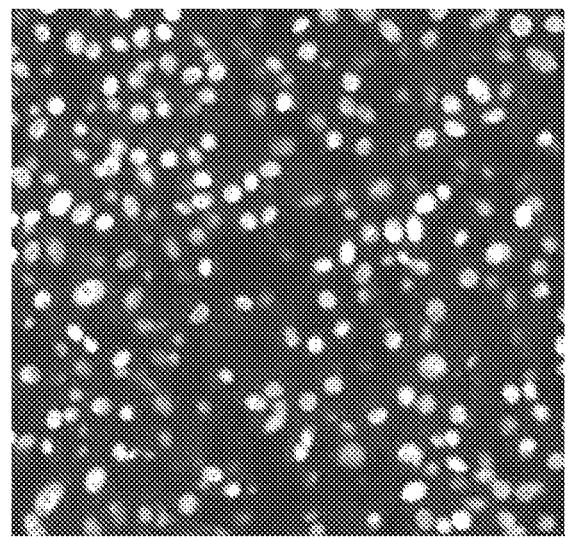

FIGURE 14.
A.
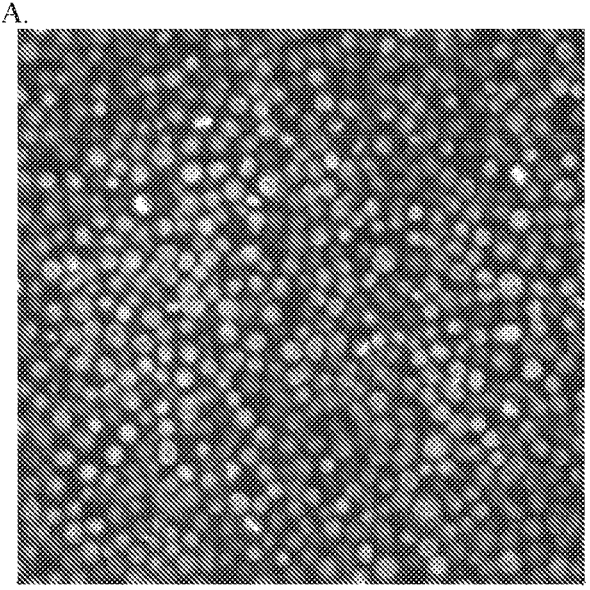
B.
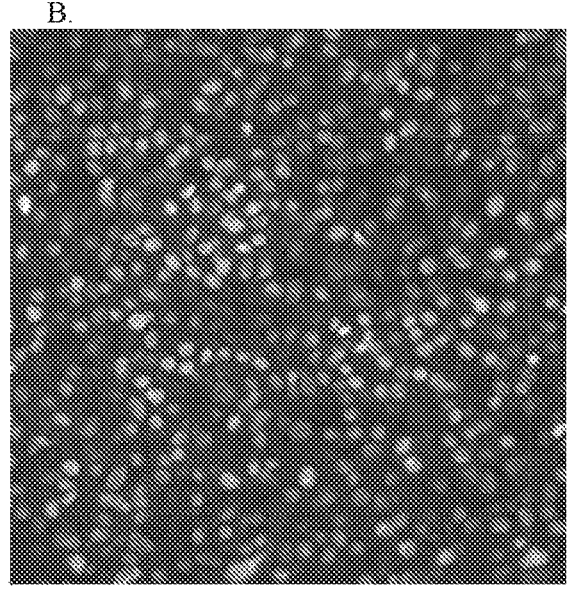

FIGURE 15.
A.
B.
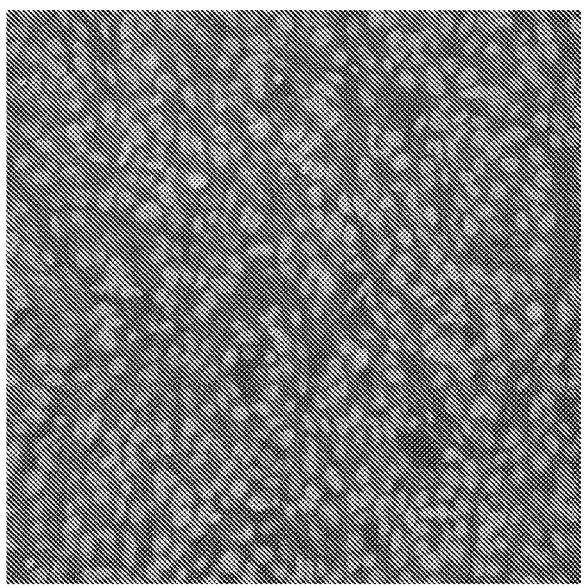
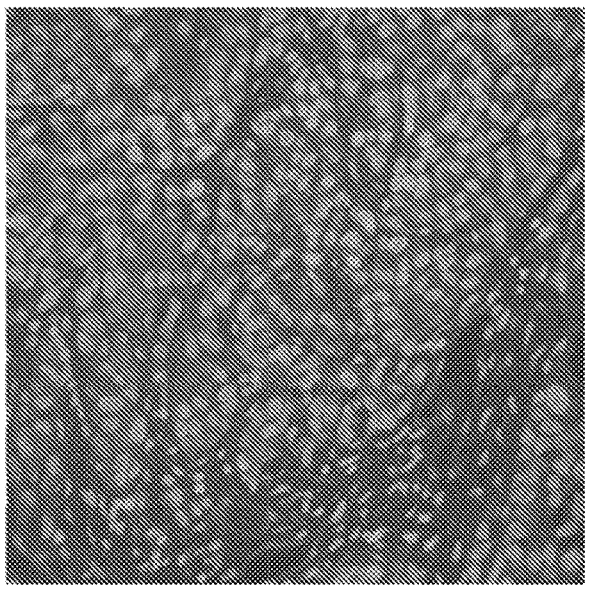

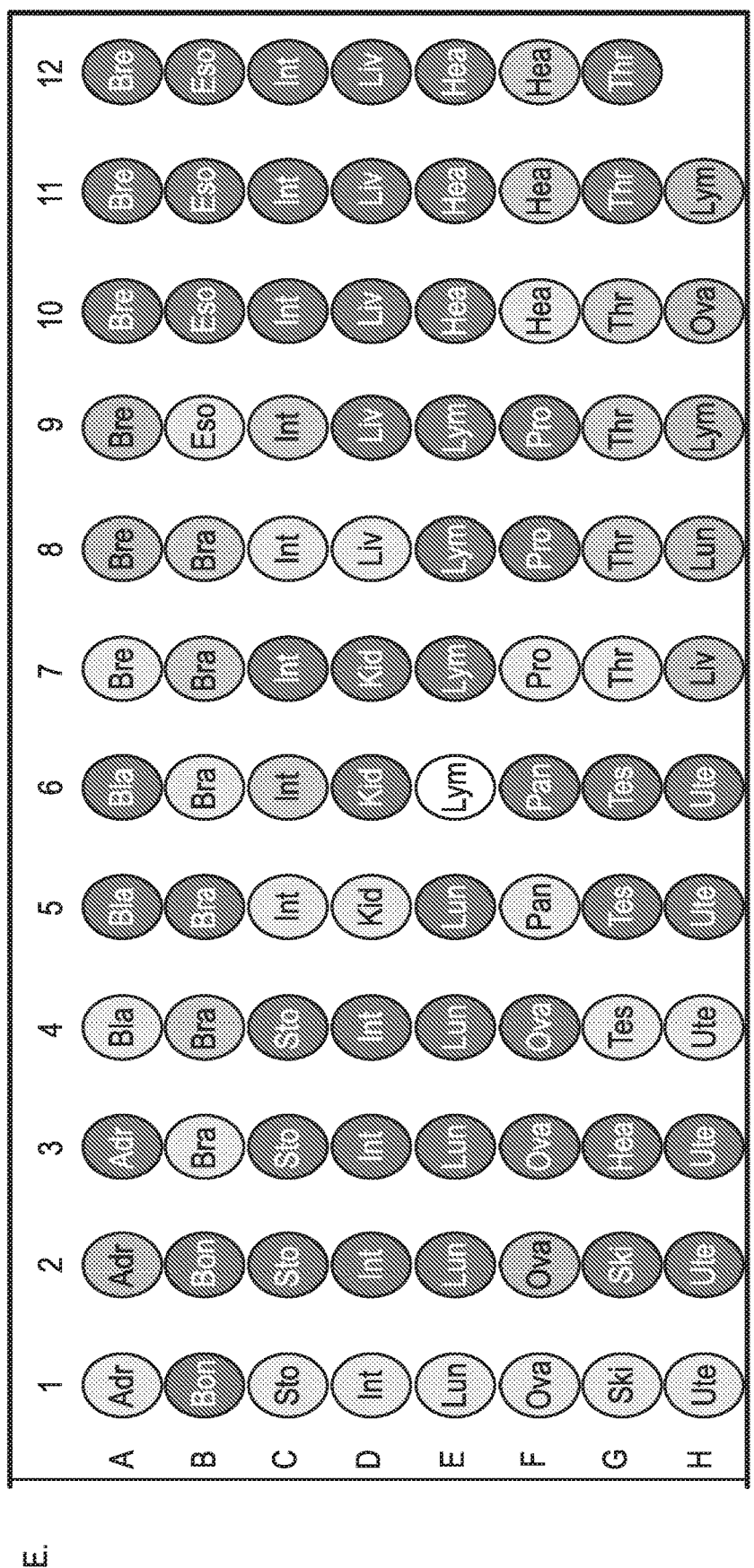

FIGURE 19

Legend: Adr-Arenal gland, Bla - Bladder, urinary, Bon - Bone, scapula, Bra - Brain, Bre - Breast, Eso - Esophagus, Hea - Head and neck, nasal cavity, Int - Intestine, rectum, Kid - Kidney, Liv - Liver, Lun - Lung, Lym - Lymph node, Ova - Ovary, Pan - Pancreas, Pro - Prostate, Ski - Skin, trunk, Sto - Stomach, Tes - Testis, Thr - Thyroid, Ute - Uterus, endometrium
◯ - Benign tumor, ◯ - , ● - Malignant tumor, ◯ - Mestasis, ◯ - Normal tissue

FIGURE 20A.

| position | sex | age | organ | pathology | grade | tnm | type |
|---|---|---|---|---|---|---|---|
| A1 | F | 37 | Adrenal gland | Normal, hyperplasia | | | Normal |
| A2 | M | 61 | Adrenal gland | Adenoma, cortical | | | Benign |
| A3 | M | 28 | Adrenal gland | Adrenocortical carcinoma | | T2N0M0 | Malignant |
| A4 | M | 53 | Bladder, urinary | Normal | | | Normal |
| A5 | F | 53 | Bladder, urinary | Transitional cell carcinoma | I~II | T1N0M0 | Malignant |
| A6 | F | 65 | Bladder, urinary | Transitional cell carcinoma | I~II | T1N0M0 | Malignant |
| A7 | F | 30 | Breast | Normal | | | Normal |
| A8 | F | 40 | Breast | Fibroadenoma | | | Benign |
| A9 | F | 39 | Breast | Fibroadenoma | | | Benign |
| A10 | F | 58 | Breast | Invasive ductal carcinoma | II | T2N1M0 | Malignant |
| A11 | F | 53 | Breast | Invasive ductal carcinoma | II | T2N0M0 | Malignant |
| A12 | F | 42 | Breast | Invasive ductal carcinoma | II | T4N1M0 | Malignant |
| B1 | M | 17 | Bone, tibia | Osteosarcoma | | | Malignant |
| B2 | M | 44 | Bone, scapula | Chondrosarcoma | | | Malignant |
| B3 | M | 49 | Brain, cerebellum | Normal* | | | Normal |
| B4 | F | 65 | Brain, cerebellum | Meningioma, fibroblastic | | | Benign |
| B5 | M | 55 | Brain, cerebellum | Malignant meningioma | | | Malignant |
| B6 | M | 58 | Brain | Normal* | | | Normal |
| B7 | F | 26 | Brain | Meningioma, fibroblastic | | | Benign |
| B8 | M | 47 | Brain | Astrocytoma | II | | Benign |
| B9 | M | 53 | Esophagus | Normal | | | Normal |
| B10 | F | 68 | Esophagus | Squamous cell carcinoma | I | T2N0M0 | Malignant |
| B11 | M | 54 | Esophagus | Squamous cell carcinoma | II | T3N1M0 | Malignant |
| B12 | F | 61 | Esophagus | Squamous cell carcinoma | III | T2N1M0 | Malignant |
| C1 | M | 59 | Stomach | Normal | | | Normal |
| C2 | M | 52 | Stomach | Adenocarcinoma | I | T2N0M0 | Malignant |
| C3 | M | 66 | Stomach | Adenocarcinoma | II | T3N0M0 | Malignant |
| C4 | M | 47 | Stomach | Adenocarcinoma | III | T3N2M0 | Malignant |
| C5 | F | 40 | Intestine, small intestine | Normal | | | Normal |
| C6 | F | 18 | Intestine, small intestine | Adenoma | | | Benign |
| C7 | F | 57 | Intestine, small intestine | Adenocarcinoma | II | T2N0M0 | Malignant |
| C8 | F | 27 | Intestine, colon | Normal | | | Normal |
| C9 | M | 57 | Intestine, colon | Adenoma | | | Benign |
| C10 | M | 56 | Intestine, colon | Adenocarcinoma | I | T3N0M0 | Malignant |
| C11 | M | 89 | Intestine, colon | Adenocarcinoma | II | T2N0M0 | Malignant |
| C12 | F | 43 | Intestine, colon | Adenocarcinoma | III | T3N0M0 | Malignant |
| D1 | M | 61 | Intestine, rectum | Normal | | | Normal |
| D2 | M | 40 | Intestine, rectum | Adenocarcinoma | I | T3N0M0 | Malignant |

FIGURE 20B.

| | | | | | | | |
|---|---|---|---|---|---|---|---|
| D3 | M | 38 | Intestine, rectum | Adenocarcinoma | II | T3N1M0 | Malignant |
| D4 | M | 50 | Intestine, rectum | Adenocarcinoma | III | T3N1M0 | Malignant |
| D5 | F | 51 | Kidney | Normal cortex | | | Normal |
| D6 | M | 40 | Kidney | Clear cell carcinoma | | T1N0M0 | Malignant |
| D7 | F | 79 | Kidney | Clear cell carcinoma | | T1N0M0 | Malignant |
| D8 | M | 43 | Liver | Normal | | | Normal |
| D9 | M | 26 | Liver | Hepatocellular carcinoma | I | T2N0M0 | Malignant |
| D10 | M | 40 | Liver | Hepatocellular carcinoma | II | T2N0M0 | Malignant |
| D11 | M | 53 | Liver | Hepatocellular carcinoma | I | T2N0M0 | Malignant |
| D12 | M | 41 | Liver | Hepatocellular carcinoma | III | T2N0M0 | Malignant |
| E1 | M | 58 | Lung | Normal | | | Normal |
| E2 | M | 59 | Lung | Squamous cell carcinoma | II | T2N2M0 | Malignant |
| E3 | M | 62 | Lung | Squamous cell carcinoma | II~III | T2N0M0 | Malignant |
| E4 | M | 72 | Lung | Adenocarcinoma | III | T2N2M0 | Malignant |
| E5 | M | 19 | Lung | Small cell carcinoma | | T3N0M0 | Malignant |
| E6 | F | 39 | Lymph node | Reactive | | | Inflammatory |
| E7 | M | 50 | Lymph node, neck | Lymphoma, Hodgkin lymphoma | | | Malignant |
| E8 | M | 42 | Lymph node, axillary | Lymphoma, non-Hodgkin B-cell lymphoma | | | Malignant |
| E9 | M | 51 | Lymph node, neck | Lymphoma, anaplastic large cell lymphoma | | | Malignant |
| E10 | F | 48 | Head and neck, oral cavity, hard palate | Adenocarcinoma | III~IV | | Malignant |
| E11 | M | 56 | Head and neck, oral cavity, tongue | Squamous cell carcinoma | II | T2N0M0 | Malignant |
| E12 | F | 48 | Head and neck, nasopharynx | Nasopharyngeal carcinoma, NPC | III | T2N0M0 | Malignant |
| F1 | F | 45 | Ovary | Normal | | | Normal |
| F2 | F | 55 | Ovary | Granulosa cell tumor | | | Benign |
| F3 | F | 45 | Ovary | Adenocarcinoma | III | T2N0M0 | Malignant |
| F4 | F | 49 | Ovary | Endometrioid adenocarcinoma | III | T1N0M0 | Malignant |
| F5 | M | 35 | Pancreas | Normal | | | Normal |
| F6 | F | 49 | Pancreas | Adenocarcinoma | II | T3N1M1 | Malignant |
| F7 | M | 65 | Prostate | Normal, hyperplasia | | | Normal |
| F8 | M | 60 | Prostate | Adenocarcinoma | II | T2N0M0 | Malignant |
| F9 | M | 47 | Prostate | Adenocarcinoma | III | T3N0M0 | Malignant |
| F10 | M | 38 | Head and neck, salivary gland | Normal | | | Normal |
| F11 | F | 28 | Head and neck, salivary gland, parotid | Pleomorphic adenoma | | | Benign |
| F12 | F | 38 | Head and neck, salivary gland | Adenoid cystic carcinoma | I~II | T1N0M0 | Malignant |
| G1 | M | 50 | Skin | Normal | | | Normal |

FIGURE 20C.

| | | | | | | | |
|---|---|---|---|---|---|---|---|
| G2 | M | 67 | Skin, trunk | Squamous cell carcinoma | II | T2N0M0 | Malignant |
| G3 | M | 53 | Head and neck, nasal cavity | Melanoma | | | Malignant |
| G4 | M | 77 | Testis | Normal | | | Normal |
| G5 | M | 30 | Testis | Seminoma | | | Malignant |
| G6 | M | 28 | Testis | Seminoma | | | Malignant |
| G7 | F | 62 | Thyroid | Normal | | | Normal |
| G8 | F | 47 | Thyroid | Adenoma | | | Benign |
| G9 | F | 27 | Thyroid | Adenoma | | | Benign |
| G10 | F | 66 | Thyroid | Adenoma | | | Benign |
| G11 | M | 16 | Thyroid | Follicular carcinoma | | T3N1M0 | Malignant |
| G12 | M | 34 | Thyroid | Follicular papillary adenocarcinoma | | T2N1M0 | Malignant |
| H1 | F | 41 | Uterus, cervix | Normal | | | Normal |
| H2 | F | 63 | Uterus, cervix | Squamous cell carcinoma | III | T1N0M0 | Malignant |
| H3 | F | 57 | Uterus, cervix | Squamous cell carcinoma | III | T1N1M0 | Malignant |
| H4 | F | 50 | Uterus, endometrium | Normal | | | Normal |
| H5 | F | 48 | Uterus, endometrium | Adenocarcinoma | I~II | T2N0M0 | Malignant |
| H6 | F | 53 | Uterus, endometrium | Adenocarcinoma | II~III | T1N1M0 | Malignant |
| H7 | M | 60 | Liver | Metastatic colon adenocarcinoma | | | Metastasis |
| H8 | M | 69 | Lung | Metastatic cancers, from gastrointestinal site? | | | Metastasis |
| H9 | F | 34 | Lymph node | Metastatic breast invasive ductal carcinoma | | | Metastasis |
| H10 | F | 40 | Ovary | Metastatic colon signet ring cell carcinoma | | | Metastasis |
| H11 | M | 51 | Lymph node | Metastatic esophagus squamous cell carcinoma | | | Metastasis |

Legend: Eso - Esophagus, Int - Intestine, Lym - Lymph node, Ora - Oral cavity, Rec - Rectum, Ski - Skin, Sto - Stomach, Vul - Vulva
◯ - Benign tumor, ● - Malignant tumor, ◯ - Malignant tumor (stage I), ◯ - Malignant tumor (stage IB), ◯ - Malignant tumor (stage II),
◯ - Malignant tumor (stage III), ◯ - Malignant tumor (stage IV), ● - Metastasis

FIGURE 24A.

| position | sex | age | organ | pathology | stage | tnm | type |
|---|---|---|---|---|---|---|---|
| A1 | M | 71 | Skin | Malignant melanoma of right rump | II | T4N0M0 | Malignant |
| A2 | M | 60 | Skin | Malignant melanoma of right rump | III | T4N1M0 | Malignant |
| A3 | M | 72 | Skin | Malignant melanoma of left sole | IB | T2aN0M0 | Malignant |
| A4 | M | 61 | Skin | Malignant melanoma of left armpit | IV | T4bN0M1 | Malignant |
| A5 | M | 55 | Skin | Malignant melanoma of left sole | II | T4N0M0 | Malignant |
| A6 | M | 51 | Skin | Malignant melanoma of back | II | T4N0M0 | Malignant |
| A7 | M | 25 | Skin | Malignant melanoma of left sole | I | T2N0M0 | Malignant |
| A8 | F | 46 | Skin | Malignant melanoma of thigh | II | T4N0M0 | Malignant |
| A9 | F | 32 | Skin | Malignant melanoma of right lumbar part (fibrofatty tissue) | II | T4N0M0 | Malignant |
| A10 | M | 80 | Skin | Malignant melanoma of right sole | II | T4N0M0 | Malignant |
| B1 | F | 42 | Skin | Malignant melanoma of right thigh | II | T4N0M0 | Malignant |
| B2 | M | 50 | Skin | Malignant melanoma of left shoulder (fibrous tissue and blood vessel) | II | T4N0M0 | Malignant |
| B3 | M | 41 | Skin | Malignant melanoma of left leg | II | T3N0M0 | Malignant |
| B4 | M | 37 | Skin | Malignant melanoma of right upper arm | II | T4N0M0 | Malignant |
| B5 | M | 61 | Skin | Malignant melanoma of right groin | III | T4N2M0 | Malignant |
| B6 | M | 52 | Skin | Malignant melanoma of left abdominal wall | II | T4N0M0 | Malignant |
| B7 | F | 59 | Skin | Malignant melanoma of right rump | I | T1N0M0 | Malignant |
| B8 | M | 79 | Skin | Malignant melanoma of left face | I | T1N0M0 | Malignant |
| B9 | M | 40 | Skin | Malignant melanoma of right chest wall | II | T4N0M0 | Malignant |
| B10 | F | 59 | Skin | Malignant melanoma with necrosis of anus | II | T4N0M0 | Malignant |
| C1 | M | 42 | Skin | Malignant melanoma of left heel | IV | T3N2M1 | Malignant |
| C2 | M | 41 | Skin | Malignant melanoma of left forearm | II | T4N0M0 | Malignant |
| C3 | M | 49 | Skin | Malignant melanoma of left arm | II | T4N0M0 | Malignant |
| C4 | M | 71 | Skin | Malignant melanoma of right groin | II | T4N0M0 | Malignant |
| C5 | F | 83 | Skin | Malignant melanoma of right little finger | I | T2N0M0 | Malignant |
| C6 | M | 51 | Skin | Malignant melanoma of left upper arm | III | T4N1M0 | Malignant |
| C7 | F | 41 | Skin | Malignant melanoma of scalp | II | T4N0M0 | Malignant |
| C8 | M | 51 | Skin | Malignant melanoma of left armpit | II | T4N0M0 | Malignant |
| C9 | M | 56 | Skin | Malignant melanoma of abdominal wall | II | T4N0M0 | Malignant |
| C10 | M | 66 | Skin | Malignant melanoma of right thigh | II | T4N0M0 | Malignant |
| D1 | M | 65 | Skin | Malignant melanoma of scalp | II | T4N0M0 | Malignant |
| D2 | M | 45 | Skin | Malignant melanoma of crissum | II | T4N0M0 | Malignant |
| D3 | M | 31 | Skin | Malignant melanoma of scalp | II | T4N0M0 | Malignant |
| D4 | F | 72 | Skin | Malignant melanoma of right cheek | II | T4N0M0 | Malignant |
| D5 | F | 46 | Skin | Malignant melanoma of right thumb | II | T4N0M0 | Malignant |
| D6 | F | 47 | Skin | Malignant melanoma of left upper arm | II | T4N0M0 | Malignant |
| D7 | M | 49 | Skin | Malignant melanoma of left foot | III | T4N1M0 | Malignant |

FIGURE 24B.

| | | | | | | | |
|---|---|---|---|---|---|---|---|
| D8 | F | 45 | Skin | Malignant melanoma of left thigh | I | T2N0M0 | Malignant |
| D9 | F | 72 | Vulva | Malignant melanoma | I | - | Malignant |
| D10 | F | 57 | Vulva | Malignant melanoma | I | - | Malignant |
| E1 | F | 38 | Vulva | Malignant melanoma | I | - | Malignant |
| E2 | F | 44 | Vulva | Malignant melanoma | I | - | Malignant |
| E3 | F | 62 | Vulva | Malignant melanoma | I | - | Malignant |
| E4 | F | 45 | Vulva | Malignant melanoma | I | - | Malignant |
| E5 | F | 38 | Rectum | Malignant melanoma | I | - | Malignant |
| E6 | F | 44 | Rectum | Malignant melanoma | I | - | Malignant |
| E7 | M | 64 | Rectum | Malignant melanoma | II | - | Malignant |
| E8 | F | 52 | Rectum | Malignant melanoma | I | - | Malignant |
| E9 | F | 84 | Rectum | Malignant melanoma of crissum | I | - | Malignant |
| E10 | F | 67 | Rectum | Malignant melanoma | I | - | Malignant |
| F1 | M | 66 | Rectum | Malignant melanoma | I | - | Malignant |
| F2 | F | 66 | Rectum | Malignant melanoma | I | - | Malignant |
| F3 | M | 75 | Rectum | Malignant melanoma | II | - | Malignant |
| F4 | F | 54 | Rectum | Malignant melanoma of anal tube | II | - | Malignant |
| F5 | F | 72 | Rectum | Malignant melanoma | I | - | Malignant |
| F6 | M | 55 | Stomach | Malignant melanoma | I | - | Malignant |
| F7 | M | 55 | Stomach | Malignant melanoma | I | - | Malignant |
| F8 | M | 50 | Esophagus | Malignant melanoma | II | - | Malignant |
| F9 | M | 64 | Esophagus | Malignant melanoma | I | - | Malignant |
| F10 | M | 71 | Intestine | Malignant melanoma | I | - | Malignant |
| G1 | M | 73 | Intestine | Malignant melanoma | I | - | Malignant |
| G2 | F | 70 | Oral cavity | Malignant melanoma of left parotid gland | I | - | Malignant |
| G3 | F | 63 | Lymph node | Metastatic malignant melanoma from right heel | - | - | Metastasis |
| G4 | M | 58 | Lymph node | Metastatic malignant melanoma from left groin | - | - | Metastasis |
| G5 | F | 55 | Lymph node | Metastatic malignant melanoma from left groin | - | - | Metastasis |
| G6 | M | 44 | Lymph node | Malignant malignant melanoma from right armpit | - | - | Metastasis |
| G7 | M | 72 | Lymph node | Metastatic malignant melanoma from right groin | - | - | Metastasis |
| G8 | F | 47 | Lymph node | Metastatic malignant melanoma from left thump | - | - | Metastasis |
| G9 | M | 63 | Lymph node | Metastatic malignant melanoma from left Lower gum | - | - | Metastasis |
| G10 | F | 40 | Lymph node | Metastatic malignant melanoma from right groin | - | - | Metastasis |
| H1 | M | 70 | Lymph node | Malignant malignant melanoma from right armpit | - | - | Metastasis |
| H2 | M | 56 | Lymph node | Metastatic malignant melanoma from left ear | - | - | Metastasis |

FIGURE 24C.

| H3 | M | 68 | Lymph node | Metastatic malignant melanoma from left groin | - | - | Metastasis |
|---|---|---|---|---|---|---|---|
| H4 | F | 72 | Lymph node | Metastatic malignant melanoma from left groin | - | - | Metastasis |
| H5 | F | 41 | Lymph node | Metastatic malignant melanoma from right groin | - | - | Metastasis |
| H6 | F | 61 | Lymph node | Metastatic malignant melanoma from groin | - | - | Metastasis |
| H7 | F | 38 | Lymph node | Metastatic malignant melanoma from right leg | - | - | Metastasis |
| H8 | F | 43 | Lymph node | Metastatic malignant melanoma from thigh | - | - | Metastasis |
| H9 | M | 73 | Lymph node | Metastatic malignant melanoma from right groin | - | - | Metastasis |
| H10 | F | 56 | Lymph node | Malignan tmalignant melanoma from left sole | - | - | Metastasis |
| I1 | F | 49 | Lymph node | Metastatic malignant melanoma from neck | - | - | Metastasis |
| I2 | F | 41 | Lymph node | Metastatic malignant melanoma from right groin (fibrous tissue and blood vessel) | - | - | Metastasis |
| I3 | M | 38 | Skin | Compound nevus of right face | - | - | Benign |
| I4 | F | 29 | Skin | Compound nevus of left shoulder | - | - | Benign |
| I5 | F | 30 | Skin | Intradermal nevus of left rump | - | - | Benign |
| I6 | F | 10 | Skin | Junctional nevus of right foot | - | - | Benign |
| I7 | F | 23 | Skin | Compound nevus of right lumbar part | - | - | Benign |
| I8 | M | 25 | Skin | Compound nevus of left leg | - | - | Benign |
| I9 | F | 2 | Skin | Junctional nevus of neck | - | - | Benign |
| I10 | M | 6 mon. | Skin | Intradermal nevus of face | - | - | Benign |
| J1 | M | 20 | Skin | Compound nevus of left shoulder | - | - | Benign |
| J2 | F | 2 | Skin | Intradermal nevus of right leg | - | - | Benign |
| J3 | M | 50 | Skin | Compound nevus of upper arm | - | - | Benign |
| J4 | M | 42 | Skin | Intradermal nevus of face | - | - | Benign |
| J5 | M | 55 | Skin | Compound nevus of back | - | - | Benign |
| J6 | M | 73 | Skin | Compound nevus of left heel | - | - | Benign |
| J7 | M | 39 | Skin | Intradermal nevuss of head | - | - | Benign |
| J8 | M | 11 | Skin | Intradermal nevuss of left thigh | - | - | Benign |
| J9 | F | 34 | Skin | Sebaceous nevus of head (skin tissue) | - | - | Benign |
| J10 | M | 18 | Skin | Sebaceous nevus of left frontal region (skin tissue) | - | - | Benign |

ANTI-CD133 MONOCLONAL ANTIBODIES AND RELATED COMPOSITIONS AND METHODS

PRIOR RELATED APPLICATIONS

The present application is a U.S. national phase under 35 U.S.C. 371 of International Patent Application No. PCT/US2016/024531, entitled "Anti-CD133 Monoclonal Antibodies and Related Compositions and Methods" and filed Mar. 28, 2016, which claims the benefit of U.S. Provisional Ser. No. 62/138,825, filed Mar. 26, 2015, the contents of each of which is incorporated herein by reference in its entirety.

FIELD

The products and processes described in this document relate to the fields of immunology, immunochemistry, immunoassays, screening assays, CD133 studies, cancer studies, cancer diagnostics, cancer therapies, stem cells, cancer stem cells and other related fields.

BACKGROUND

CD133, also known as prominin-1 and several other designations, is a glycoprotein known to be expressed in several types of stem cells, including hematopoietic stem cells, endothelial progenitor cells and neural stem cells. CD133 was found to be present or enriched in cell populations found in several human solid tumors, such as colon carcinoma, melanoma and brain tumors (for example, glioblastoma). Currently, CD133 is considered to be a putative marker for cancer stem cells (CSCs), which are cancer cells possessing stem-cell like characteristics, namely, an ability to differentiate into multiple-cell types, and the ability to give rise to new tumors. CD133 protein was found to localize to membrane protrusions and to be often expressed on adult stem cells. One proposed function for CD133 is maintenance of "stemness" through suppression differentiation.

Anti-CD133 monoclonal antibodies (mAbs) are an important tool in the areas of CD133 studies and detection, as well as in the areas of cancer studies, cancer detection, diagnostics and treatment, and other related fields. Available anti-CD133 monoclonal antibodies suffer from a number of deficiencies. For example, most of the early published work in the field of CD133 studies was carried out with monoclonal antibodies recognizing epitopes of CD133 that may have been glycosylated and became undetectable during cell differentiation. Other known monoclonal antibodies did not recognize certain posttranslationally modified forms of CD133. Some examples of anti-CD133 monoclonal antibodies recognized only unglycosylated CD133 epitopes, but not their glycosylated form and vice versa. In some other examples, anti-CD133 monoclonal antibodies were shown to be useful only in a limited range of biological assays. Accordingly, there is a need for anti-CD133 monoclonal antibodies that recognize a range of CD133 variants and isoforms with high specificity, regardless of the protein's glycosylation state or other posttranslational modifications, and are useful in a variety of applications. There is also a need for methods of producing such antibodies.

SUMMARY

This document describes novel anti-CD133 monoclonal antibodies having advantageous properties, such as high specificity and the ability to bind to both glycosylated and unglycosylated forms of CD133. The new monoclonal antibodies are suitable for a wide range of analytical and diagnostic assays and techniques, are useful in research, analytical and diagnostic applications, and can be employed as therapeutic agents. Also described in this document are products and compositions that include the anti-CD133 monoclonal antibodies, methods (processes) of making and using the improved anti-CD133 monoclonal antibodies, and related compositions and kits. The foregoing antibodies, products, compositions, processes, methods and kids are included among the embodiments of the present invention.

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. Covered embodiments of the invention are defined by the claims, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim. Some non-limiting exemplary embodiments of the present invention are summarized below.

Among the exemplary embodiments of the present invention are monoclonal antibodies, such as: an anti-CD133 monoclonal antibody having an antibody binding site capable of specifically binding an epitope comprising SEQ ID NO: 17 or a variant thereof: an anti-CD133 monoclonal antibody having an antibody binding site comprising SEQ ID NO:9 and SEQ ID NO:11 or a variant thereof; an anti-CD133 monoclonal antibody having an antibody binding site comprising a polypeptide encoded by SEQ ID NO:10 and SEQ ID NO: 12 or a variant thereof; an anti-CD133 monoclonal antibody having an antibody binding site comprising CDRs contained in SEQ ID NO:9 and SEQ ID NO:11 or a variant thereof. The above antibodies may be capable of specifically binding domain A but not domain B of a CD133 polypeptide, glycosylated or unglycosylated, which, in turn, may contain any one of SEQ ID NOs 1-8 or a variant thereof.

Also included among the exemplary embodiments of the present invention are anti-CD133 monoclonal antibodies having or more of the following features: an anti-CD133 monoclonal antibody capable of specifically binding an epitope comprising SEQ ID NO: 18; an anti-CD133 monoclonal antibody having an antibody binding site comprising SEQ ID NO: 13 and SEQ ID NO:15 or a variant thereof; an anti-CD133 monoclonal antibody having an antibody binding site comprising a polypeptide encoded by SEQ ID NO: 14 and SEQ ID NO:16 or a variant thereof: and an anti-CD133 monoclonal antibody having an antibody binding site comprising CDRs contained in SEQ ID NO: 13 and SEQ ID NO: 15 or a variant thereof. The above monoclonal antibodies may be capable of specifically binding domain B but not domain A of a CD133 polypeptide, glycosylated or unglycosylated, which may comprise any one of SEQ ID NOs 1-8 or a variant thereof. The above anti-CD133 monoclonal antibodies may be capable of specifically binding an epitope comprising SEQ ID NO: 18 or a variant thereof.

An anti-CD133 monoclonal antibody according to the embodiments of the present invention may be a non-human antibody, a human antibody, or a human-like antibody. The anti-CD133 monoclonal antibody may be a reduced immunogenicity antibody, a humanized antibody or a chimeric antibody. The anti-CD133 monoclonal antibody may be or comprise an antibody fragment. The anti-CD133 monoclonal antibody may be recombinantly produced. The anti-CD133 monoclonal antibody may have an amino acid sequence that is different from an amino-acid sequence of a naturally occurring anti-CD133 monoclonal antibody. The anti-CD133 monoclonal antibody may contain a label, a tag, a bioactive substance, a drug, a radioactive moiety or a toxic moiety, any or all of which may be not naturally occurring in a monoclonal antibody molecule. In one example, the anti-CD133 monoclonal antibody may contain a fluorescent label or a fluorescent tag.

The anti-CD133 monoclonal antibody may be employed in a variety of uses and methods, which are included among the embodiments of the present invention. Some examples of such methods are as follows. Among the methods of the present invention is a method of detecting ("detection method") a presence or absence of CD133 polypeptide in a sample, comprising steps of contacting the sample with the monoclonal antibody of any one of an anti-CD133 monoclonal antibody under conditions under which specific binding of the monoclonal antibody and the CD133 polypeptide may occur, and detecting the specific binding of the monoclonal antibody to the CD133 polypeptide, wherein the detected specific binding is indicative of the presence of the CD133 polypeptide in the sample. The method may further comprise determining an amount of CD133 polypeptide present in the sample. The sample may be a cell sample, a tissue sample, an aqueous sample, a solution, a suspension, a blot or an electrophoresis gel. The sample may be a cancerous tissue sample. The specific binding may be detected in an ELISA, a Western Blot assay or in an immunofluorescence assay.

The above detection method can be adapted to a variety of uses or practical applications, which can also be referred to as "methods." One example of such practical application is assessing status of a cancer in a patient, comprising obtaining the sample from the patient and performing the above detection method, wherein the presence, absence or amount of CD133 polypeptide detected in the sample is indicative of the status of the cancer in the patient. One more example of the practical application of the detection method is treating a cancer in a patient, comprising performing the above detection method, wherein the presence of CD133 polypeptide detected in the sample or the amount of CD133 polypeptide present in the sample above a predetermined threshold value is indicative of a need to administer a cancer treatment to the patient, and administering the cancer treatment to the patient. The cancer treatment may be a chemotherapy, drug therapy, targeted drug therapy, surgery, radiation therapy, an antibody therapy or a combination thereof. The cancer may be breast cancer, colorectal cancer, glioblastoma, melanoma, lung cancer, ovarian cancer, gastric cancer, acute leukemia, acute lymphoblastic leukemia (AML), prostate cancer, liver cancer, kidney cancer sarcomas, brain cancers, leukemia or retinoblastoma. Another example of a practical application of the detection method is a method of detecting presence, absence or amount of cancer stem cells in the sample, comprising performing the above detection method, wherein the presence, absence or amount of CD133 polypeptide detected in the sample is indicative of the presence, absence or amount of the cancer stem cells in the sample. Yet one more example of the practical application of the detection method is detecting presence, absence or amount of circulating tumor cells in the sample, comprising performing the above detection method, wherein the sample is a blood sample and the presence, absence or amount of CD133 polypeptide detected in the sample is indicative of the presence, absence or amount of the circulating tumor cells in the sample. One more example detection of presence, absence or amount of CD133-positive cells in the sample, comprising performing the above detection method, wherein the sample is a blood sample and the presence, absence or amount of CD133 polypeptide detected in the sample is indicative of the presence, absence or amount of the CD133-positive cells in the sample.

Also included among the embodiments of the present invention is a method of removing CD133-positive cells from a sample, comprising contacting the sample with the anti-CD133 monoclonal antibody under conditions under which specific binding of the monoclonal antibody and CD133 polypeptide expressed by the CD133-positive cells may occur, thereby allowing complexes the monoclonal antibody and the CD133-positive cells to form, and removing the monoclonal antibody and the CD133-positive cells from the sample. The sample can be a blood sample or a marrow sample. A method of treating or alleviating ("treatment method") a disease or a condition in a subject, comprising administering to the subject a composition containing one or more of the anti-CD133 monoclonal antibodies is also included among the embodiments of the present invention. One example of the disease or the condition thus treated or alleviated is a cancer, such as breast cancer, colorectal cancer, glioblastoma, melanoma, lung cancer, ovarian cancer, gastric cancer, acute leukemia, acute lymphoblastic leukemia (AML), prostate cancer, liver cancer, kidney cancer sarcomas, brain cancers, leukemia or retinoblastoma. In the treatment method, an antibody can be a human-like antibody and the subject can be a human. The antibody can also be not a human-like antibody and the subject may not be not a human. The anti-CD133 monoclonal antibody employed in a treatment method may be a neutralizing antibody.

One more exemplary use of anti-CD133 monoclonal antibodies according to the embodiments of the present invention is a method of assessing or optimizing efficacy of a therapy in a subject with a disease or a condition, comprising determining a value of CD133 in one or more samples obtained from the subject, wherein the determining comprises contacting the one or more samples with the anti-CD133 monoclonal antibody under conditions under which specific binding of the monoclonal antibody and a CD133 polypeptide may occur, and detecting the specific binding of the monoclonal antibody to the CD133 polypeptide. The detected specific binding is indicative of the value CD133 in the one or more samples. The term "value of CD133" in the one or more samples encompasses presence, absence, or amount of CD133 in the one or more samples. The efficacy of the therapy is determined by comparing the determined value CD133 in the one or more samples to a predetermined threshold value of CD133. The value of CD133 in the one or more samples may be determined one or more times before, during, or after therapy, or any combination thereof. The predetermined threshold value of CD133 may be value based on at least one of the one or more samples. An increase in CD133 value may indicate the therapy is insufficiently effective. Thus, an additional therapy or a change in dosing regimen of the therapy may be indicated to the subject. On the other hand, a decrease in CD133 value may indicate that the therapy is effective. The therapy of the additional therapy may be chemotherapy, drug therapy, targeted drug therapy, surgery, radiation therapy, an antibody therapy or a combination thereof. The sample may be a cell sample, a tissue sample, an aqueous sample, a solution, a suspension, a blot or an electrophoresis gel. For example, the sample may a blood sample or a plasma sample. In the above methods, the specific binding may be detected in an ELISA, a Western Blot assay or in an immunofluorescence assay. The subject may be a cancer subject, meaning the subject who has a cancer. Examples of the subject's cancer are breast cancer, colorectal cancer, glioblastoma, melanoma, lung cancer, ovarian cancer, gastric cancer, acute leukemia, acute lymphoblastic leukemia (AML), prostate cancer, liver cancer, kidney cancer sarcomas, brain cancers, leukemia or retinoblastoma.

Exemplary embodiments of the present invention include a method of producing an anti-CD133 monoclonal antibody, comprising the steps of administering to a subject or a cell an immunogenic composition comprising one or more polypeptide selected from the group consisting of SEQ ID NO: 17, SEQ ID NO: 18 and variants thereof to generate multiple antibody producing cells, isolating an antibody producing cell from the multiple antibody producing cells; culturing the isolated antibody producing cells under conditions leading to production of anti-CD133 monoclonal antibody, and testing the monoclonal antibody for specific binding to a polypeptide having the amino acid sequence of SEQ ID NO:17 or SEQ ID NO: 18. The method of producing may further comprise determining one or more nucleic acid sequences encoding an antibody binding site of the anti-CD133 monoclonal antibody, and using the one or more nucleic acid sequences to produce a recombinant anti-CD133 monoclonal antibody. Expression vectors related to anti-CD133 monoclonal antibodies are also included in the embodiments of the present invention, for example: an expression vector comprising nucleic acid sequences encoding one or both of SEQ ID NO:9 and SEQ ID NO: 11 or variants thereof: an expression vector comprising SEQ ID NO: 10 and SEQ ID NO: 12 or variants thereof; an expression vector comprising nucleic acid sequences encoding one or more CDRs contained in SEQ ID NO:9, SEQ ID NO: 11 or variants thereof; an expression vector comprising nucleic acid sequences encoding one or both of SEQ ID NO: 13 and SEQ ID NO:15 or variants thereof; an expression vector comprising nucleic acid sequences encoding one or more CDRs contained in SEQ ID NO:13, SEQ ID NO:15 or variants thereof; an expression vector comprising SEQ ID NO:14 and SEQ ID NO: 16 or variants thereof some other example of the embodiments of the present invention are a cell comprising the above expression vectors, a method of producing an anti-CD 133 monoclonal antibody, comprising the steps of introducing the expression vector into a cell and culturing the cell under conditions leading to expression of the anti-CD133 monoclonal antibody, and a method of producing an anti-CD133 monoclonal antibody, comprising a step of culturing the cell under conditions leading to expression of the anti-CD 133 monoclonal antibody.

Some other exemplary embodiments of the present invention are as follows. An immunogenic composition comprising one or more polypeptides comprising at least one of SEQ ID NO: 17 or a variant thereof or SEQ ID NO: 18 or a variant thereof, and a carrier or an adjuvant. A screening agent comprising one or more polypeptides comprising at least one of SEQ ID NO: 17 or a variant thereof or SEQ ID NO: 18 or a variant thereof, and a carrier, a tag or a label, including a non-naturally occurring tag or label. A method of determining a presence, an absence or an amount of an anti-CD133 monoclonal antibody in a sample, comprising the steps of contacting the sample with the screening reagent and detecting a specific binding of the screening reagent to the anti-CD133 monoclonal antibody in the sample, wherein presence of the detected specific binding is indicative of the presence of the anti-CD133 monoclonal antibody in the sample.

It is to be understood that "variant" or "variants" referred to in the above description of the exemplary embodiment may be a sequence variant of the corresponding amino acid or a nucleic acid sequence having a degree of homology with the corresponding sequence of least 60%, 65%, 70%, 75%, 80%, 85%, 90%, 91%, 92%, 93%, 94%, 95%, 96%, 97%, 98% or 99%. Other objects and advantages of the invention will be apparent from the following detailed description of embodiments of the invention.

BRIEF DESCRIPTION OF THE FIGURES

FIG. 2 A, B, FIG. 2 C, D, E and FIG. 2 F, G, H reproduce amino acid sequences of CD133 polypeptides from several species. In FIG. 2 A, B—Panel A: CD133 polypeptide, *Homo sapiens*, SEQ ID NO:1 (National Center for Biotechnology Information (NCBI) accession number NP_006008.1); Panel B: Prominin-1 isoform 1, *Gorilla gorilla gorilla*, SEQ ID NO:2 (NCBI reference sequence XP_004038519). In FIG. 2 C, D, E—Panel C: Prominin-1 isoform X1, *Pan troglodytes*, SEQ ID NO:3 (NCBI reference sequence XP_003310298); Panel D: Prominin 1.s1 splice variant, *Canis lupus familiaris*, SEQ ID NO:4 (NCBI GenBank reference AIA08974.1); Panel E: Prom1 protein, *Mus musculus*, SEQ ID NO:5 (NCBI accession number AAH28286.1). In FIG. 2 F, G, H—Panel F: Prominin-1 isoform 1 precursor, *Rattus norvegicus*, SEQ ID NO:6 (NCBI accession number NP_068519.2); Panel G: Prominin-1 isoform X6, *Homo sapiens*, SEQ ID NO:7 (NCBI reference sequence XP_011512200); Panel H: Prominin-1 isoform X5, *Canis lupus familiaris*, SEQ ID NO:8 (NCBI reference sequence XP_005618614.1).

FIG. 4 shows the line plots illustrating the results of ELISA specificity testing for mAb 47-10 (panel A) and clone 133-3 (panel B) conducted using the plates coated with 100 ng per well of the following antigens: recombinant CD133

Extracellular Domain A (CD133A) or Domain B (CD133B); BSA-conjugated antigenic peptide A (PepA) or peptide B (Pep B).

FIG. 5 shows the amino acid and nucleotide sequences of mAb 47-10. Panel A shows heavy chain sequences: amino acid sequence—SEQ ID NO:9; nucleotide sequence—SEQ ID NO: 10. Panel B shows light chain sequences: amino acid sequence—SEQ ID NO: 11; nucleotide sequence—SEQ ID NO:12.

FIG. 6A and FIG. 6B show the amino acid and nucleotide sequences of mAb 133-3. FIG. 6A shows heavy chain sequences: amino acid sequence—SEQ ID NO:13; nucleotide sequence—SEQ ID NO: 14. FIG. 6B shows light chain sequences: amino acid sequence—SEQ ID NO: 15; nucleotide sequence—SEQ ID NO: 16.

FIG. 7 illustrates the structure of the heavy chain complementarity determining regions (CDRs) of mAb 47-10; residues 19-127 of 450 residues of SEQ ID NO:9. The framework regions are represented with light grey (or no bar), and CDRs are represented by darker grey bars. The framework regions continue beyond the light grey bars, so that the abut each CDR and continue to the end of the sequence. The insertions are highlighted in grey. The arrows mark unusual residues found in less than 1% of the sequences.

FIG. 8 illustrates the structure of the light chain of mAb 47-10; residues 23-138 out of 239 residues of SEQ ID NO:11. The framework regions are represented with light grey bars (or no bar), and CDRs are represented by darker grey bars. The framework regions continue beyond the light grey bars, so that the abut each CDR and continue to the end of the sequence. The insertions are highlighted in grey; the arrows mark unusual residues found in less than 1% of the sequences.

Figure 9:
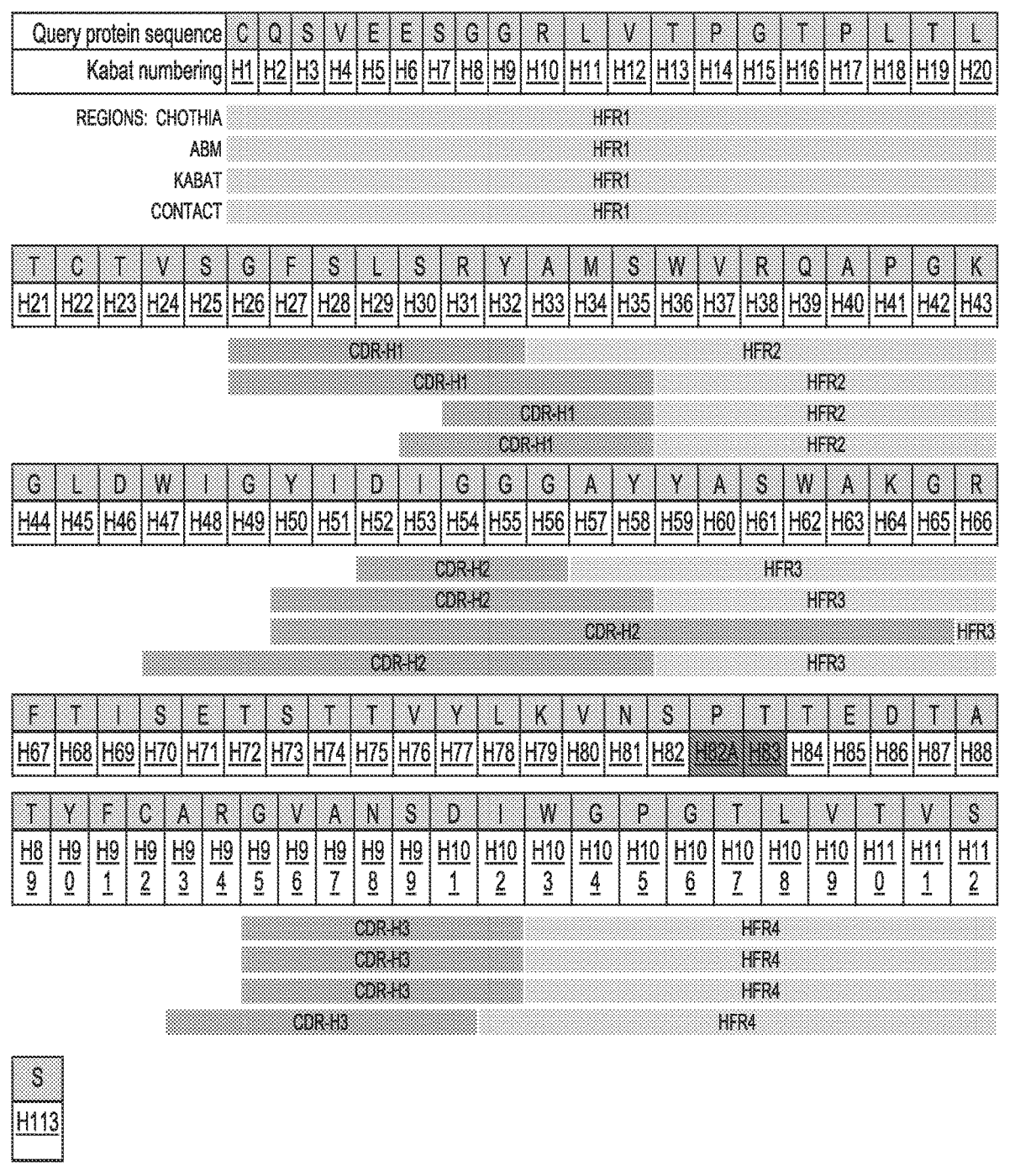

FIG. 9 illustrates the structure of the heavy chain of mAb 133-3; residues 19-131 of 454 residues of SEQ ID NO:13. The CDRs are shown in dark grey, and the framework regions are represented with lighter grey bars (or no bar). The framework regions continue beyond the light grey bars, so that the abut each CDR and continue to the end of the sequence. The insertions are highlighted in grey; the arrows mark unusual residues found in less than 1% of the sequences.

Figure 10:
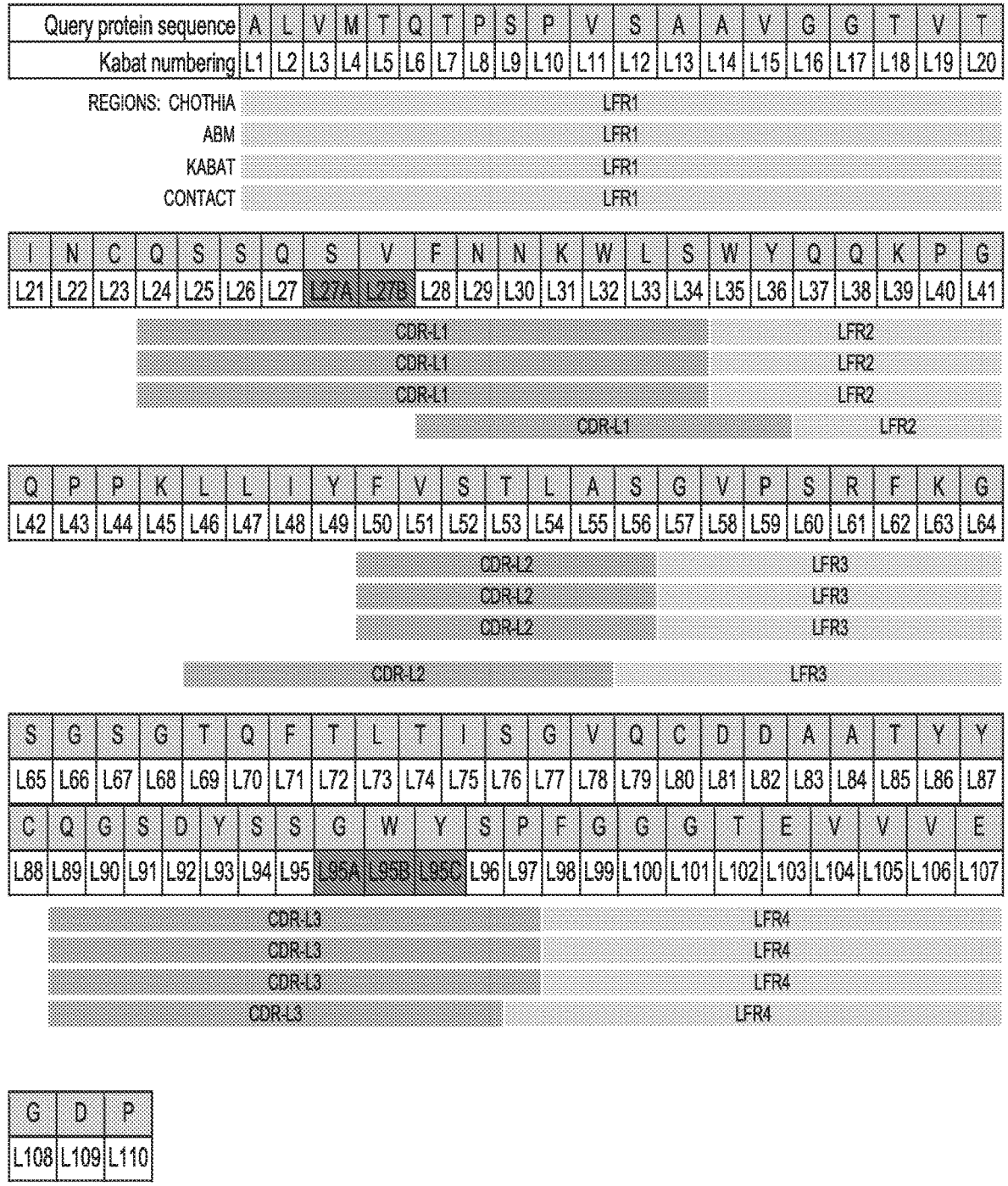

FIG. 10 illustrates the structure the light chain of mAb 133-3; residues 23-137 out of 238 residues of SEQ ID NO:15. The framework regions are represented with light grey bars (or no bar) and CDRs are represented by darker grey bars. The framework regions continue beyond the light grey bars, so that the abut each CDR and continue to the end of the sequence. The insertions are highlighted in grey; the arrows mark unusual residues found in less than 1% of the sequences.

Figure 11:
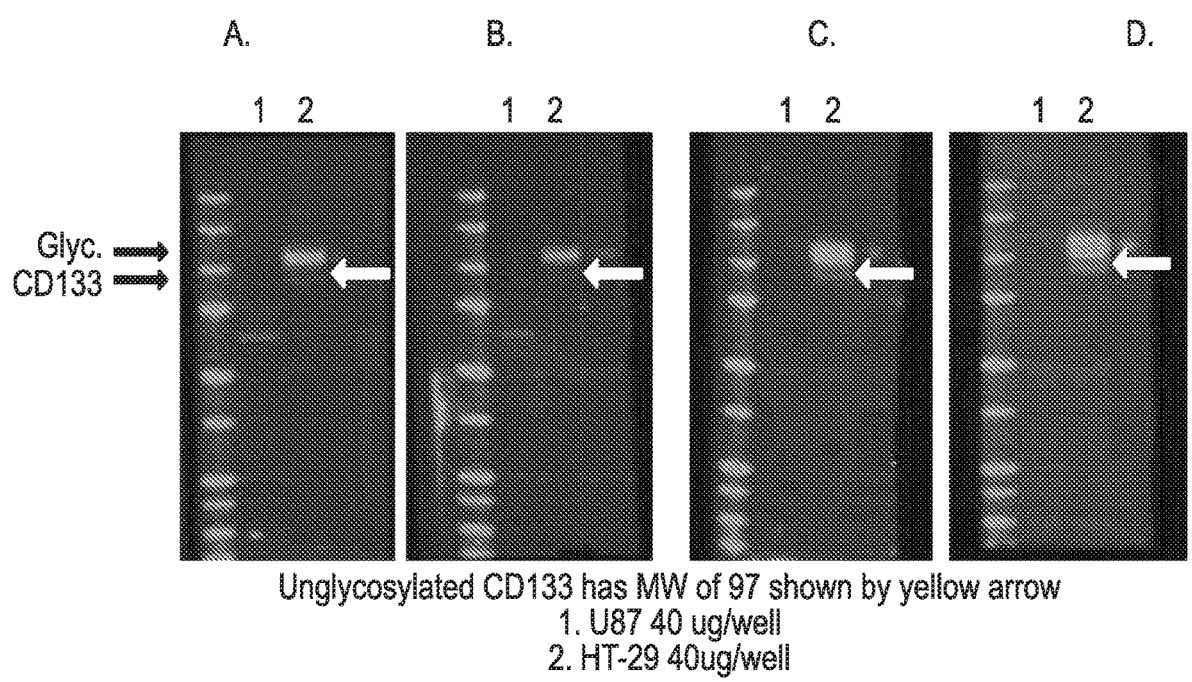

FIG. 11 shows the images of Western blots of cell lysates of U87 cells (CD133-negative cells; lane 1 in each blot) and HT-29 cells (CD133-positive cells; lane 2 in each blot). Panels A and B show Western blots stained with different subclones of mAb 47. Panels C and D show Western blots stained with different subclones of mAb 133 clone. The left lane of each blot shows molecular weight (MW) standards. The unlabeled arrows at the right of lane 2 in each panel point at a band for unglycosylated CD133 having a MW of 97 kDa. The arrows labelled "Glyc. CD133" point at an approximate location of a band for glycosylated CD133 having a MW of ~133 kDa.

Figure 12:
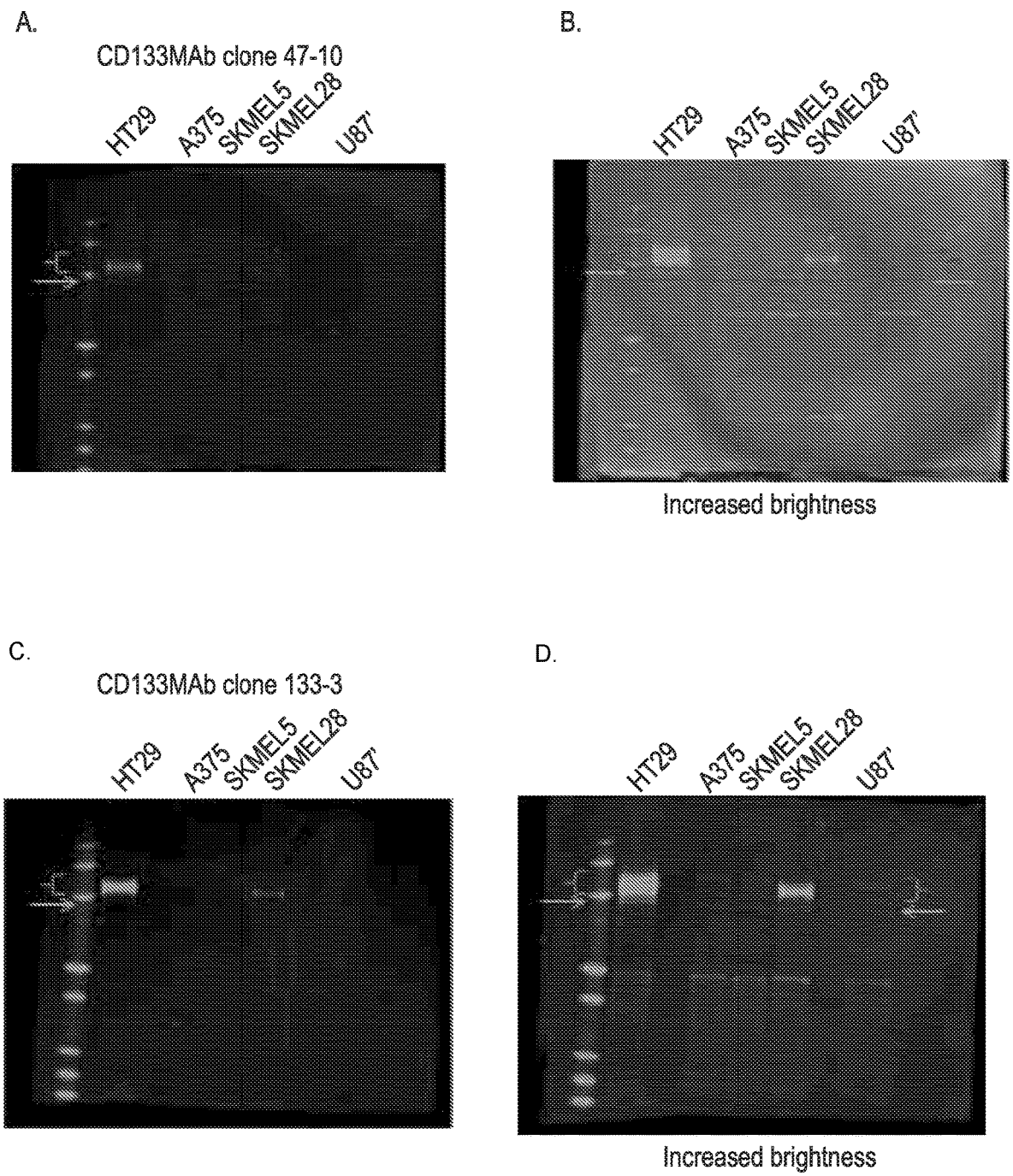

FIG. 12 shows the images of Western blots of the cell lysates of cell lines HT29, A375, SKMEL5, SKMEL28 and U87 (as labeled, left to right, the first left lane in each blot contains MW standards). Panels A (lowered brightness) and B (increased brightness) show Western blots using mAb 47-10. Panels C (lowered brightness) and D (increased brightness) show Western blot using mAb 133-3. The arrows at the left of MW standards point at the band locations for unglycosylated CD133 having MW of 97 kDa. The brackets show approximate location of the band for glycosylated CD133. Western blot conditions were as follows: 4-12% gel; 40 µg protein/lane, except for U87 lane (20 µg/lane); the blots were incubated with 1 µg/ml primary rabbit anti-CD133 monoclonal antibodies for 2 hours at room temperature, with 0.1 µg/ml secondary antibody GAR-IR-800 (Li-Cor) 1 hour at room temperature.

FIG. 13 shows the images illustrating the results of immunofluorescence testing of mAb 133-3 with H29 cells (panel A) and U87 cells (panel B). Formalin-fixed, paraffin-embedded (FFPE) samples of the cell pellets were stained for CD133 by mAb at 10 µg/ml, followed by anti-rabbit-AF546 antibody (Life Technologies); nuclei were stained with 4',6-diamidino-2-phenylindole (DAPI) fluorescent stain.

FIG. 14 shows the images showing the results of immunofluorescence testing of mAb 47-10 with H29 cells (panel A) and A375 cells (panel B). FFPE samples of cell pellets were stained for CD133 by mAb at 10 µg/ml, followed by anti-rabbit-AF546 antibody; nuclei were stained with DAPI.

FIG. 15 shows the images illustrating the results of immunofluorescence testing of mAbs 133-3 (panel A) and 47-10 (panel B) with A375 xenograft cells. FFPE samples of cell pellets were stained for CD133 by mAb at 10 µg/ml, followed by anti-rabbit-AF546 antibody; nuclei were stained with DAPI.

Figure 16:
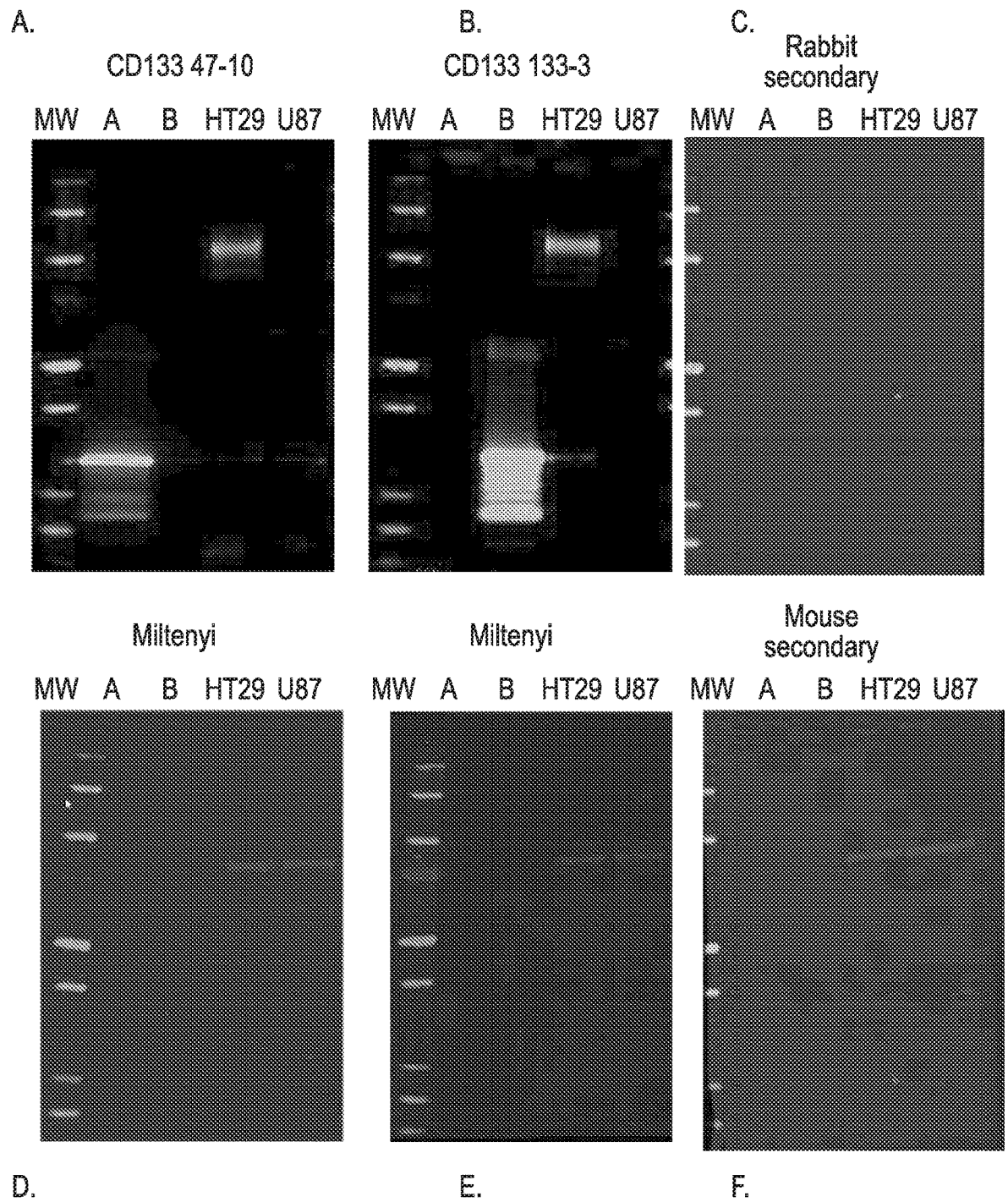

FIG. 16 shows the images of Western blots illustrating the results of the comparative testing of mAbs 47-10 and 133-3 and commercially available anti-CD133 mAbs. mAbs 47-10 (panel A), 133-3 (panel B) and commercial mAbs obtained from Miltenyi Biotec (AC133—panel D; 293C3—panel E) were used as primary antibodies. Panels C and F show negative control Western blots prepared with rabbit (panel C) and mouse (panel F) secondary antibodies but no primary antibody. The lanes of the Western blots are as follows: MW—molecular weight marker; A—recombinant CD133 extracellular domain A; B—recombinant CD133 extracellular domain B; HT-29—HT29 cell lysate; U87—U87 cell lysate.

Figure 17:
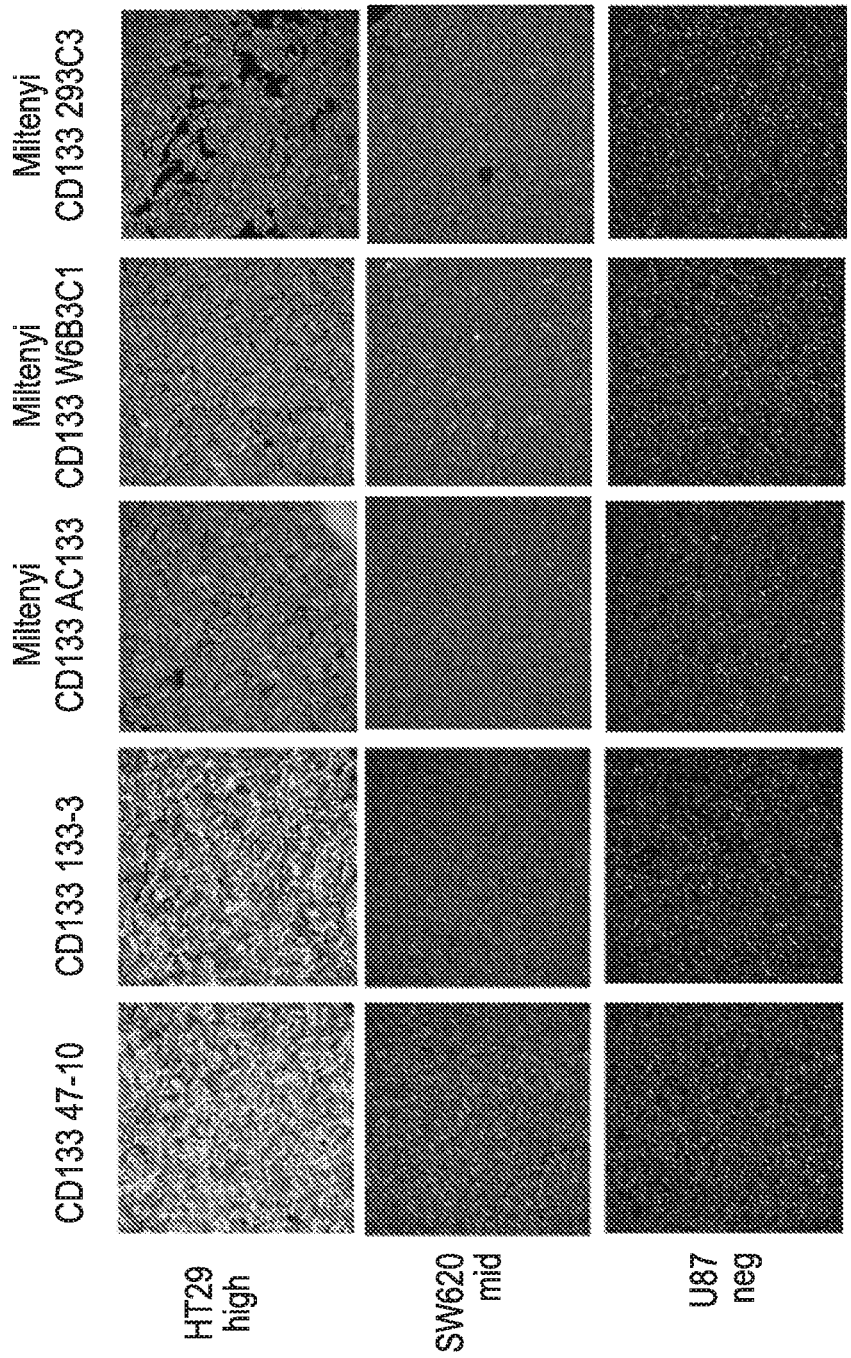

FIG. 17 shows the images, organized as matrix, depicting immunofluorescence staining of FFPE samples of cells representing the cell lines with varying CD133 mRNA expression level (rows, top to bottom: HT29—high; SW620—medium; U87—CD133 negative) with various antibodies (columns, top to bottom: mAb 47-10; mAb 133-3; Miltenyi Biotec AC133 mAb; Miltenyi Biotec W683C1 mAb; Miltenyi Biotec 293C3 mAb).

Figure 18:
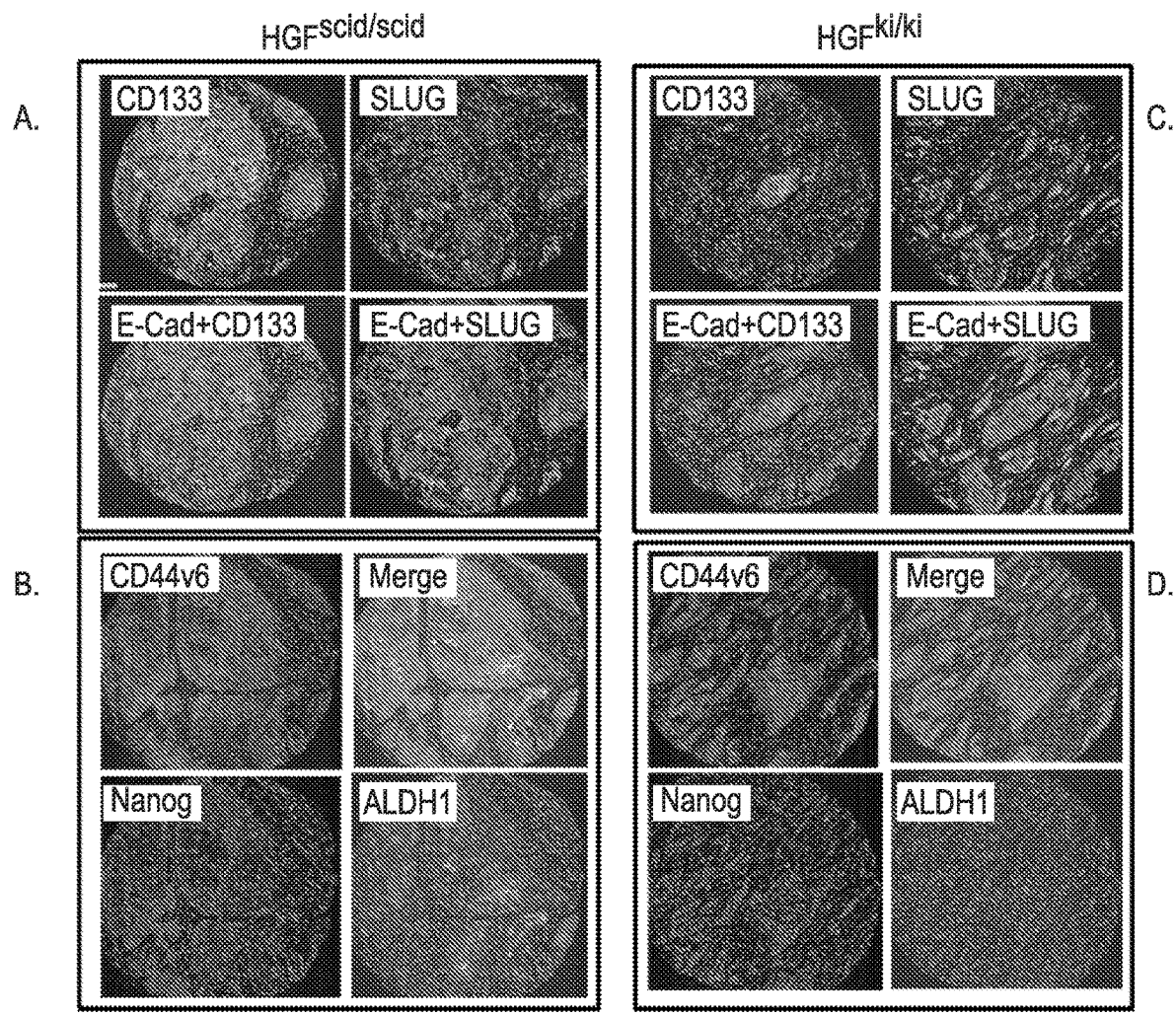

FIG. 18 shows the images depicting the results of the immunofluorescence staining of H596 non-small cell lung cancer xenograft tumor samples from mice expressing known cancer stem cell biomarkers, including CD133. See, for example, Akunuru et al. 2012 "Non-small cell lung cancer stem/progenitor cells are enriched in multiple distinct phenotypic subpopulations and exhibit plasticity." *Cell Death and Disease,* 3:1-10; Bertolini et al. 2009 "Highly tumorigenic lung cancer CD133+ cells display stem-like features and are spared by cisplatin treatment" PNAS 106: 16281-16286; Karimi-Busheri et al. 2013 "CD24+/CD38− as new prognostic marker for non-small cell lung cancer." *Multidisciplinary Respiratory Medicine* 8:65-74. Panels A and B show representative images of multiplex immunofluorescent epithelial to mesenchymal transition (EMT) and/ or cancer stem cell (CSC) biomarker staining of H596 tumors grown in immunocompromised hHGF$^{scid/scid}$ mice (mice homozygous for both the hHGFki and Prkdcscid alleles, also called immunocompromised hHGFki mice, which are available from Jackson Laboratory for Genomic Medicine (USA)). Panels C and D show representative images of multiplex immunofluorescent epithelial to mesenchymal transition and/or cancer stem cell biomarker staining of H596 tumors grown in hHGF$^{ki/ki}$ mice (mice that harbor a "humanized" knock-in mutation (hHGFki) that replaces the mouse hepatocyte growth factor (HGF) coding factor, and the Prkdc$^{scid}$ mutation that results in T- and B-cell deficiency; these mice may be useful for studying the HGF/MET pathway in human tumor xenografts and mouse tumor allografts). To obtain the images shown in panels A and C, two adjacent tissue sections from each tumor were stained with E-Cadherin (clone 36, BD Biosciences) and CD133 (mAb clone 47-10) or E-Cadherin and Slug. To obtain the images shown in panels B and D, known cancer stem cell lung biomarkers such as CD44 and ALDH1 (as labeled) were used. Nanog was another CSC biomarker that was not expressed in these tissues. The merged images show the overlapped layers for all CSC biomarker layers (CD44, Nanog and ALDH1).

Figure 19:
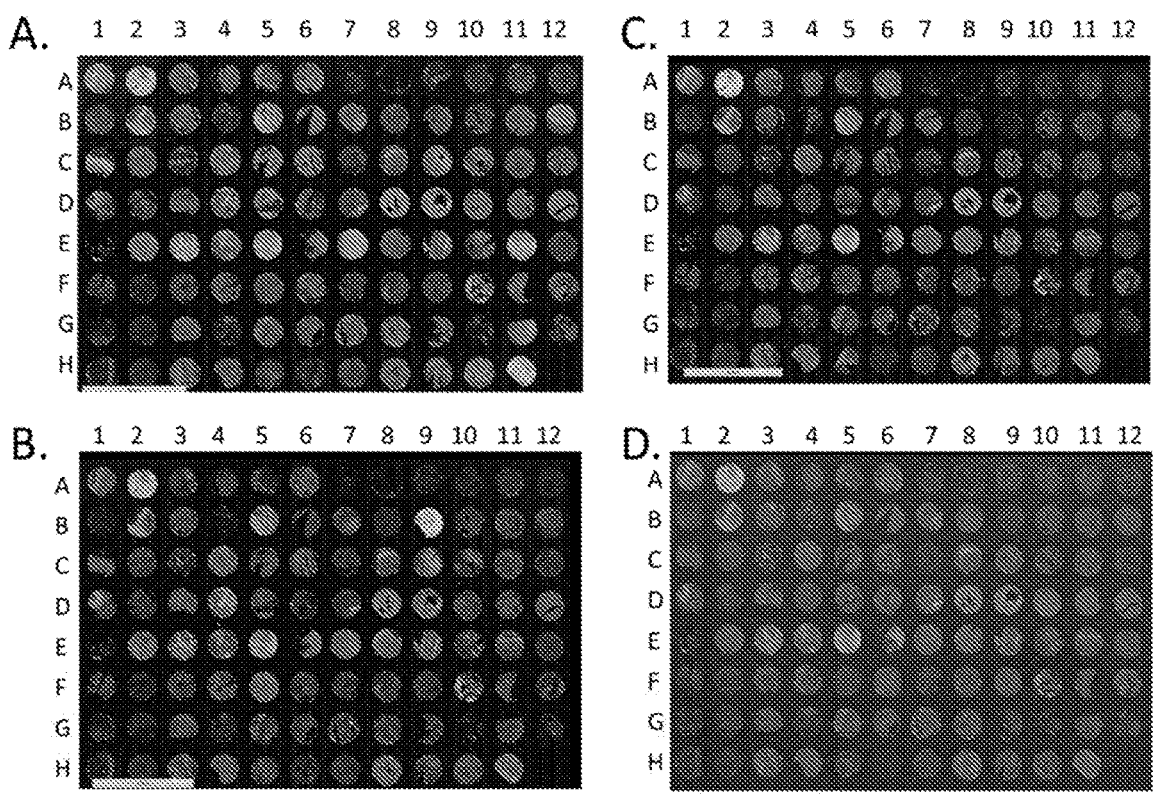

FIG. 19 shows the images depicting the results of CD133 staining of multi tumor tissue array (TMA) MTU951, Biomax, Inc. Panel A: CD133 Multiple Tumor (MTU951) TMA CD133 (clone 133-3); Panel B: CD133 Multiple Tumor (MTU951) TMA CD133 (mAb 47-10), Panel C: CD133 Multiple Tumor (MTU951) TMA CD133 (293C3). Panel D: CD133 Multiple Tumor (MTU951) TMA CD133 (ACC133). Panel E: Array map: Adr—Adrenal gland, Bla—Bladder, urinary. Bon—Bone, scapula, Bra—Brain, Bre—Breast, Eso—Esophagus, Hea—Head and neck, nasal cavity, Int—Intestine, rectum, Kid—Kidney, Liv—Liver, Lun—Lung, Lym—Lymph node, Ova—Ovary, Pan—Pancreas, Pro—Prostate, Ski—Skin, trunk, Sto—Stomach, Tes—Testis, Thr—Thyroid, Ute—Uterus, endometrium; Color coding employed in the original image and illustrated in the legend was as follows: light blue—benign tumor, white, dark blue—malignant tumor, yellow—metastasis, light green—normal tissue. In the greyscale reproduction, medium grey—benign tumor, white, dark grey—malignant tumor, dark grey—metastasis, light grey—normal tissue.

FIG. 20A. FIG. 20B and FIG. 20C show the specifications of the tumor tissue array MTU951 used in the experiments illustrated in FIGS. 19, 21A and 21B, Biomax, Inc. 2003-2014.

Figure 21:
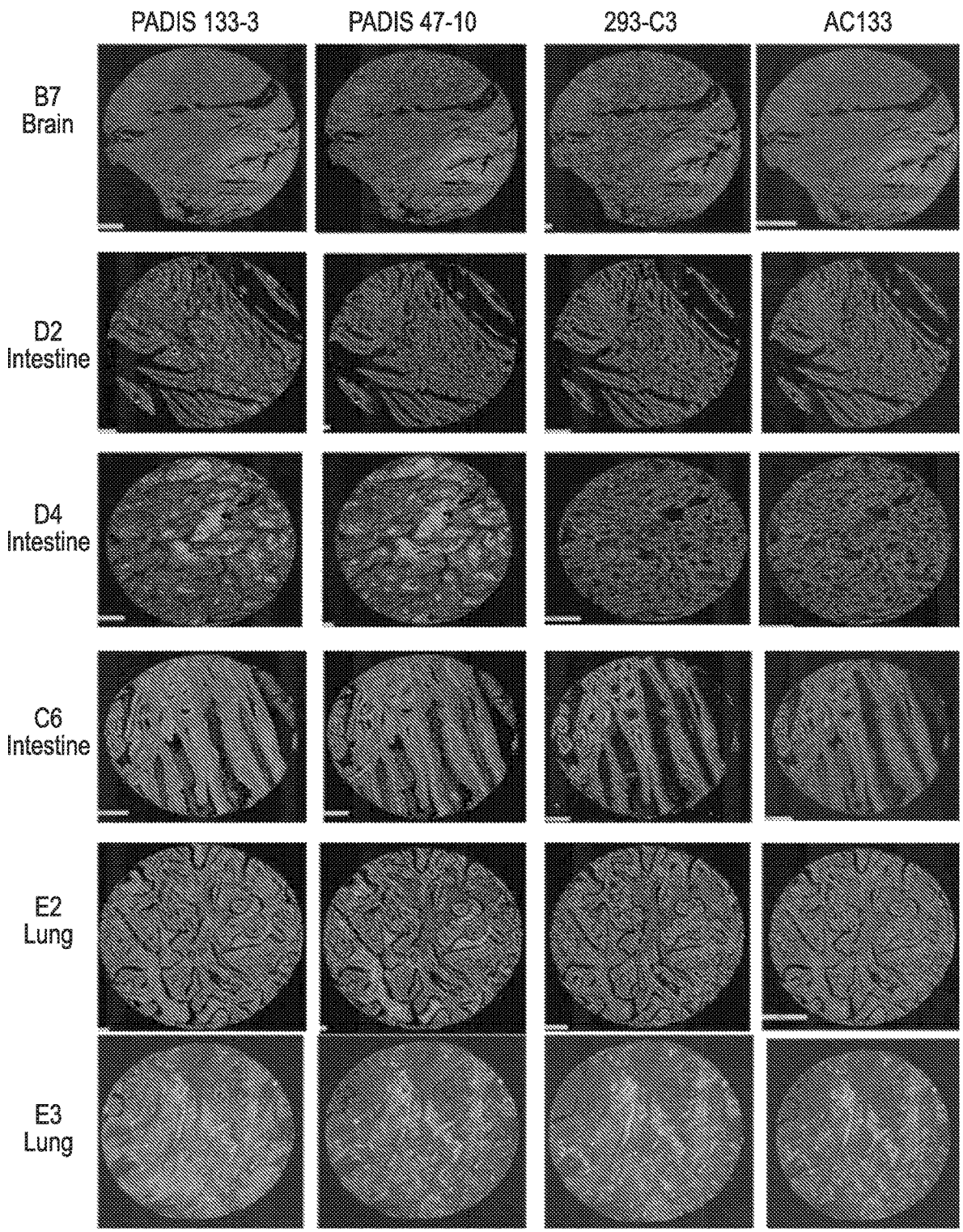

FIG. 21 shows the images depicting the results of CD133 staining of selected tumor cores from multi tumor TMA (MTU951, Biomax) stained with CD133 (mAb 133-3, mAb 47-10, 293C3, or AC133—as indicated in the figure.

Figure 22:
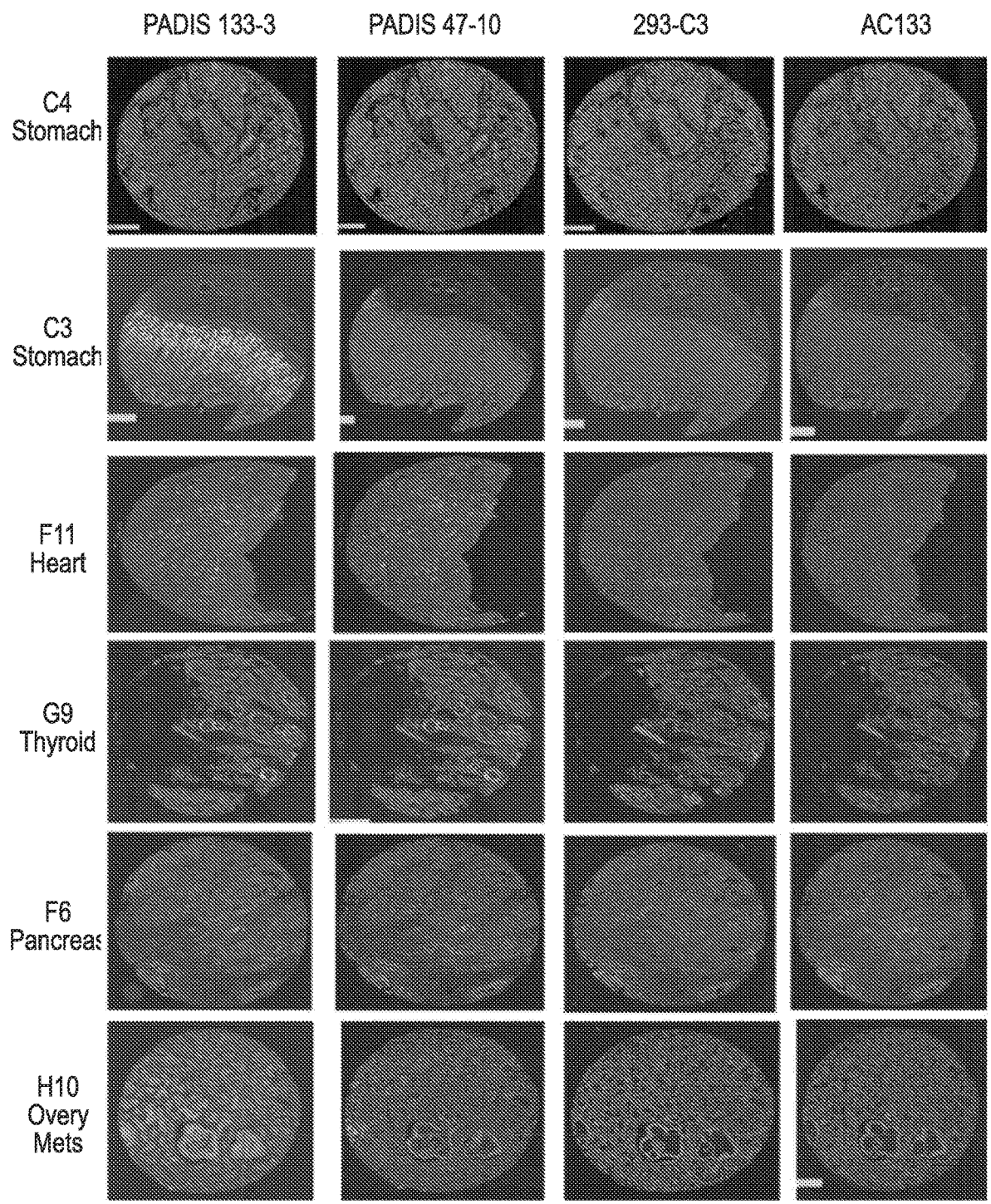

FIG. 22 shows the images depicting the results of CD133 staining of selected tumor cores from multi tumor TMA (MTU951, Biomax) stained with CD133 (mAb 133-3, mAb 47-10, 293C3, or AC133—as indicated in the figure.

Figure 23:
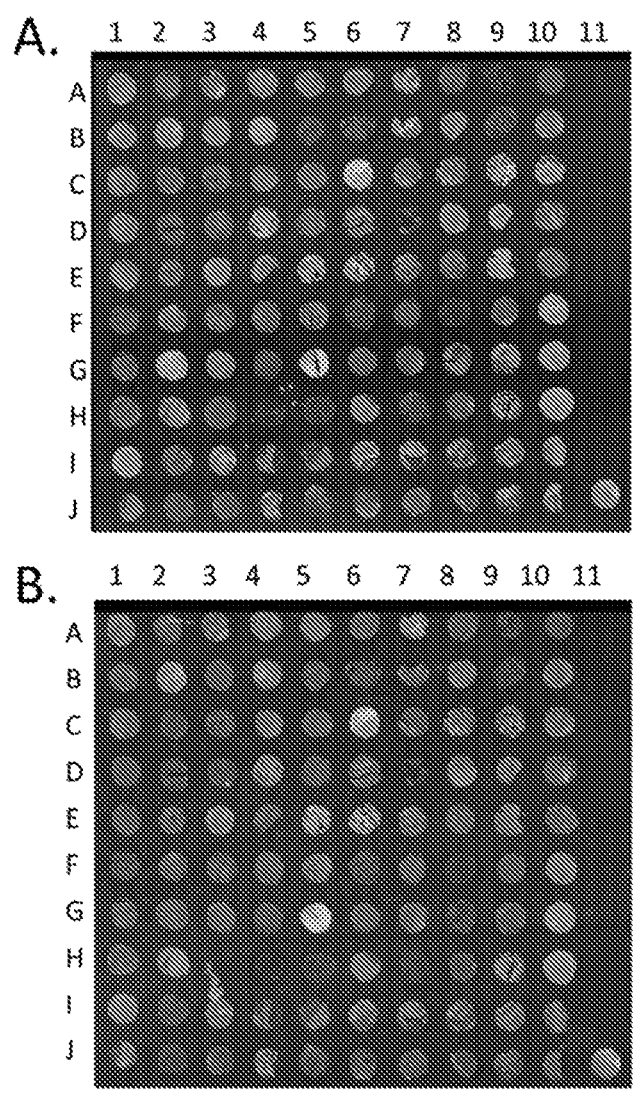
Figure 23:
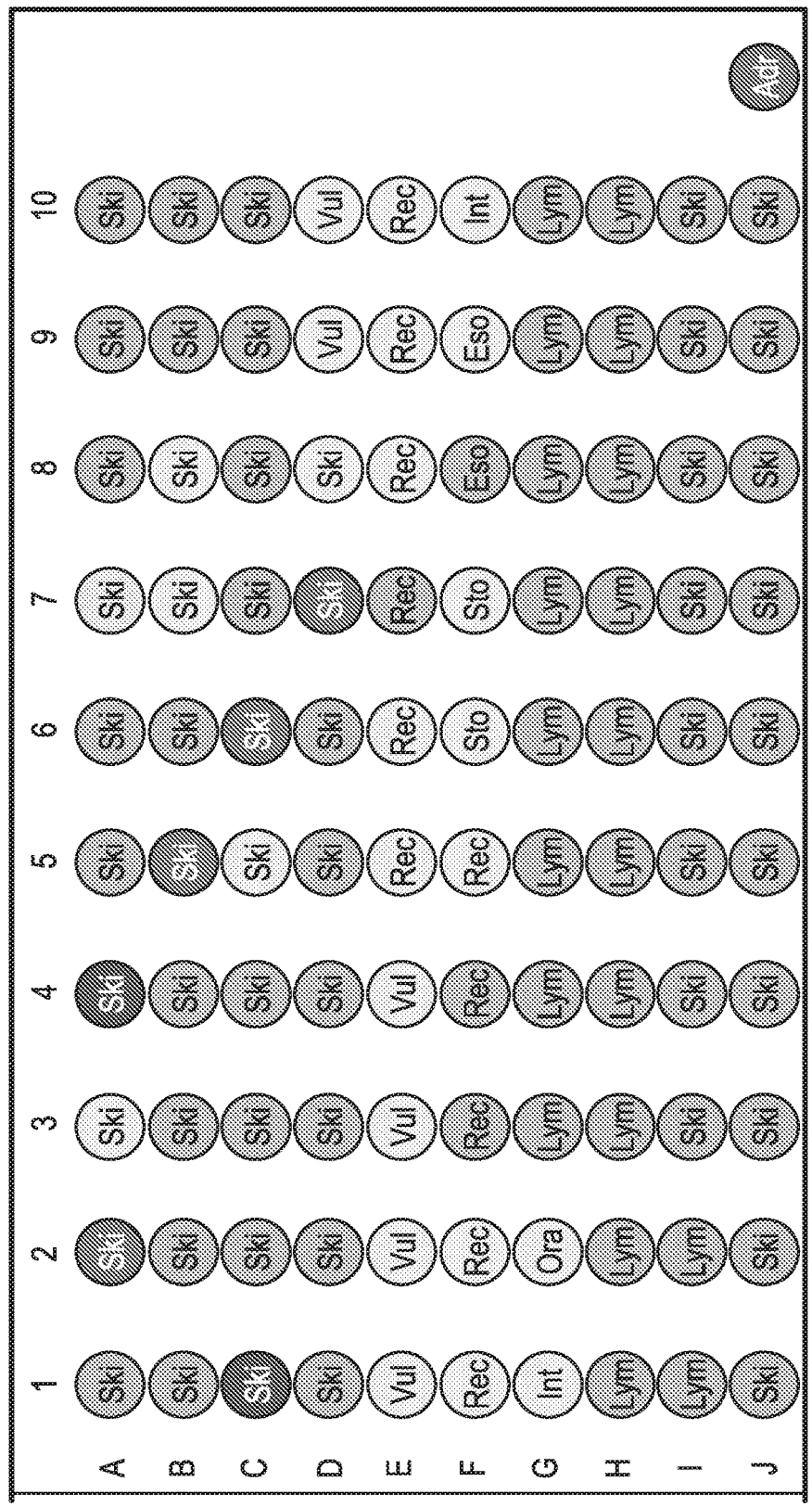

FIG. 23 shows the images depicting the results of CD133 staining of Melanoma Tumor TMA (ME1004c, Biomax, Inc.). TMA was stained with anti-CD133 Panel A: mAb 133-3. Panel B. mAb 47-10, Panel C. Map: Eso—Esophagus, Int—Intestine, Lym—Lymph node, Ora—Oral cavity, Rec—Rectum, Ski—Skin, Sto—Stomach, Vul—Vulva, Color coding employed in the original image and illustrated in the legend was as follows: light blue—benign tumor, dark blue—malignant tumor, the lightest purple—malignant tumor (stage I), light purple—malignant tumor (stage IB), medium purple—malignant tumor (stage II), dark purple—malignant tumor (stage III), the darkest purple—malignant tumor (stage IV), yellow—metastasis.

FIG. 24A, FIG. 24B and FIG. 24C show the specifications of the tumor tissue array ME1004c used in the experiments illustrated in FIG. 22, Biomax, Inc. 2003-2014.

Figure 25:
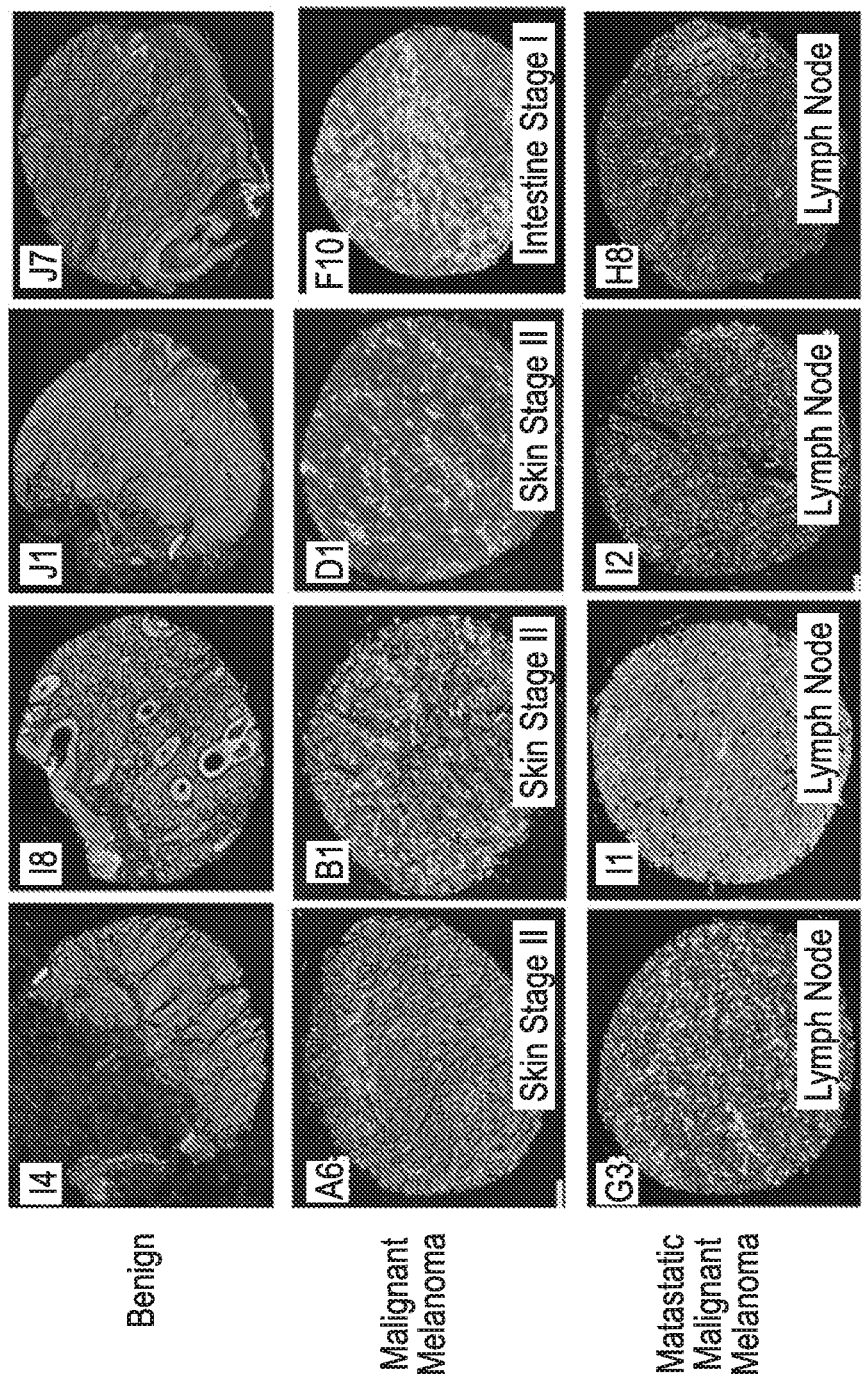

FIG. 25 shows the images depicting the results of CD133 staining of selected tumor cores of Melanoma Tumor TMA (ME1004c, Biomax) stained with CD133 (mAb 133-3).

Figure 26:
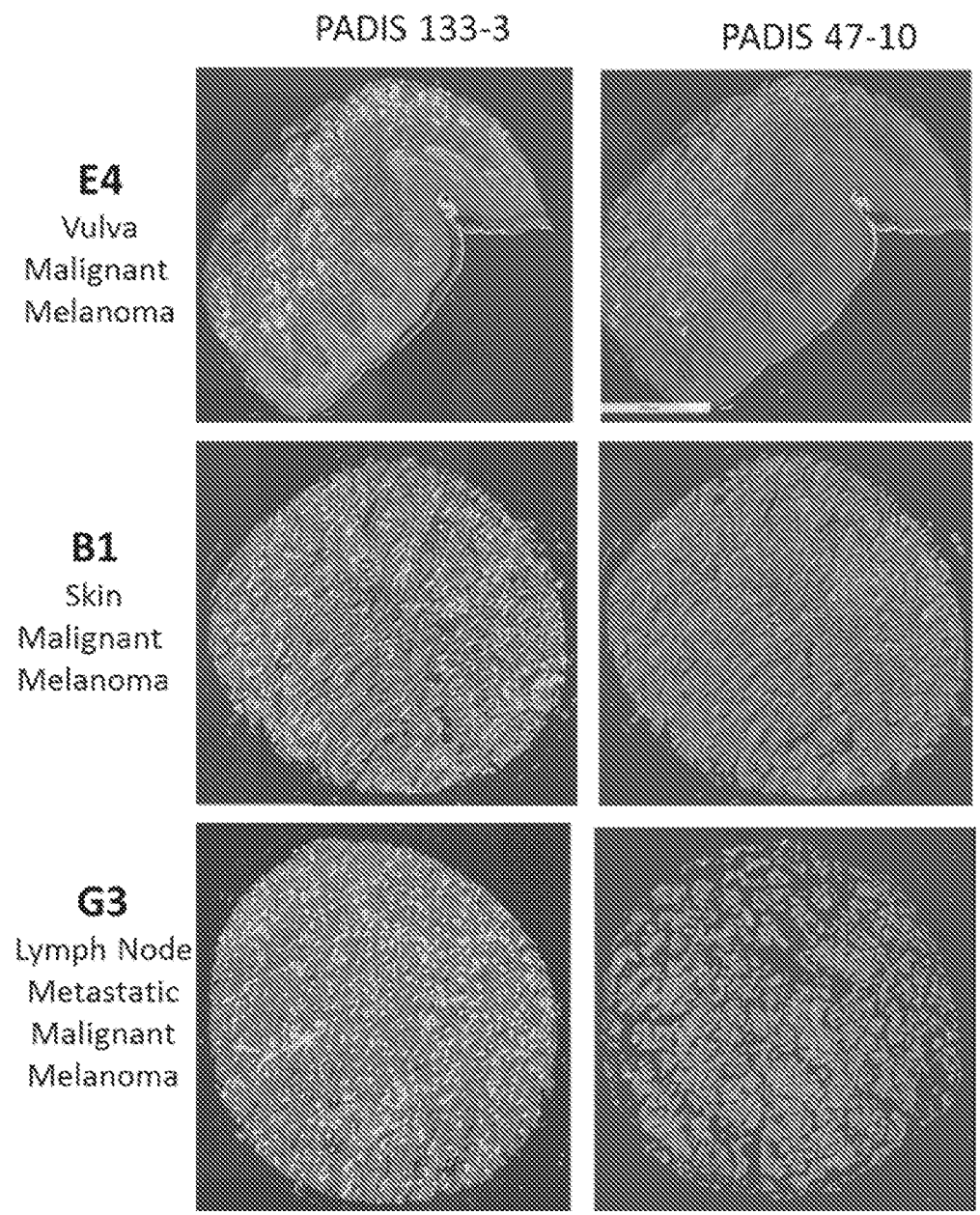

FIG. 26 shows the images depicting the results of CD133 staining of selected tumor cores of Melanoma Tumor TMA (ME1004c, Biomax) stained with mAbs133-3 and 47-10, as indicated in the figure.

Figure 27:
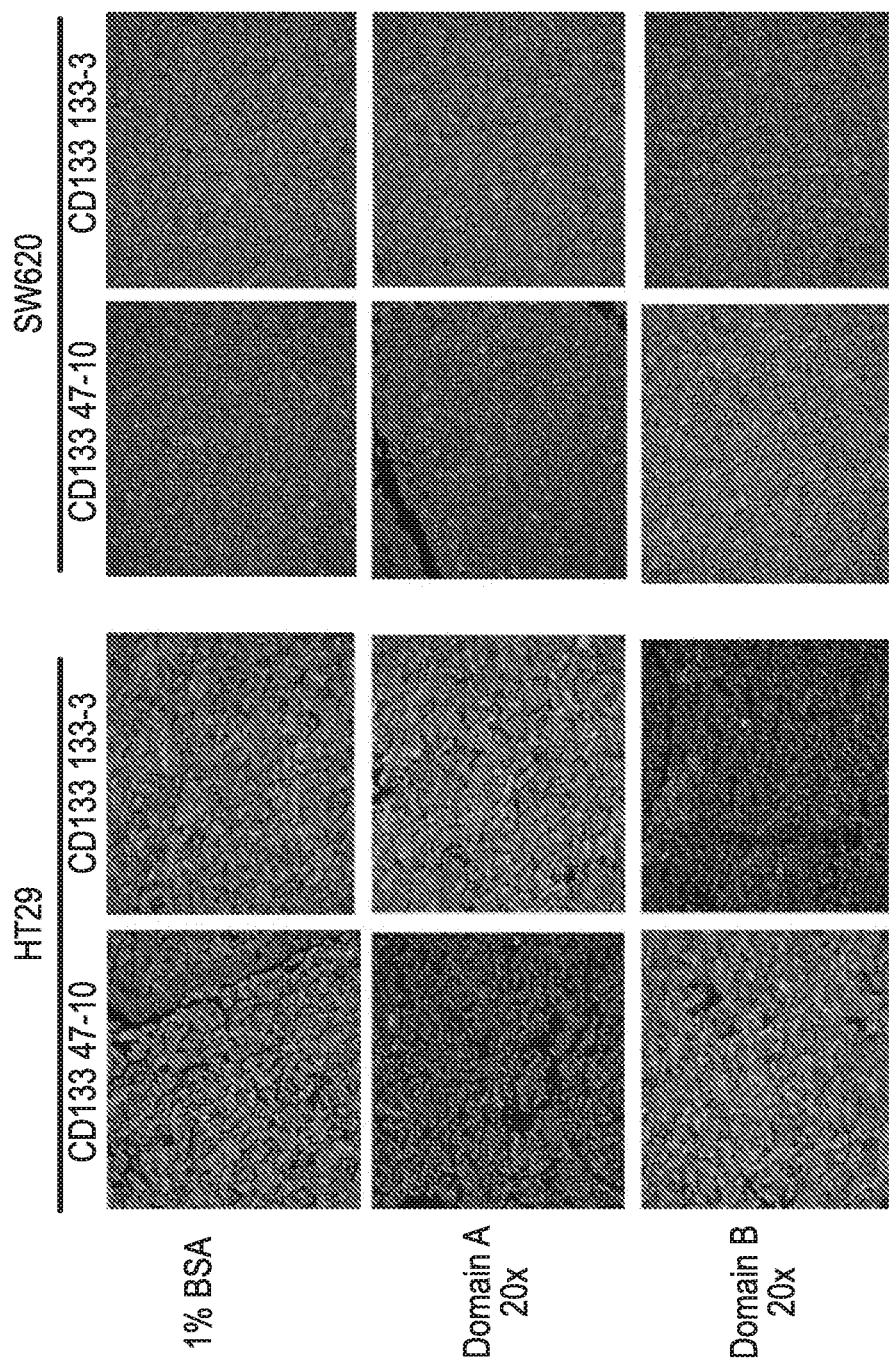

FIG. 27 shows colored images depicting the results of peptide blocking of CD133 staining of FFPE HT-29 and SW620 cell pellets stained with mAbs 133-3 and 47-10, as indicated in the figure. Monoclonal antibodies were pre incubated overnight with peptide SEQ ID NO:17 conjugated to BSA or SEQ ID NO:18 conjugated to BSA or 1% BSA. The peptides were used at a 20-fold molar excess to mAbs.

Figure 28:
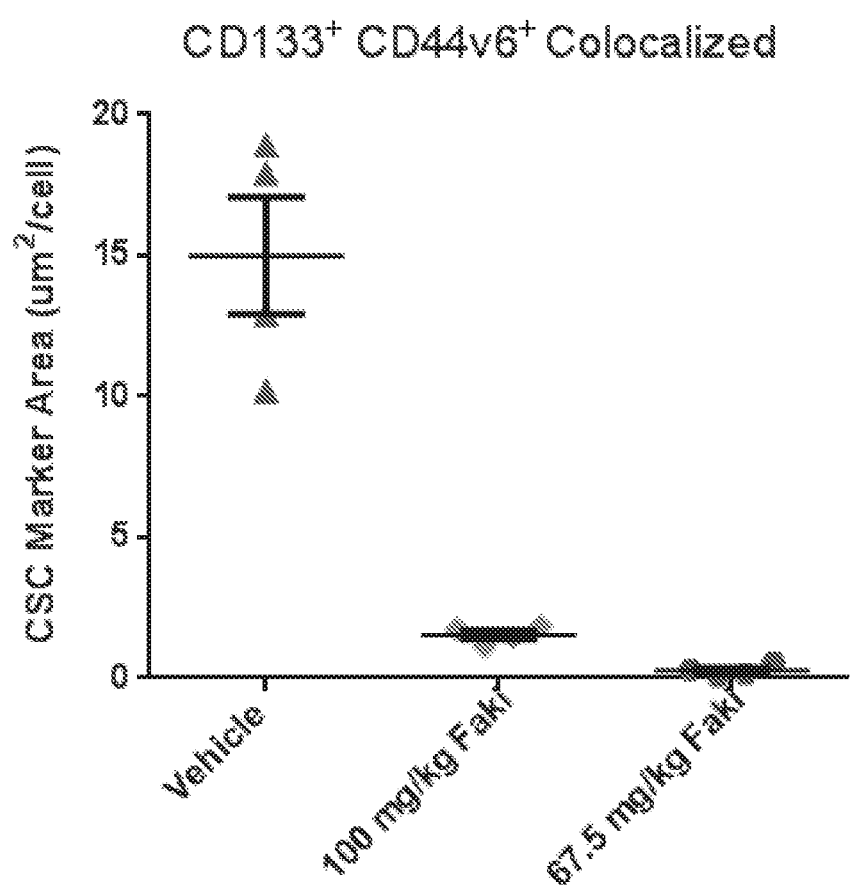

FIG. 28 shows the scatter graphs illustrating the results of quantitation of CD133+CD44v6+ colocalized cells in the slides prepared from Sum149-PT xenograft tumors inoculated subcutaneously into experimental mice treated with vehicle (water, 0.1 ml/10 g body wt), 67.5 mg/kg or 100 mg/kg (42 doses over 21 days) of a FAK inhibitor VS-606 (PO, BID x42), a putative inhibitor of cancer stem cells obtained from Verastem Inc. (Needham, Mass.). The slides were stained with a multiplex of CD44v6 (clone 2F10, R&D Systems) and mAb 47-10, followed by specific secondary antibodies (Goat anti-Rabbit IgG Alexa546 for CD133 and Goat anti-mouse IgG Alexa 488; both secondary antibodies obtained from Thermo-Fisher (Waltham, Mass.)). The results of the staining were quantified. FIG. 28 shows the scatter graphs illustrating the results of quantitation of CD133+CD44v6+ colocalized cells.

Figure 29:
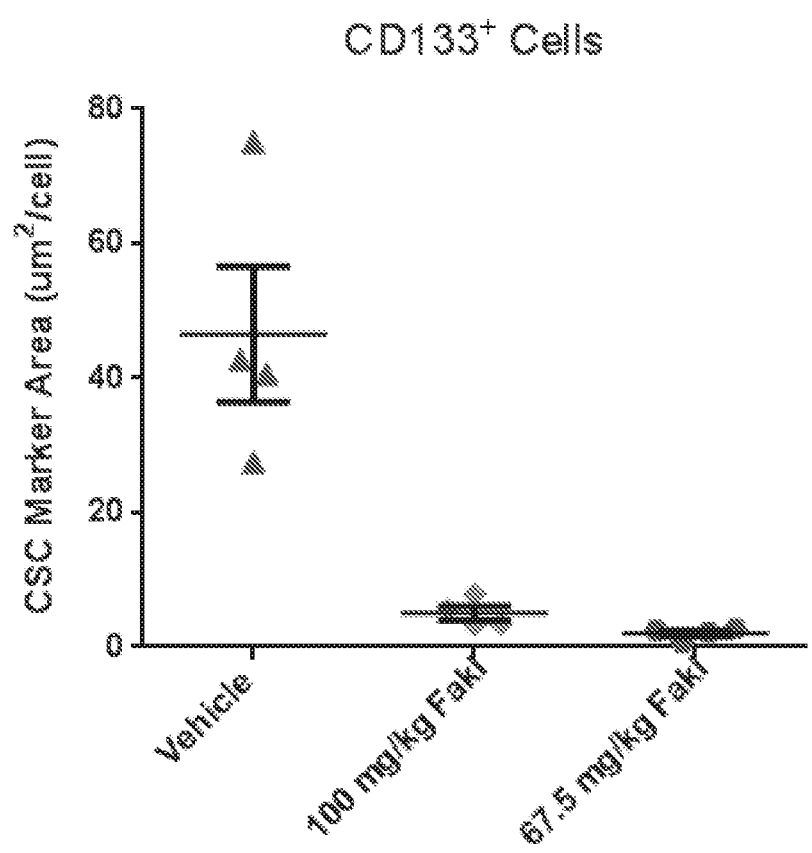

FIG. 29 shows the scatter graphs illustrating the results of quantitation of CD133+ cells in the slides prepared from Sum149-PT xenograft tumors inoculated subcutaneously into experimental mice treated with vehicle (water, 0.1 ml/10 g body wt), 67.5 mg/kg or 100 mg/kg (42 doses over 21 days) of a FAK inhibitor VS-606 (PO, BID x42). The slides were stained with mAb 47-10, followed by s Goat anti-Rabbit IgG Alexa546 secondary antibody obtained from Thermo-Fischer. The results of the staining were quantified.

DESCRIPTION

Embodiments of the present invention provide novel anti-CD133 monoclonal antibodies having advantageous properties, products, compositions and kits comprising the monoclonal antibodies, methods (processes) of making the monoclonal antibodies and related compositions, as well as methods of using the monoclonal antibodies in analytical, diagnostic and therapeutic applications.

Anti-CD133 Monoclonal Antibodies

Embodiments of the present invention include anti-CD133 monoclonal antibodies described in this document, as well as various modifications and variations of these monoclonal antibodies. Anti-CD133 monoclonal antibodies according to some embodiments of the present invention were obtained by carefully selecting potentially immunogenic amino acid sequences from the regions of CD133 extracellular domains that are devoid of glycosylation sites, using the selected sequences to generate immunogenic peptides, using the immunogenic peptides to generate monoclonal antibodies via a hybridoma technology and screening the resulting monoclonal antibodies for specific binding of the polypeptides containing the above immunogenic amino acid sequences. Monoclonal antibodies with the desired binding properties were thus selected. The selected monoclonal antibodies were further tested for specificity as well as for suitability for analytical assays. The antibodies with acceptable specificity and suitability and capable of detecting both glycosylated and unglycosylated forms of CD133 were cloned, sequenced and produced by recombinant technology. The resulting monoclonal antibodies detect both unglycosylated CD133 protein and a range of its glycosylated forms and are suitable for various analytical procedures, including immunofluorescence assays, Western blotting and ELISA. The monoclonal antibodies may be useful in a wide range of analytical, diagnostic and therapeutic applications, in which specific binding of a monoclonal antibody to CD133 polypeptides is desired.

Antibodies

As used herein, the term "antibody" encompasses whole immunoglobulin (i.e., an intact antibody) of any class, including natural, natural-based, modified and non-natural antibodies, as well as their fragments. Natural antibodies are very large, complex polypeptide molecules (molecular weight (MW) of about 150,000, which about 1320 amino acids) with intricate internal structure. Natural antibodies are usually heterotetrameric glycoproteins. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The prevalence of the isotopes differs among the species. For example, rabbit has only one IgG subclass, while mouse has IgG1, IgG2a, IgG2b, IgG2c, IgG3 subclasses. Most of rabbit research antibodies are of IgG isotope. They possess a number of advantages, in comparison to other antibody types. Some of the advantages are more diverse epitope recognition, improved immune response to small-size epitopes, high specificity and affinity, and greatly improved response to mouse antigens.

The heavy chain constant domains that correspond to the different classes of immunoglobulins are called alpha, delta, epsilon, gamma, and mu, respectively. The term "variable" may be used in reference to antibodies to describe certain portions of their variable regions that differ in sequence among antibodies and are used in the binding and specificity of each particular antibody for its particular antigen. The variability is not usually evenly distributed through the variable domains of antibodies but typically concentrated in the segments called complementarity determining regions (CDRs) or hypervariable regions, both in the light chain and the heavy chain variable domains. The other, more highly conserved portions of the variable domains, are called the framework (FR). Within each light or heavy chain variable region, there are three CDRs averaging 10 amino acids in length. The "Kabat Numbering Scheme" is a scheme for the numbering of amino acid residues in antibodies based upon variable regions. The scheme employs the so-called "Kabat numbers" to denote amino acid residues and is useful when comparing these variable regions between antibodies. The six CDRs in an antibody variable domain (three from the light chain and three from the heavy chain) fold up together in 3-D space to form the actual antibody binding site which locks onto the target epitope within the antigen.

The term "antibody binding site" and the related terms may be used herein to describe a polypeptide structure capable of specifically binding an "epitope—the region of its antigen to which the antibody binding site binds. As used herein, the terms "specific binding," "selective binding" or related terms refer to a binding reaction in which, under designated conditions, a molecule or a composition containing an antibody binding site binds to its epitope and does not bind in a significant amount to other potential binding partners. The absence of binding in a significant amount is considered to be binding that is less than 1.5 times background (i.e., the level of non-specific binding or slightly above non-specific binding levels). For example, the anti-CD133 monoclonal antibodies of the present invention specifically bind to their respective CD133 epitopes. Antibody binding site may also be described in reference to amino acid sequences of the polypeptides within the binding site, for example, CDR amino acid sequences, or in terms of the nucleic acid sequences encoding the amino acid sequences.

Monoclonal Antibodies

The antibodies of the embodiments of the present invention are monoclonal. The terms "monoclonal antibody," "monoclonal antibodies." "mAb," "mAbs" and other related terms may be used in this document to refer to a substantially homogenous population of antibodies or to an antibody obtained from a substantially homogeneous population of antibodies. The antigen binding sites of the individual antibodies comprising the population are comprised of polypeptide regions similar (although not necessarily identical) in sequence. The nature of the monoclonal antibodies is easier understood in comparison to polyclonal antibodies. In laboratory conditions, polyclonal antibodies are typically produced by injecting an animal (such as a rodent, rabbit or goat) with an immunizing agent (which may be referred to as immunogen or antigen), which elicits animal's immune system lymphocytes to produce antibodies to the antigen, and extracting the antibody-containing serum from the animal. The extracted serum contains a population of immunoglobulin molecules produced by different B-cell lineages. This population is typically referred to as "polyclonal antibodies." Polyclonal antibodies react against the same antigen, but may bind to different epitopes within the antigen. Polyclonal antibodies have binding sites with different sequences and structures, as well as varying properties, such as affinity or specificity. In contrast, a population of monoclonal antibodies binds to the same epitope on an antigen and are understood to have antigen binding sites with similar sequence and structure.

Monoclonal antibodies may be prepared in the laboratory conditions using hybridoma methods. First, as during the production of polyclonal antibodies, a host animal, such as a mouse or a rabbit, may be administered an antigen. After the host animal mounts an immune response to the antigen, spleen cells or lymph node cells are extracted from the animal. If a human is used as a "host animal," peripheral blood lymphocyte ("PBL") cells are typically obtained. Alternatively, the lymphocytes may be immunized in vitro. The cells are then fused with an immortalized cell line using a suitable fusing agent, such as polyethylene glycol, to form a hybridoma cell line. Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. For hybridoma, immortalized cell lines are useful that fuse efficiently, support stable high level expression of antibody by the selected antibody-producing cells, and are sensitive to a medium such as HAT medium. One example are immortalized cell lines are murine myeloma cell lines. The culture medium in which the hybridoma cells are cultured can then be assayed for the presence of monoclonal antibodies by various assays, such as immunoprecipitation or in vitro binding assays, such as radioimmunoassay (RIA) or enzyme-linked immunoabsorbent assay (ELISA). After the desired hybridoma cells are identified, their clones may be subcloned by limiting dilution or FACS sorting procedures and grown by standard methods. Suitable culture media for this purpose include, for example, Dulbecco's Modified Eagle Medium and RPMI-1640 medium. Alternatively, the hybridoma cells may be grown in vivo as ascites in a mammal. The monoclonal antibodies secreted by the subclones may be isolated or purified from the culture medium or ascites fluid by conventional immunoglobulin purification procedures.

Monoclonal antibodies may also be produced by recombinant DNA methods. For example, phage display/yeast display libraries are used for rapid cloning of immunoglobulin segments to create libraries of antibodies, from which antibody binding sites with desired properties may be selected. In another example, DNA encoding the monoclonal antibodies, such as those generated by hybridoma technology, or parts of the monoclonal antibodies, such as their binding sites, is isolated, synthesized and sequenced using conventional procedures from hybridoma cells. DNA encoding the monoclonal antibodies can be isolated and amplified by polymerase chain reaction (PCR) using oligonucleotide probes that are capable of binding specifically to genes encoding the heavy and light chains antibodies. Once isolated, the DNA encoding antibodies or their parts, may be placed into expression vectors, which are then transfected into host cells to synthesize recombinant monoclonal antibodies in the recombinant host cells. Various types of mammalian cell expression systems may be employed, such as, but not limited to, simian COS cells, Chinese hamster ovary (CHO) cells, HEK293 cells, plasmacytoma cells, or myeloma cells, as well as other types of cells that do not otherwise produce immunoglobulin protein. Non-mammalian host cells and/or expression systems can also be employed, one example being insect cells expression systems or avian expression systems. In vitro translation/expression systems may also be used to produce monoclonal antibodies according to the embodiments of the present invention. Some of the compositions and methods related to recombinant production of monoclonal antibodies are discussed in more detail below and included within the scope of the embodiments of the present invention.

Fragments, Variants, Modified and Engineered Antibodies

Monoclonal antibodies according to the embodiment of the present invention can be derived from naturally occurring monoclonal antibodies or artificially produced ("engineered), for example, by recombinant techniques, and encompass fragments, variants and modification of immunoglobulin molecules. In the broadest sense, the term "monoclonal antibody" is used in this document to denote any product, composition or molecule that contains at least one antibody binding cite. For example, monoclonal antibodies encompass chimeric antibodies and hybrid antibodies, with dual or multiple antigen or epitope specificities, and fragments, such as F(ab')2, Fab', Fab, hybrid fragment, single chain variable fragments (scFv) and "third generation" (3G) fragments. Monoclonal antibodies also encompass fusion proteins, single domain and "miniaturized" antibody molecules.

Fragments can be made by known techniques, for example, they can be recombinantly and/or enzymatically produced, and can be screened for specificity and activity according to known methods, such as radioimmunoassays, ELISA, Western blotting or immunofluorescence assays and techniques. Digestion of whole antibody molecules can be employed to produce fragments, particularly, Fab fragments. For example, papain digestion of whole antibody molecules typically produces two identical antigen binding fragments, called Fab fragments, each with a single antigen binding site, and a residual Fc fragment. In another example, pepsin treatment yields a fragment, called the $F(ab')_2$ fragment, that has two antigen binding sites. The Fab fragments produced in the antibody digestion also contain the constant domains of the light chain and the first constant domain of the heavy chain. Fab' fragments differ from Fab fragments by the addition of a few residues at the carboxy-terminus of the heavy chain domain, including one or more cysteines from the antibody hinge region. $F(ab')_2$ fragments are bivalent fragments comprising two Fab' fragments, which may linked by a disulfide bridge at the hinge region. Fab'-SH is the designation that may be used Fab' in which the cysteine residue(s) of the constant domains bear a free thiol group. Antibody fragments may be produced as pairs of Fab' fragments with hinge cysteines between them. Other chemical couplings of antibody fragments may also be employed.

Various modifications of monoclonal antibodies may be produced, for example, by recombinant DNA techniques. As used herein, a "recombinant" or "recombinant produced" monoclonal antibody is a product, composition or molecule containing an antibody binding site produced with the help of recombinant DNA techniques. As used herein, the terms "recombinant" or "recombinant produced" encompass antibodies for which the genes have been constructed and/or placed in an unnatural environment, for example for expression, with the help of recombinant DNA techniques. In one example, the DNA encoding a monoclonal antibody may be modified, for example, by joining to the all or part of immunoglobulin coding sequence all or part of the coding sequence for a non-immunoglobulin polypeptide. Such a non-immunoglobulin polypeptide, which is included within the scope of the "monoclonal antibodies" of the present invention, can be substituted for the constant domains of a monoclonal antibody. In another example, a chimeric antibody may be produced. A chimeric antibody, which also included within the scope of the monoclonal antibodies of the present invention, is an antibody in which parts of antibody molecules of different origins are combined. For example, the variable region of a non-human antibody may be combined with the constant region of a human antibody to produce a chimeric antibody. Such chimeric antibodies retain the binding specificity of the non-human antibody, while being about two-thirds human.

One more example of an "engineered" antibody is a humanized antibody, in which the CDRs from a non-human antibody ("donor antibody," which can be, for example, mouse, rat, hamster or other mammalian species) are grafted onto a human antibody ("acceptor antibody"). Humanized antibodies can also be made with less than the complete CDRs from a donor antibody. Thus, a humanized antibody is an antibody having CDRs from a donor antibody and variable region framework and constant regions from a human antibody. The term "framework" or "framework region" in the context of antibody structure generally denotes amino acid sequences interposed between CDRs in a heavy or light variable region of an antibody. Framework includes variable light and variable heavy framework regions. The framework regions serve to hold the CDRs in an appropriate orientation. For example, a humanized antibody may contain a light chain comprising three CDRs (or their portions) from a non-human donor antibody, a variable region framework from a human antibody, a human constant region, and a heavy chain comprising three CDRs (or their portions) from a donor antibody, a variable region framework from a human antibody and a human constant region. Various approaches may be used to retain high binding affinity of humanized antibodies to their antigens. In the first structural element, the framework of the heavy chain variable region of the humanized antibody is chosen to have maximal sequence identity (between 65% and 95%) with the framework of the heavy chain variable region of the donor antibody, by suitably selecting the acceptor antibody from among the many known human antibodies. Sequence identity is determined when antibody sequences being compared are aligned according to the Kabat numbering convention. In the second structural element, in constructing the humanized antibody, selected amino acids in the framework of the human acceptor antibody (outside the CDRs) are replaced with corresponding amino acids from the donor antibody, in accordance with specified rules. Specifically, the amino acids to be replaced in the framework are chosen on the basis of their ability to interact with the CDRs. For example, the replaced amino acids can be adjacent to a CDR in the donor antibody sequence or within 4-6 angstroms of a CDR in the humanized antibody as measured in three-dimensional space.

Embodiments of the present invention encompass "human-like" monoclonal antibodies, meaning monoclonal antibodies in which a substantial portion of the amino acid sequence of one or both chains (for example, about 50% or more) originates from human immunoglobulin genes. Human-like antibodies include, but are not limited to chimeric and humanized and human antibodies. Other types of genetically engineered antibodies that may be human-like include human antibodies using phage display methods or produced using transgenic animals. Embodiments of the present invention also use "reduced-immunogenicity" antibodies, meaning the heterologous (originating form a species other than the intended recipient) antibodies which, upon administration to a recipient, have reduced immunogenicity. Such antibodies encompass chimeric, humanized and human antibodies as well as antibodies made by replacing specific amino acids in mouse antibodies that may contribute to B- or T-cell epitopes, for example exposed.

Monoclonal antibodies according to the embodiments of the present invention may contain a label. The term "label" encompasses any detectable tag that can be attached directly (for example, a fluorescent molecule integrated into a polypeptide) or indirectly, by way of binding to a primary antibody a secondary antibody with an integrated label or tag. The term "label" or "tag" also encompasses an epitope recognized by another (secondary) antibody or protein that can be conjugated to a label or tag. Detectable label may be an enzymatic label (such as but not limited to horse radish peroxidase (HRP) or alkaline phosphatase (AP)), a radio-opaque substance, a radiolabel, a fluorescent label, a nanoparticle label or a magnetic label, a hapten, or a oligonucleotide or polynucleotide label. Detectable label may be a gamma-emitter, beta-emitter, alpha-emitter, gamma-emitter, positron-emitter, X-ray-emitter or fluorescence-emitter. Suitable fluorescent compounds include fluorescein sodium, fluorescein isothiocyanate, phycoerythrin (PE), Allophycocyanin (APC), Alexa Fluor® family of dyes (such as, Alexa Fluor® 350; Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680 or Alexa Fluor® 750), Cy® family of dyes (such as Cy® 3 or Cy® 5), BODIPY® FL, Coumarin, Oregon Green®, Pacific Blue®, Pacific Green®, Pacific Orange®, tetramethylrhodamine (TRITC), Texas Red®, Q-Dot® probes (such as Qdot® 525. Qdot® 565. Qdot® 605. Qdot® 655, Qdot® 705, or Qdot® 800), Expressed fluorescent proteins (such as Cyan Fluorescent Protein (CFP), Green Fluorescent Protein (GFP). Or Red Fluorescent Protein (RFP), haptens (such as biotin or DIG). Monoclonal antibodies according to the embodiments of the present invention can also be conjugated or fused to bioactive substances, drugs and radioactive or toxic moieties, such as diphtheria or ricin toxin.

Properties of Anti-CD133 Monoclonal Antibodies

Binding Properties

Monoclonal antibodies according to the embodiments of the present invention have one or more of the more structural and/or functional properties described in this document. One of the properties used to describe the monoclonal antibodies according to the embodiments of the present invention is their ability to bind defined polypeptide "antigens." Another property is the structure of the monoclonal antibodies or their parts, for example, amino acid sequence of the one or more polypeptides in an antibody binding site. Nucleotide sequences encoding the amino acid sequence of the monoclonal antibodies or their parts can also be employed.

For example, the monoclonal antibodies according to the embodiments of the present invention can be described in reference to their binding properties—as capable of binding CD133 protein, its fragments and/or variants, including at least some orthologs. The term "CD133 protein," which can also be referred to as prominin-1, PROM1, PROML1 prominin, AC133, CORD12, MCDR2, RP41, STGD4 refers to a five-transmembrane domain glycoprotein encoded by PROM1 gene. The term "CD133 protein" includes orthologs from different species, including, but not limited to, rat, mouse, gorilla, chimpanzee, rhesus monkey, cotton-top tamarin, dog and human. The term also includes various variants and isoforms, such as splice variants and isoforms, postranslationally modified (form example, glycosylated) variants and isoforms, as well as mutants and homologs. CD133 protein may be described by using an amino acid sequence of human CD133 protein (SEQ ID NO:1) and homologous sequences, such as SEQ ID NOs 2-8, or sequences with an extent of homology (as defined further in this document) of at least 60%, at least 65%, at least 70%, at least 75%, at least 80%, at least 85%, at least 90%, at least 95%, at least 98% or at least 99%.

As discussed elsewhere in this documents, anti-CD133 monoclonal antibodies of the present invention were obtained by using immunogenic polypeptides having amino acid sequences from the regions of CD133 extracellular domains A and B (SEQ ID NO:17—domain A immunogenic polypeptide sequence ("polypeptide A"); SEQ ID NO: 18—domain B immunogenic polypeptide ("polypeptide B")

sequence and screened for specific binding using polypeptides A and B and recombinantly expressed CD133 domain A and B polypeptides (SEQ ID NO:19—recombinant domain A polypeptide; SEQ ID NO:20—recombinant domain B polypeptide). Monoclonal antibodies according to some embodiments of the present invention specifically bind to domain A polypeptides SEQ ID NOs 17 and 19) but not to domain B polypeptides (SEQ ID NOs 18 and 20), or, alternatively, to domain B but not to domain A polypeptides. Accordingly, monoclonal antibodies specific for domain A polypeptides are capable of specifically binding polypeptides comprising SEQ ID NO:17 and/or 19, or their variants or homologues. Monoclonal antibodies specific for domain B polypeptides are capable of specifically binding polypeptides comprising SEQ ID NO:18 and/or 20, or their variants or homologues. Binding of the monoclonal antibodies according to the embodiments of the present invention to their polypeptides may be described in terms of binding affinity. For example, monoclonal antibodies of the present invention typically have a binding affinity ($K_a$) for their respective CD133 polypeptides of at least $10^7$ $M^{-1}$, at least $10^8$ $M^{-1}$, at least $10^9$ $M^{-1}$, or at least $10^{10}$ $M^{-1}$.

Structural Properties—Sequences

Monoclonal antibodies according to the embodiments of the present invention can also be described using binding site antibody amino acid sequences or nucleic acids encoding such amino acid sequences. One exemplary embodiment is a monoclonal antibody having an antibody binding site containing SEQ ID NO:9 (or its homologues or variants) in its heavy chain and SEQ ID NO:11 (or its homologues or variants) in its light chain. One more exemplary embodiment is a monoclonal antibody having an antibody binding site containing an amino acid sequence encoded by SEQ ID NO: 10 (or its homologues or variants) in its heavy chain and an amino acid sequence encoded by SEQ ID NO: 12 (or its homologues or variants) in its light chain. Another exemplary embodiment is a monoclonal antibody having an antibody binding site containing SEQ ID NO: 13 (or its homologues or variants) in its heavy chain and SEQ ID NO:15 (or its homologues or variants) in its light chain. Yet another exemplary embodiment is a monoclonal antibody having an antibody binding site containing an amino acid sequence encoded by SEQ ID NO:14 (or its homologues or variants) in its heavy chain and an amino acid sequence encoded by SEQ ID NO:16 (or its homologues or variants) in its light chain. One more exemplary is a monoclonal antibody having an antibody binding site containing one or more amino acid sequences corresponding to H1, H2 and H3 CDRs contained within SEQ ID NO:9 (or its homologues or variants) in its heavy chain and containing one or more amino acid sequences corresponding to L1, L2 and L3 CDRs contained within SEQ ID NO: 11 (or its homologues or variants) in its light chain. Yet another exemplary is a monoclonal antibody having an antibody binding site containing one or more amino acid sequences corresponding to H1, H2 and H3 CDRs contained within SEQ ID NO: 13 (or its homologues or variants) in its heavy chain and containing one or more amino acid sequences corresponding to L1, L2 and L3 CDRs contained within SEQ ID NO: 15 (or its homologues or variants) in its light chain. Homologues or variants discussed above may refer to variants or homologues of at least 60%, at least 65%, at least 70%, at least 75%, at least 80%, at least 85%, at least 90%, at least 95%, at least 98% or at least 99% degree of homology.

Variations and Modifications of Nucleic Acids and Polypeptides; Sequence Homology Embodiments of the present invention encompass homologues, variants, isoforms, fragments, mutants, modified forms and other variations of the polypeptides and nucleic acid sequences described in this document. The term "homologous," "homologues" and other related terms used in this document in reference to various amino acid and nucleic acid sequences, are intended to describe a degree of sequence similarity among protein sequences or among and nucleic acid sequences, calculated according to an accepted procedure. Homologous sequences may be at least 60%, 65%, 70%, 75%, 80%, 85%, 90%, 91%, 92%, 93%, 94%, 95%, 96%, 97%, 98% 99% or 100% homologous. As used herein, "percent homology" of two amino acid sequences or of two nucleic acid sequences is determined using the algorithm of Karlin and Altschul, which is incorporated into the NBLAST and XBLAST programs, available for public use through the website of the National Institutes of Health (U.S.A.). To obtain gapped alignments for comparison purposes, Gapped BLAST is utilized. When utilizing BLAST and Gapped BLAST programs, the default parameters of the respective programs (e.g., XBLAST and NBLAST) are used. "Percent homology" may be used in this document to describe fragments, variants or isoforms of amino acids and nucleic acid sequences, but other ways of describing fragments, variants or isoforms may be employed alternatively to or in conjunction with homology.

Fragments of a polypeptide can include any portion of a polypeptide of at least 3, 5, 8, 10, 15, 20, 25, 30, 35, 40, 45 amino acids. It is to be appreciated, for example, that some epitopes can contain only three amino acids. Furthermore, since epitopes (antigens) to which the monoclonal antibodies bind can involve residues that are not adjacent in peptide sequence, but are next to each other in three-dimensional structure, it is possible to achieve a special configuration of an epitope using smaller fragments of a polypeptide sequence included discontinuously within a longer sequence.

Variants may result from sequence variations, such as amino acid substitutions, deletions, and insertions, as well as post-translational modifications. Variations in post-translational modifications can include variations in the type or amount of carbohydrate moieties of the protein core or any fragment or derivative thereof. Variations in amino acid sequence may arise naturally as allelic variations (such as due to genetic polymorphism) or may be produced by human intervention (such as by mutagenesis of cloned DNA sequences), the examples being induced point, deletion, insertion and substitution mutants. Variations in a nucleic acid sequence may result in changes in the amino acid sequence, provide silent mutations, modify a restriction site, or provide other specific mutations.

The term "mutation" or "mutated sequence." when used in reference to nucleotide or amino acid or nucleotide sequence can be used interchangeably with the terms "variant," "allelic variant," "variance," or "polymorphism." Amino acid sequence modifications include substitutions, insertions or deletions. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Amino acid substitutions are typically of single residues but may include multiple substitutions at different positions; insertions usually will be on the order of about from 1 to 10 amino acid residues but can be more; and deletions will range about from 1 to 30 residues, but can be more. Amino acid substitutions may be characterized as "conservative," meaning substitution for an amino acid with similar properties. Some examples of conservative substitutions are shown in Table 1, below. Conservative amino acid substitutions in monoclonal antibodies may have substantially no effect on antigen binding or other immunoglobulin functions. See, for example, Harlow & Lane, "Antibodies, A Laboratory Manual, Cold Spring Harbor Publications," New York (1988). A variant or an isoform can contain one or more of substitutions (including, for example, conservative amino acid substitutions, such as 1-5, 1-10, 1-20, 1-50 or more conservative amino acid substitutions), deletions, insertions.

An isoform or a variant can also be a result of post-translational modifications, derivatizations or lack thereof. For example, variants may arise as a result of differences in glycosylation, such as N- and O-glycosylation. Glutaminyl and asparaginyl residues are frequently post-translationally deamidated to the corresponding glutamyl and asparyl residues. Alternatively, these residues may be deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (acetylation of the N-terminal amine and, in some instances, amidation of the C-terminal carboxyl. Modifications can also include modifications in glycosylation.

TABLE 1

Conservative amino acid substitutions

| Original residue | Exemplary Residue Substitutions |
|---|---|
| Ala | Ser |
| Arg | Lys |
| Asn | Gln |
| Asp | Glu |
| Cys | Ser |
| Gln | Asn |
| Glu | Asp |
| Gly | Pro |
| His | Gln |
| Ile | Leu; Val |
| Leu | Ile; Val |
| Lys | Arg; Gln |
| Met | Leu, Ile |
| Phe | Met; Leu; Tyr |
| Ser | Thr |
| Thr | Ser |
| Trp | Tyr |
| Tyr | Trp; Phe |
| Val | Ile; Leu |

Methods of Making Anti-CD133 Monoclonal Antibodies and Related Compositions; Molecules, Products and Kits Methods of making monoclonal antibodies are included within the scope of the embodiments of the present invention. Monoclonal antibodies can be produced by processes comprising a step of administering an immunogenic composition containing at least one of immunogenic polypeptides (described elsewhere in this document) to subjects, cells or tissues, to induce antibody production in the subjects, cells or tissues. Administration of the immunogenic composition induces production of antibodies in the subjects, cells or tissues. Thus, antibody-producing subjects, cells or tissues are provided. Methods of making antibodies according to the embodiments of the present invention can include one or more steps typically employed in hybridoma technology, such as isolating antibody-producing cells from the subject, using the antibody-producing cells to generate a hybridoma cell culture and isolating an individual antibody-producing cell from the hybridoma cell culture. Antibody-producing cells may be expanded in culture and used to generate monoclonal antibodies.

Anti-CD133 antibody production processes according to the embodiments of the present invention may include one or more screening steps, methods or processes. Such screening steps, methods and processes are included within the scope of the present invention. "Screening," which may also be referred to as "analysis," "characterization," "testing" or by other related terms The binding properties of thus generated monoclonal antibodies may be characterized or tested during the screening, which may involve the steps of contacting monoclonal antibodies with a screening composition comprising the at least one of immunogenic polypeptides under conditions of an assay intended to detect binding of the antibody to the one or more immunogenic polypeptides. The assay, which can be referred to as "screening assay," may be, but is not limited to, an immunoprecipitation assay, a Western blot, an ELISA, a flow cytometry assay, an immunofluorescence assay (IFA), an immunohistochemistry (IHC) assay, a cytospin assay, a fluorescence resonance energy transfer (FRET) assay, or a reverse phase array. More than one screening assay may be employed. A plurality of monoclonal antibodies may be obtained and tested by the above processes. Based on the results of the screening monoclonal antibodies with desired binding properties, such as binding strength, specificity or both, may be selected for further processes and uses. Desired binding properties may be binding strength and/or specificity of binding of an antibody to a screening compositions. For example, a screening may reveal that an antibody exceeds a certain predetermined threshold value characterizing binding strength or specificity, or that the antibody's characteristics are superior in comparison to other screened antibodies, which case the antibody may be selected for further processes and uses. Screening may also involve conducting various assays, such as immunofluorescence assays, flow cytometry and the like, that employ antibody-based reagents, using monoclonal antibodies of the present invention.

The methods, processes and steps of producing monoclonal antibodies according to the embodiments of the present invention may include recombinant techniques. The nucleic acid sequences (for example, cDNA sequences and genomic DNA sequences) encoding antibody binding site or amino acid sequences of the selected monoclonal antibodies may be determined. Recombinantly produced monoclonal antibodies containing the antibody binding sites may be generated based on these sequences using appropriate vectors and expression systems, which are described in more detail elsewhere in this document. The methods, processes and steps of producing monoclonal antibodies according to the embodiments of the present invention may include various steps related to analysis and generation of nucleic acid and amino acid sequences and molecules, such as nucleic acid and polypeptide sequencing, amplification (for example, by polymerase chain reaction (PCR)), restriction, nucleic acid and polypeptide synthesis, mass spectroscopy. HPLC, and various other procedures. The methods, processes and steps of producing monoclonal antibodies according to the embodiments of the present invention may include isolation and purification steps, such as dialysis, precipitation, microfiltration, ultrafiltration, protein A or G affinity chromatography, size exclusion chromatography, anion exchange chromatography, hydroxylapatite (hydroxyapatite) chromatography, hydrophobic interactions chromatography, cation exchange chromatography, other forms of affinity chromatograph, gel electrophoresis, HPLC and other techniques and procedures. Compositions, methods and kits related to the antibody production and processes (such compositions, methods and kits for recombinant antibody production, are included within the scopes of the embodiments of the present invention).

Vectors and Cells

Anti-CD133 monoclonal antibodies and other polypeptides described in this documents can be produced with the aid of recombinant technologies. Accordingly, the embodiments of the present invention include expression vectors comprising one or more nucleic acids encoding one or more of the polypeptides described in this documents. In the expression vectors, the encoding nucleic acid is typically operably linked to one or more regulatory sequences. Such useful regulatory sequences include, for example, the early or late promoters, such as promoter sequences of SV40, CMV, vaccinia, polyoma or adenovirus, the lac system, the trp system, the TAC system, the TRC system, the LTR system, the major operator and promoter regions of phage lambda, the control regions of fd coat protein, the promoter for 3-phosphoglycerate kinase or other glycolytic enzymes, the promoters of acid phosphatase (for example, PhoS), the AOX 1 promoter of methylotrophic yeast, the promoters of the yeast a-mating factors, and other sequences known to control the expression of genes of prokaryotic or eukaryotic cells or their viruses.

An expression vector according to the embodiments of the present invention can be designed to produce anti-CD133 monoclonal antibodies or immunogenic polypeptides described in this document. An expression vector can be suitable for expression in eukaryotic cells or prokaryotic cells and thus include DNA molecules which are capable of integration into a prokaryotic or eukaryotic chromosome and subsequent expression. The inserted genes in viral and retroviral vectors usually contain promoters and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Specific regulatory elements can be cloned and used to construct expression vectors that are selectively expressed in specific cell types. For example, the glial fibrillary acetic protein (GFAP) promoter has been used to selectively express genes in cells of glial origin. Expression vectors used in eukaryotic host cells (e.g., yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct. Some examples of the vectors are PUC vectors, pcDNA3 vectors, pEE series vectors, pGL3 vectors or pEGFP vectors. pFUSE-CLIg and pFUSE-CHIg plasmid vectors can be employed, which are designed to change a monoclonal antibody from one isotype to another, thus permitting the generation of a variety of antibodies with the same antigen affinity.

The vectors according to the embodiments of the present invention include viral vectors that transport the nucleic acids encoding monoclonal antibodies and polypeptides described in this document into cells without degradation and include a promoter yielding expression of the nucleic acids in the cells into which it is delivered. Viral vectors are derived from viruses, including retroviruses, such as Adenovirus, Adeno-associated virus, Herpes virus, Vaccinia virus, Polio virus, AIDS virus, neuronal trophic virus, Sindbis virus and other RNA viruses. Also preferred are any viral families that share the properties of these viruses that make them suitable for use as vectors. Retroviruses include Murine Maloney Leukemia virus, MMLV, and retroviruses that express the desirable properties of MMLV as a vector. Some other examples of viral vectors are simian virus 40 (SV40) and baculovirus vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. The necessary functions of the removed early genes are typically supplied by cell lines that have been engineered to express the gene products of the early genes in trans.

Cells including the expression vectors are also included among the embodiments of the present invention. The resulting cells can thus produce anti-CD133 monoclonal antibodies or immunogenic polypeptides described in this document. A cell can be either a eukaryotic or prokaryotic cell, such as strains of *E. coli, Pseudomonas, Bacillus* or *Streptomyces*, fungi such as yeasts (*Saccharomyces*, and methylotrophic yeast such as *Pichia, Candida, Hansenula*, and *Torulopsis*); animal cells, such as CHO, R1. 1, B-W and LM cells, African Green Monkey kidney cells (for example, COS 1, COS 7, BSC1, BSC40, and BMT10), insect cells (for example, Sf9), human cells (such as human embryonic kidney cells, for instance, HEK293) and plant cells in cell or tissue culture.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be co-transformed with polynucleotide sequences encoding the antibody, labeled antibody, or antigen binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. Expression systems, such as plasmids and vectors, can be employed to produce proteins in cells, including higher eukaryotic cells, such as the COS, CHO, HeLa and myeloma cell lines.

Exemplary Process of Making Recombinant Monoclonal Antibodies

In an illustrative example, anti-CD133 monoclonal antibodies according to the embodiments of the present invention, including chimeric and humanized monoclonal antibodies, are recombinantly produced. In one example illustrating the process of using the above-described vectors and cells, a nucleic acid sequence encoding an anti-CD133 monoclonal antibody is introduced into a plasmid or other vector, which is then used to transform living cells. For instance, genes encoding light and heavy chain V regions are synthesized from overlapping oligonucleotides and inserted together with available C regions into expression vectors that provide the necessary regulatory regions, such as promoters, enhancers, poly A sites and other sequences. Expression vectors may be employed, in which a cDNA containing the entire anti-CD133 monoclonal antibody coding sequence, a fragment of the anti-CD133 monoclonal antibody coding sequence, amino acid variations of the anti-CD133 coding sequence, or fusion proteins of the aforementioned, is inserted in the correct orientation in an expression plasmid. In some cases, it may be desirable to express the coding sequence under the control of an inducible or tissue-specific promoter. The expression vectors may then be transfected using various methods, such as lipofection or electroporation, into cells of an appropriate mammalian cell line, thus generating cells expressing the monoclonal antibodies. The cells expressing the antibodies may be selected by appropriate antibiotic selection or other methods and cultured. Larger amounts of antibody may be produced by growing the cells in commercially available bioreactors. Once produced by the antibody-producing cells, anti-CD133 monoclonal antibodies may be purified according to standard procedures, such as dialysis, filtration and chromatography. A step of lysing the cells to isolate the anti-CD133 monoclonal antibody can be included. Thus, a method of making an anti-CD133 monoclonal antibody may contain one or more steps of culturing a cell comprising a vector under conditions permitting expression of the anti-CD133 monoclonal antibody, harvesting the cells and/or harvesting the medium from the cultured cells, and isolating the anti-CD133 monoclonal antibody from the cells and/or the culture medium. Compositions, methods and kits related to the antibody production and processes (such compositions, methods and kits for recombinant antibody production, are included within the scopes of the embodiments of the present invention.

Immunogenic Polypeptides

Among the embodiments of the present invention are immunogenic polypeptides of CD133 that were employed in the production of the monoclonal antibodies according to the embodiments of the present invention, as well their variants and modifications that preserve their immunogenic properties. One example of such an embodiment is an isolated or recombinantly produced polypeptide of SEQ ID NO:17 or 18 or a homologous sequence. Another example is a polypeptide having SEQ ID NO: 17 or 18, or a homologous sequence and also containing additional residues (for example, a lysine residue may be added at the C terminus). One more example is a polypeptide having SEQ ID NO:17 or 18, or a homologous sequence, conjugated to a label or a heterologous polypeptide. Nucleic acid sequences encoding the above polypeptides are also envisioned and included among the embodiments of the present invention.

Molecules, compositions, products, kits including the above immunogenic polypeptides, as well as methods of making and using the above polypeptides, for example, for producing, testing or screening antibodies, inducing immune response in the subjects, cells or tissues are also included within the scope of the present invention. For instance, compositions or molecules containing above polypeptides or nucleic acids may be employed in the methods of producing monoclonal antibodies described in this document as probes in the screening assays. In another example, the compositions or molecules containing above polypeptides or nucleic acids may be administered to subjects, cells or tissues to induce immune response, including production of antibodies.

Methods of Using Monoclonal Antibodies

The processes of using anti-CD133 monoclonal antibodies are included among the embodiments of the present invention. Anti-CD133 monoclonal antibodies can be used in diagnostic, preparative, analytical, prognostic or laboratory methods or assays, as well as in therapeutic methods. For example, the monoclonal antibodies may be used to measure the presence, absence or level of CD133 in samples, such as cells, tissues or organisms, which may be referred to as "subjects." As used throughout the document, the term "subject" and related terms refer to an organism. Subject may be a mammal such as a primate, including a human. The term "subject" can include domesticated animals, such as cats, dogs, etc., livestock (e.g., cattle, horses, pigs, sheep, goats, etc.), and laboratory animals (e.g., mouse, rabbit, rat, guinea pig, etc.). The term "subject" as used may refer to a subject, such as but not limited to a human person, having a cancer, including a solid tumor cancer or a blood cancer. It is to be understood, that a subject having a cancer can be a patient with a known cancer, meaning the cancer that was detected prior to the performance of the embodiments of the methods of the present invention, or a subject with a previously undetected cancer.

Detection Methods

The methods according to the embodiments of the present invention involve binding of the antibody to its epitope. Thus, the processes of using anti-CD133 monoclonal antibodies according to some of the methods described in this document include a step of contacting the anti-CD133 monoclonal antibody (meaning one or more monoclonal antibody) with a sample under conditions that permit binding of the monoclonal antibody with its CD133 epitope. The conditions under which the binding of anti-CD133 monoclonal antibody to its epitope occurs depend on the context of the specific method. The terms "sample" or "samples" is not intended to be limiting and refers to any product, composition, cell, tissue or organism that may contain epitopes of the anti-CD133 monoclonal antibodies described in this document. For example, "sample" may be any cell or tissue sample or extract originating from cells, tissues or subjects, and include samples of human or animal cells or tissues as well as cells of non-human or non-animal origin, including bacterial samples. A sample can be directly obtained from a human or animal organism, or propagated or cultured. Samples can be subject to various treatment, storage or processing procedures before being analyzed according to the methods described in the document. Generally, the terms "sample" or "samples" are not intended to be limited by their source, origin, manner of procurement, treatment, processing, storage or analysis, or any modification. Samples include, but are not limited to samples of human cells and tissues, such as blood samples including circulating stem cells (cSC), cerebrospinal fluid samples, synovial tissue samples, synovial fluid samples, brain tissue samples, blood vessel samples, or tumor samples including circulating tumor cells (CTCs) and circulating cancer stem cells (cCSCs). Blood samples include both blood serum and blood plasma samples. Samples encompass samples of healthy or pathological cells, tissues or structures. Samples can contain or be predominantly composed of cells or tissues, or can be prepared from cells or tissues. Some examples of the samples are solutions, suspensions, supernatants, precipitates (cell precipitates), pellets, cell extracts (for examples, cell lysates), cell extracts, blood or plasma samples, tissue sections and/or including needle biopsies, microscopy slides, including fixed tissues (ex. formalin-fixed, paraffin-embedded (FFPE)) or frozen tissue sections, flow cytometry samples and fixed cell samples. Samples, such as cells and small tissues may be mixed in a slurry of an inert support with or without use of optimal cutting temperature (OCT) or other compounds before freezing, electrophoresis gels and blots (such as those used in Western blotting).

The methods according to the embodiments of the present invention may include a step of detecting the binding of an anti-CD133 monoclonal antibody to its epitope. The detection may be accomplished by detecting epitope-antibody complexes using various types of labels. For example, for various assays, the monoclonal antibodies may be labeled with fluorescent molecules, metals, spin-labeled molecules, nano-particles, enzymes or radioisotopes. The labels are sometimes referred to as "reporter molecules." Anti-CD133 monoclonal antibodies may be directly labeled, meaning that the labels can be directly attached (conjugated to the antibodies) or indirectly (non-covalently) labeled, meaning that antibody-binding molecules containing the labels may be employed. For example, labeled secondary antibodies or their fragments capable of binding anti-CD133 monoclonal antibodies may be used. Some examples of antibody labels and procedures used in labeling are described, for example, in "Guide to Antibody Labeling and Detection," Innova Biosciences (2010), Cambridge (UK), Buchwalow & Bocker "Immunohistochemistry: Basics and Methods" Springer-Verlag Berlin Heidelberg (2010) (see, for example, Chapter 2 "Antibody Labeling and the Choice of a Label," pages, 9-17). Detection of the labels, which includes qualitative and quantitative detection, is accomplished by various methods, depending on the label, the method in which it is used, and the result desired.

For example, in some of the embodiments of the methods described in this documents, the binding of anti-CD133 monoclonal antibodies to their epitopes in cell and tissue samples may be visually detected, such as in the slides examined or imaged under the microscope, by using either a direct (covalently attached) fluorescent label or fluorescently labeled secondary antibodies. In another example, fluorescence emitted by labeled anti-CD133 monoclonal antibodies or by the secondary antibodies is quantitatively detected by registering light emitted by the sample at a particular wavelength. One or more monoclonal antibodies may be employed. In some exemplary methods, two monoclonal antibodies binding to different CD133 epitopes (i.e., not competing for binding) may be simultaneously employed, for example, in a "sandwich" assays, such as ELISA. Anti-CD133 monoclonal antibodies according to the embodiments of the present invention and may be provided in the form of kits with all the necessary reagents to perform the assay for CD133 presence, absence or level.

Monoclonal anti-CD133 antibodies according to the embodiments of the present invention detect a range of CD133 variants and isoforms, including unglycosylated and a range of glycosylated variants, and are useful for various analytical procedures and protocols, including pharmacodynamic immunoassays, immunofluorescence assays, Western blotting, ELISA, flow cytometry and immunoprecipitation. The methods described in this document can involve detecting the total level of all CD133 variants or isoforms, or the level of some of them. A method can contain a step of detecting a level of CD133 in a sample and comparing it to a control level. Control levels can be used to establish a threshold value. This threshold value can be determined empirically by comparing positive controls (for examples, samples with a certain level of CD133 present) and negative controls (samples without CD133).

Such procedures and protocols employing anti-CD133 monoclonal antibodies may be useful in a wide range of analytical, diagnostic and therapeutic applications, for example, in research and laboratory applications in which detection of CD133 is desirable, or in methods of assessing various conditions, such as cancer, in subjects. Since the presence of CD133 may be indicative of cancer stem cells, monoclonal anti-CD133 antibodies according to the embodiments of the present invention may be used in the methods of detecting and monitoring cancer stem cells (cancer cells that can self-renew and drive tumorogenesis) in samples or in subjects.

The terms "assess," "assessment" "detect," "detecting," "indicate," "indicative" and similar terms are used in this document to broadly refer to a process or discovering or determining the presence or an absence, as well as a degree, quantity, or level, or probability of occurrence of something. For example, the term "assessing" when used in reference to a disease or a condition can denote discovery or determination one or more of presence of a disease or a condition, absence of a disease or a condition, progression, level or severity of a disease or a condition, as well as a probability of present or future exacerbation of symptoms, or of efficacy of a treatments. The terms "assess," "assessment," "assessing" and the related terms may be used in reference to cancer, status of cancer or status of a subject with cancer, and in some other contexts. These terms can denote, but are not limited to, inferring the presence or the absence of cancer stem cells in cancerous tumors based on the detected presence or absence of CD133 in the tumors. The terms "assess." "assessment," "assessing" and the related terms may also encompass, depending on the context, recommending or performing any additional diagnostic procedures related to evaluating cancer, evaluating potential effectiveness of the treatments for cancer, as well as recommending or performing such treatments, monitoring the cancer, or any other steps or processes related to treatment or diagnosis of a cancer. For example, evaluating prognosis of a cancer in a subject, or evaluating prognosis of a cancer subject fall within the scope of the terms "assess," "assessment," "assessing" and the related terms. These terms also encompass recommending or not recommending and performing or not performing treatment or diagnostic procedures based on the results of detection of cancer-associated mutations in the subject's tumors.

Diagnostic and Therapeutic Methods

Anti-CD133 monoclonal antibodies described in this document may be used in diagnostic as well as in therapeutic methods, or methods related to treating diseases or conditions. Some of these methods may be referred to as "screening" and/or "profiling" methods and may be employed in the fields of diagnostics, therapy, personalized medicine and other related fields. The term "condition" when used in reference to the embodiments of the present invention is used broadly to denote a biological state or process, which can be normal or abnormal or pathological. The term "condition" can be used to refer to a medical or a clinical condition, meaning broadly a process occurring in a body or an organism and distinguished by certain symptoms and signs. The term "condition" can be used to refer to a disease or pathology, meaning broadly an abnormal disease or condition affecting a body or an organism. Some examples of conditions related to the methods of using anti-CD133 monoclonal antibodies described in this document are cancers, such as breast cancer, colorectal cancer, glioblastoma, melanoma, lung cancer, ovarian cancer, gastric cancer, acute leukemia, acute lymphoblastic leukemia (AML), prostate cancer, liver cancer, kidney cancer sarcomas, brain cancers, leukemia, retinoblastoma. Some other examples of conditions related to the methods of using anti-CD133 monoclonal antibodies described in this document are Stargardt disease, an inherited form of juvenile macular degeneration Retinitis pigmentosa 41, and cone-rod dystrophy 12.

The term "cancer" as used herein includes solid tumor cancers and blood cancers. The term "solid tumor cancer" denotes the cancers that are characterized by the formation of cancerous tumors, or cohesive masses of abnormally proliferating cells, in tissues and organs. It is to be understood that some tumors formed by the solid tumor cancers can be cysts, meaning fluid-filled sacks of tissue. The term "solid tumor cancer" is used herein to distinguish tumor-forming cancers from the so-called blood cancers or hematological malignancies that are formed from hematopoietic (blood-forming) cells and affect blood, bone marrow, and lymph nodes. Examples of solid tumor cancers are carcinomas, or cancers derived from epithelial cells, sarcomas, or cancers arising from connective tissue, germ cell tumors, such as seminomas and dysgerminomas, blastomas, or cancers that derive from precursor cells or embryonic tissue. Some non-limiting examples of solid tumor cancers are lung cancer, breast cancer, colorectal cancer, prostate cancer, thyroid cancer, brain cancer, such as glioblastoma, and bladder cancer. Examples of hematological malignancies are lymphomas, leukemias, myelomas, myelodysplastic syndromes and myeloproliferative diseases.

Circulating tumor cells (CTCs) are included within the scope of the term "cancer." See, for example, "CD133 expression in circulating tumor cells from breast cancer patients: Potential role in resistance to chemotherapy." *Int. J. Cancer.* 2013, 33:2398-407; "Circulating and disseminated tumor cells in the management of breast cancer." *Am. J. Clin. Pathol.* 2009, 132:237-245; "Circulating tumor cells: a useful predictor of treatment efficacy in metastatic breast cancer." *J. Clin. Oncol.* 2009; 27:5153-5159; "Characterization of metastatic breast cancer patients with non-detectable circulating tumor cells." *Int. J. Cancer* 2011, 129:417-423; and "Epithelial-mesenchymal transition and stem cell markers in patients with HER2-positive metastatic breast cancer." *Mol. Cancer. Ther.* 2012; 11:2526-34

Anti-CD133 monoclonal antibodies described in this document may be used in methods of determining efficacy of a therapy, such as a cancer therapy in a subject based on a change or changes in CD133 expression levels. Such methods can be described as pharmacodynamic methods, or methods of evaluating efficacy of a treatment or therapy. An exemplary method comprises obtaining a first blood sample from a subject with cancer prior to treatment with a first cancer therapy, determining a value of CD133 expression in the first blood sample (i.e., as a baseline measurement), obtaining a second blood sample from a subject with cancer after at least one treatment with the first cancer therapy, determining a second CD133 value in the second blood sample (i.e., as a means of assessing the treatment effect), and comparing the first value to the second value. An increase in CD133 value may indicated that the cancer therapy is insufficiently effective and that a second cancer therapy or an increase in dosing regimen (increased dosage or frequency using the current treatment agent) for the subject should be selected. A second cancer therapy can also include administration of multiple chemotherapeutics in combination, surgery, and/or radiation therapy. Proper dosages and treatment methods, or change in treatment regimens can be determined by accepted methods.

Anti-CD133 monoclonal antibodies described in this document may be used in various other methods, that can be characterized, depending on the context, as screening, diagnostic, therapeutic or treatment methods. For example, anti-CD133 monoclonal antibodies of the present invention may be employed in methods of detecting presence, absence or amount of cancer stem cells in the sample, where the presence, absence or amount of CD133 polypeptide detected in the sample with the help of anti-CD133 monoclonal antibodies is indicative of the presence, absence or amount of the cancer stem cells in the sample. In another example, anti-CD133 monoclonal antibodies of the present invention may be used in methods of detecting presence, absence or amount of circulating tumor cells (CTCs) in the sample, such as a blood sample, where and the presence, absence or amount of CD133 polypeptide detected in the sample with the help of anti-CD133 monoclonal antibodies indicative of the presence, absence or amount of the circulating tumor cells in the sample. In one more example, anti-CD133 monoclonal antibodies of the present invention may be useful for detecting presence, absence or amount of CD133-positive cells in the sample, such as a blood sample, where the presence, absence or amount of CD133 polypeptide detected in the sample with the help of anti-CD133 monoclonal antibodies is indicative of the presence, absence or amount of the CD133-positive cells in the sample.

In yet one more example, anti-CD133 monoclonal antibodies of the present invention are used as reagents for removing CD133-positive cells from a sample. When a monoclonal antibody is contacted with the samples under conditions under which specific binding of the monoclonal antibody and CD133 polypeptide expressed by the CD133-positive cells may occur, complexes the monoclonal antibody and the CD133-positive cells for and can be removed from the sample. The removal may be accomplished by a variety of procedures, one of examples being blood plasma filtration. Blood can be removed from the patient, pumped through a filter device containing bound CD133 mABs that capture the CD133 expressing cells, and, after capturing, the blood is returned to the patient. This method may be useful in preparatory or treatment methods, when it is desirable to reduce the number of the CD133-positive cells a sample of blood or a marrow sample obtained from a subject. Such procedures may be useful in the context of transplantation or transfusion, or in the context of cancer treatment methods. Some other methods of treatment, in which the monoclonal antibodies of the present invention may be usefully employed, are discussed below.

Treatment Methods and Compositions

Methods of treating cancer in a subject that comprise administering a treatment or therapy in the subject based on the detection of CD133 levels using anti-CD133 monoclonal antibodies described in this document are also included among the embodiments of the present invention. The term "therapy" is used herein synonymously with the term "treatment," and may include surgical treatments. The term "cancer therapy" as used herein encompasses various types of cancer therapy or treatment, including surgery, radiotherapy, chemotherapy, and targeted drug therapy. A therapy may include one or more types of therapy. For example, a therapy may include a combination of chemotherapy and targeted drug therapy. The terms "therapy" and "treatment" can be used in conjunction with the terms "cycle" or "period." A therapy or treatment can be administered one or more times over a certain period of time, followed by a period during which no treatment or therapy is administered. A therapy cycle can last for days or weeks (in one example, four weeks). One or more cycles of therapy or treatment can be administered. For example, one, two, three, four, five, six, seven, eight, nine, ten or more than ten cycles of therapy or treatment can be administered. The therapy may be the same or varied during different cycles. For example, the types and/or the doses of therapy may be varied from cycle to cycle. During a therapy cycle, the therapies may be administered on a single day, several consecutive days, or continuously as an outpatient or as an inpatient. A therapy may last minutes, hours, or days, depending on the specific protocol. Therapy cycle may repeat weekly, bi-weekly, or monthly. A therapy cycle can include one or more therapy sessions. For example, a therapy cycle can be defined in monthly intervals, with two bi-weekly chemotherapy sessions classified as one cycle. One or more therapy cycles can be referred collectively as a "course" of therapy.

Compositions

Anti-CD133 monoclonal antibodies may be included in compositions employed in the treatment or alleviation of various conditions, such as cancer. Such conditions may be referred to as pharmaceutical compositions, therapeutic compositions, formulations, medicaments or by other terms. In one example, monoclonal antibodies according employed in such compositions may be neutralizing antibodies. A monoclonal antibody that binds CD133 is said to neutralize CD133, or be neutralizing, if the binding partially or completely inhibits one or more biological activities of CD133. For example, a neutralizing anti-CD133 monoclonal antibody at a concentration of 0.01, 0.1, 0.5, 1, 2, 5, 10, 20 or 50 µg/ml may inhibit a biological function of CD133 by about at least 50%, 75%, 90% or 95% 99% or essentially completely. The compositions containing neutralizing anti-CD133 antibodies may be administered to the subjects. That is, the antibodies can be used in the manufacture of a medicament for treatment or alleviation of a condition or disease. The compositions may contain the anti-CD133 monoclonal antibodies in a physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients.

Administration

Methods of treating a subject with a disease or a conditions using compositions containing anti-CD133 monoclonal antibodies described in this document are also including among the embodiments of the present invention. The composition can be administered to a patient by any suitable route, especially parentally by intravenous infusion or bolus injection, intramuscularly or subcutaneously. Intravenous infusion can be given over as little as 15 minutes, but more often for 30 minutes, or over 1, 2 or even 3 hours. The composition can also be injected directly into the site of disease (for example, a tumor), or encapsulated into carrying agents such as liposomes. The dose given will be sufficient to alleviate the condition being treated ("therapeutically effective dose") and may be 0.1 to 5 mg/kg body weight, for example 1, 2, 3 or 4 mg/kg, but may be as high as 10 mg/kg or even 15 or 20 mg/kg. A fixed unit dose may also be given, for example, 50, 100, 200, 500 or 1000 mg, or the dose may be based on the patient's surface area, e.g., 100 mg/m$^2$. Between 1 and 8 doses, (e.g., 1, 2, 3, 4, 5, 6, 7 or 8) may be administered over a therapy cycle, but 10, 20 or more doses may be given. The monoclonal antibody can be administered daily, biweekly, weekly, every other week, monthly or at some other interval, depending. e.g. on the half-life of the monoclonal antibody, for 1 week, 2 weeks, 4 weeks, 8 weeks, 36 months or longer. Repeated courses of treatment are also possible, as is chronic administration. A regime of a dosage and intervals of administration that alleviates or at least partially arrests the symptoms of the disease (biochemical, histologic and/or clinical), including its complications and intermediate pathological phenotypes in development of the disease is referred to as a therapeutically effective regime.

Prophylactic Methods

The pharmaceutical compositions containing anti-CD133 monoclonal antibodies can also be used in prophylaxis of a patient at risk of cancer. Such patients include those having genetic susceptibility to cancer, patients who have undergone exposure to carcinogenic agents, such as radiation or toxins, and patients who have undergone previous treatment for cancer and are at risk of recurrence. A prophylactic dosage is an amount sufficient to eliminate or reduce the risk, lessen the severity, or delay the onset of the disease, including biochemical, histologic and/or clinical symptoms of the disease, its complications and intermediate pathological phenotypes presenting during development of the disease. Administration of a pharmaceutical composition in an amount and at intervals effective to effect one or more of the above is referred to as a prophylactically effective regime.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Development of Monoclonal Antibodies

Antigen

Figure 1:
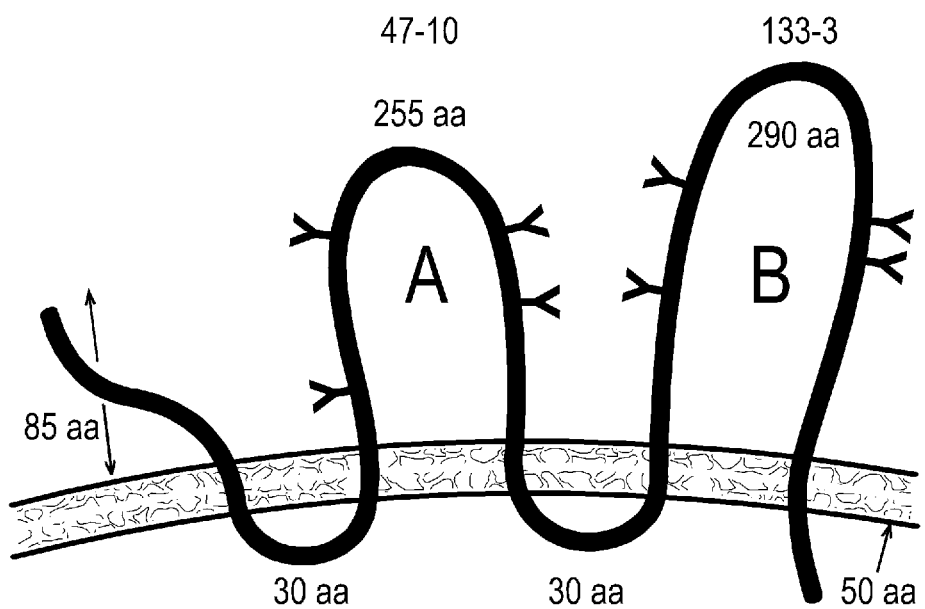
FIG. 1 shows a schematic illustration of tertiary structure of CD133 protein. Reproduced from. Adapted from an illustration published in 2003 catalog of R&D Systems Inc., Minneapolis, Minn.

Tertiary structure of CD133 protein is schematically illustrated in FIG. 1. For immunization, CD133 immunogenic polypeptides were prepared using amino acid sequences corresponding to CD133 sequences selected from extracellular domains A and B of CD133 protein. The amino acid sequences for the immunogenic polypeptides were selected based on their predicted antigenicity, which was calculated with the software using the method described in Kolaskar and Tongaonkar, "A semi-empirical method for prediction of antigenic determinants on protein antigens" *FEBS Lett.* 1990

276(1-2):172-4. Surface exposure of the amino acid residues was taken into account, and CD133 glycosylation sites known to be located at amino acids 220, 274, 395, 414, 548, 580, 729 and 730 were expressly avoided. In reference to CD133 amino acid sequence NCBI accession number NP_006008.1 (SEQ ID NO:1, shown in FIG. 2), the two amino acid sequences employed in the immunogenic polypeptides corresponded to amino acids 295-329 and 615-643 of CD133 amino acid sequence. The N-terminal lysine residue of Peptide A (SEQ ID NO: 17) was used for conjugation, whereas a lysine residue was added as a c-terminal residue of peptide B (SEQ ID NO: 18) for conjugation, as shown in Table 2.

TABLE 2

CD133 immunogenic polypeptides

| Polypeptide | | SEQ ID | Amino acids in CD133 sequence | CD133 domain |
|---|---|---|---|---|
| A | KTSLRSSLNDPLCLV HPSSETCNSIRLSLS QLNSN | SEQ ID NO: 17 | 295-329 | A |
| B | RKNLQDFAACGIDRM NYDSYLAQTGKSPAK | SEQ ID NO: 18 | 795-329 | B |

Immunization

For immunization, recombinant polypeptides I and II were expressed in *Escherichia coli*, purified, and conjugated to Keyhole limpet hemocyanin (KLH) using standard protocols. An equimolar mixture of both conjugated polypeptides was used to prepare an immunogen according to the procedure discussed below. Two three-month old New Zealand white rabbits were immunized using a protocol of five injections and two test bleeds per rabbit. At the time of each injection, aliquots of peptide mixture were thawed and combined with Complete Freund's Adjuvant (CFA) (for the first injection) or with incomplete Freund's Adjuvant for the subsequent injections. The injection route was subcutaneous. Immunization and bleed details are summarized in Table 3.

TABLE 3

Immunization and bleed schedule.

| Date | Procedure | immunization or bleed # | Amount of polypeptide injected (mg) or blood obtained (ml) |
|---|---|---|---|
| Jun. 19, 2012 | Bleed | 0 | 5 ml |
| Jun. 20, 2012 | Injection | 1 | 0.5 mg |
| Jul. 11, 2012 | Injection | 2 | 0.25 mg |
| Jul. 25, 2012 | Injection | 3 | 0.25 mg |
| Aug. 8, 2012 | Injection | 4 | 0.25 mg |
| Aug. 20, 2012 | Bleed | 1 | 5 ml |
| Aug. 22, 2012 | Injection | 5 | 0.25 mg |
| Sep. 3, 2012 | Bleed | 2 | 5 ml |

Blood Screening

During the primary screening of the blood samples, colorimetric ELISA against BSA-conjugated immunogenic peptides A and B (see Table 2) and was performed as follows. ELISA plates (96 well, Grenier or Nunc) were coated with 50 ng/well of peptide-BSA conjugate in bicarbonate buffer, pH 9.6, incubated at 4° C. overnight, then blocked with 1% BSA in Tris buffered saline (TBS). Diluted (1:250-1:256,000) rabbit anti-sera (50 µl/well) were added and incubated at room temperature. Plates were washed with Tris buffered saline (TBS) with 0.05% Tween (TBST). Anti-rabbit secondary antibody conjugated to alkaline phosphatase (PIERCE: cat #31340; 1:2,500 dilution, prepared in 1% BSA-TBS) was used for detection with p-nitrophenyl phosphate (PNPP) substrate. Optical density (O.D.) of the plate wells at 405 nm was measured with a plate reader. The results are summarized in Table 4 and illustrated in FIG. 3, panels A and B.

Figure 3:
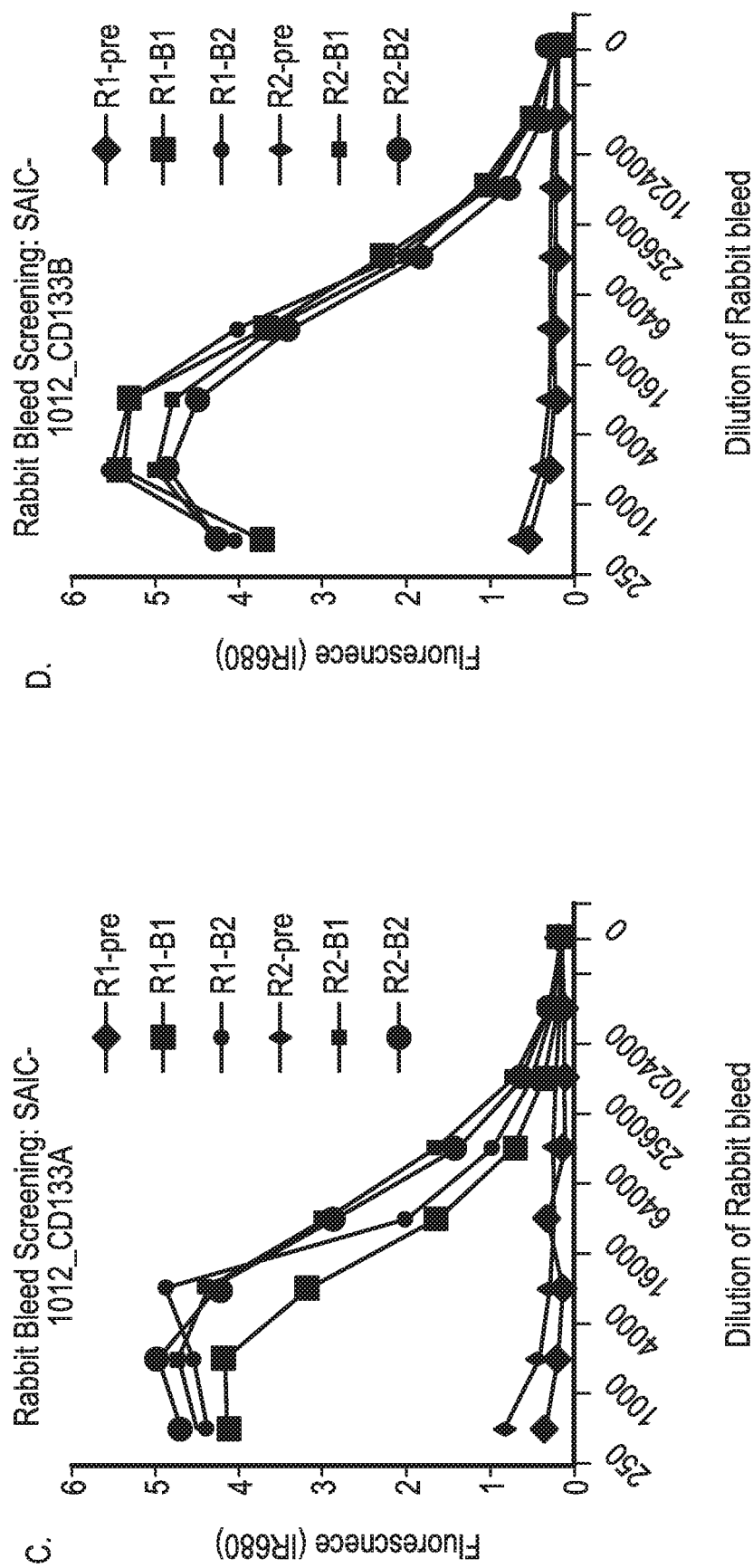
FIG. 3 illustrates of the results of the screening by enzyme-linked immunosorbent assay (ELISA) of blood samples obtained from the rabbits immunized by CD133 immunogens. Panel A shows a colored photograph of an ELISA plate screened by a recombinant CD133 domain A polypeptide. Panel B shows a picture of an ELISA plate screened by a recombinant CD133 domain B polypeptide. The samples in panels A and B are coded as follows: Pre—pre-bleed sample; B1—bleed 1; B2—bleed 2. Panel C is a line plot showing detected fluorescence levels (Y axis) observed for different dilutions of the blood samples screened by a recombinant CD133 domain A. Panel D is a line plot showing detected fluorescence levels (Y axis) observed for different dilutions of the blood samples screened by recombinant CD133 domain B polypeptide. The samples are coded as follows: R1-pre—rabbit 1, pre-bleed sample; R1-B1—rabbit 1, bleed 1; R1-B2—rabbit 1, bleed 2; R2-pre—rabbit 2, pre-bleed sample; R2-B2—rabbit 2, bleed 2; R2-B2—rabbit 2, bleed 2.

Secondary screening of the blood samples was conducted with using BSA-conjugated immunogenic CD133 polypeptides A and B as well as recombinant polypeptides of CD133 domain A (amino acids 180-400 plus 21 amino acid tag; SEQ ID NO:19, shown below) and domain B (amino acids 515-745 plus 24 amino acid tag; SEQ ID NO:20, shown below) produced in *E. coli*. The secondary screening was conducted as follows. Flat bottom, black, high binding 360 µL plates with clear bottom (VWR) were coated with 100 ng/well of peptide-BSA conjugate in bicarbonate buffer, pH 9.6 (Sigma), incubated at 4° C. overnight and blocked with ODYSSEY® blocking buffer (LiCor). Diluted (1:250-1:1,000,000) rabbit anti-sera (100 µl/well) were added to the plates, which were then incubated at 24° C. for 1-2 hours, and washed with phosphate-buffered saline (PBS) with 0.05% Tween-20 (PBS-T). Anti-rabbit secondary antibody conjugated to IR680 fluorescent dye (LiCor) was used for detection. Plates were read at 700 nm wavelength with a Licor ODYSSEY® scanner. Images were quantified using Licor ODYSSEY® application software v. 3.0. The results of the secondary screening are illustrated in FIG. 3, panels C and D.

TABLE 4

Primary screening data (O.D. measured at 405 nm)

| | Screening Antigen | | | | |
|---|---|---|---|---|---|
| | A-BSA | | B-BSA | | Control antigen and |
| | Bleed # | | | | |
| Dilution | B1 | B2 | B1 | B2 | antibody |
| Rabbit 1 | | | | | |
| 1:250 | 1.10 | 1.73 | 1.85 | 1.74 | 1.10 |
| 1:1,000 | 1.19 | 1.63 | 1.79 | 1.63 | 1.13 |
| 1:4,000 | 1.32 | 1.47 | 1.76 | 1.79 | 0.76 |
| 1:16,000 | 1.08 | 1.23 | 1.34 | 1.11 | 0.60 |
| 1:64,000 | 0.70 | 0.60 | 0.84 | 0.70 | 0.35 |
| 1:256,000 | 0.31 | 0.32 | 0.41 | 0.34 | 0.20 |
| 0 (background no bleed/primary antibody) | 0.09 | 0.09 | 0.08 | 0.09 | 0.12 |
| Pre-Bleed (1:60,000) | 0.13 | 0.08 | 0.09 | 0.08 | 0.31 |
| Rabbit 2 | | | | | |
| 1:250 | 1.41 | 1.31 | 1.34 | 1.25 | 1.38 |
| 1:1,000 | 1.51 | 1.49 | 1.34 | 1.42 | 1.49 |
| 1:4,000 | 1.43 | 1.34 | 1.59 | 1.32 | 1.18 |
| 1:16,000 | 1.08 | 1.08 | 1.18 | 1.08 | 0.79 |
| 1:64,000 | 0.62 | 0.58 | 0.80 | 0.72 | 0.45 |

TABLE 4-continued

Primary screening data (O.D. measured at 405 nm)

|  | Screening Antigen | | | | |
| --- | --- | --- | --- | --- | --- |
|  | A-BSA | | B-BSA | | Control antigen and |
|  | Bleed # | | | | |
| Dilution | B1 | B2 | B1 | B2 | antibody |
| 1:256,000 | 0.29 | 0.29 | 0.39 | 0.34 | 0.19 |
| 0 (background no bleed/primary antibody) | 0.12 | 0.09 | 0.08 | 0.09 | 0.10 |
| Pre-Bleed (1:60,000) | 0.08 | 0.08 | 0.08 | 0.08 | 0.07 |

```
Recombinant CD133 domain A polypeptides
                                   (SEQ ID NO: 19)
MHHHHHHSSGVDLGTENLYFQSNANHQVRTRIKRSRKLADSNFKDLRT

LLNETPEQIKYILAQYNTTKDKAFTDLNSINSVLGGGILDRLRPNIIP

VLDEIKSMATAIKETKEALENMKSTLKSLHQQSTQLSSSLTSVKTSLR

SSLNDPLCLVHPSSETCNSIRLSLSQLKSKPELRQLPPVDAELDNVNN

VLRTDLDGLVQQGYQSLNDIPDRVQRQTTTVVAGIKRVLNSIGSDIDN

VTQRL

Recombinant CD133 domain B polypeptides
                                   (SEQ ID NO: 20)
MHHHHHHSSGVDLGTENLYFQSNAICEPYTSKELFRVLDTPYLLNEDW

EYYLSGKLFNKSKMKLTFEQVYSDCKKNRGTYGTLHLQNSFNISEHLN

INEHTGSISSELESLKVNLNIFLLGAAGRKNLQDFAACGIDRMNYDSY

LAQTGKSPAGVNLLSFAYDLEAKANSLPPGNLRNSLKRDAQTIKTIHQ

QRVLPIEQSLSTLYQSVKILQRTGNGLLERVTRILASLDFAQNFITNN

TSSVIIEETKKYGRT
```

Fusion

Rabbit 1 was selected for splenectomy and fusion due to higher antibody titers observed in the blood samples. A final boost of immunogen composition (peptides A+B) was administered to Rabbit 1 intravenously, and splenectomy was performed. Splenocytes were isolated from the spleen tissue. Four hundred million lymphocyte spleen cells were fused with 200 million fusion partner cells and plated on 40 96-well plates. The plates were kept in tissue culture incubators under standard conditions. Fusion data is shown in Table 5.

TABLE 5

Fusion data for the spleen tissue sample from rabbit 1.

| Harvest Date | Tissue Type | Weight (g) | Size (cm) | Cell Viability (%) | Total Cells (M) | Notes |
| --- | --- | --- | --- | --- | --- | --- |
| Oct. 9, 2012 | spleen | 3.89 | 7 | 85 | 2500 | 40X fusion |

Hybridoma Screening

Cell growth of the hybridoma culture was monitored for 2-3 weeks after fusion. Hybridoma supernatants were screened by standard colorimetric ELISA against BSA-conjugated immunogenic peptides A and B, as described earlier for primary screening. The hybridoma screening process consisted of an initially screen on 40 plates, using bleed 2 of Rabbit 1 at 1:100 dilution as a positive control. Clones with O.D. greater than 0.5 were considered putatively positive and were further expanded to a 24-well plate. Confirmatory screen was performed, and six clones were confirmed positive against the same BSA-Conjugated peptides as those used for bleed screening. Additional screening was performed by the same ELISA assay according to the secondary screening procedure described above. Western blotting was performed on the clones selected for subcloning.

Subcloning and Subclone Screening

Subcloning was performed using limited cell dilution method using standard protocols. Positive subclones were selected for screening and screened by ELISA and Western blot. As a result of the screening, mAb subclones 47-10 (domain A specific) and 133-3 (domain B specific) were selected for production of the purified mAbs.

Cloning of cDNA

The cDNA of mAb subclones termed "47-10" and "133-3" was cloned to generate recombinant antibodies. The cDNAs of IgG heavy and light chains were amplified by polymerase chain reaction (PCR) and cloned into a mammalian expression vector. The recombinant monoclonal antibody was then transiently expressed using a HEK293 cell system. The expressed recombinant antibodies were then tested by ELISA against CD133 immunogenic polypeptides A and B and recombinant domain A and B polypeptides. FIG. 4 illustrates the results of ELISA testing of mAbs 47-10 (panel A) and 133-3 (panel B). The testing confirmed the specificity of the mAbs. The cDNA was sequenced. FIGS. 5-10 illustrate the amino acid sequences of mAbs 47-10 and 133-3.

Purification of Recombinant Antibodies

Recombinant antibodies were produced In a HEK293 cell system in serum-free medium and purified by protein A. Briefly, protein A gel (GE Life Science) was pre-washed with $dH_2O$ until $OD_{280}$<0.05 was achieved, then re-equilibrated extensively with 1×PBS. The protein A gel was then incubated with rotation overnight at 4° C. with antibody-containing supernatant and binding buffer, pH 8.0 (Pierce), at volume ratio 1:1. After the incubation, a chromatography column was packed with the protein A gel, and the flow-through collected. The protein A gel was washed with 1×PBS until $OD_{280}$<0.05 was achieved. The recombinant antibodies were eluted off the gel with 10 ml of elution buffer, pH 2.8 (Pierce). The eluate was collected in 1 ml fractions into the glass tubes containing 100 µl IM Tris-HCl neutralizing buffer, pH8.0. Absorbance at 280 nm of each eluted fraction was measured. The fractions with positive $OD_{280}$ were pooled and dialyzed against 1×PBS (with at least 2 exchanges) overnight at 4° C. The antibodies were then concentrated to desired concentration using ultra centrifugal filter units (Amicon, Millipore).

Example 2

Specificity of Monoclonal Antibodies and Use in Immunoassays

Specificity Testing Via ELISA

The specificity of the monoclonal antibodies was demonstrated by direct ELISA with the antigenic peptides A and B conjugated to BSA or the recombinant CD133 extracellular domain peptides described in Example I. As illustrated by FIG. 4, based on ELISA results, mAbs 47-10 and 133-3 bound to the polypeptides corresponding to CD133 extracellular domains. A and B, respectively, and no cross-reaction with the other CD133 extracellular domain was observed.

Specificity Testing Via Western Blotting

The specificity of mAbs 47-10 and 133-3 was demonstrated by employing them as primary antibodies for detection of CD133 in Western blots of lysates from the cells expressing CD133. As illustrated in FIGS. 11 and 12, mAbs 47-10 and 133-3 both detected the bands at about 97 and approximately 120-133 kDa, which is consistent with the predicted MWs for unglycosylated and glycosylated forms of CD133, respectively.

Specificity Testing Via Immunofluorescence Assay

MAbs 47-10 and 133-3 were tested in a slide-based immunofluorescent assay (IFA). Formalin fixed paraffin embedded (FFPE) pellets were generated using cells known to express CD133 (cell lines HT29, HCT-116, SKMEL28, or SW620), as well as the cells negative for CD133 expression (U87 or A375). The cells were grown in vitro and harvested by scraping, transferred into sterile 50 ml conical centrifuge tubes with media containing 10% serum and pelleted at 1000×g for 5 minutes. Cell growth medium was replaced with fresh serum-containing medium and centrifuged again at 1000×g for five minutes. All but approximately 1 ml of the medium was removed from the tubes, and the pellet was re-suspended by flicking the tubes. Suspended cells were transferred using a 2 ml pipette into a clean 1.5 ml conical Eppendorf tube. The cells were the pelleted for 30 seconds at 8,000 rpm in an Eppendorf microcentrifuge. Most of the supernatant was discarded, leaving approximately 100-200 μl in each tube. The cell pellet was loosened by gently flicking the tubes and thrombin stock (8 μl of 1 unit/μl solution in water, Sigma) was added. The cells were mixed briefly by gently flicking the tubes, then held on ice for 2-5 minutes. Fibrinogen stock (5 μl of 10 mg/ml aqueous solution) was added, and the tubes were incubated for 2-5 minutes at room temperature. The clotted cells were pelleted by a brief centrifuge for 20 seconds at 10K. The supernatant was discarded, and 1.0 ml of room temperature 10% neutral buffered formalin (Sigma) was added. The cells were then fixed at room temperature for 8-16 hours. Following fixation, the cells were centrifuged 30 seconds at 8,000 rpm in an Eppendorf micro centrifuge. The supernatant (fixative) was removed, and 1 ml of 70% ethanol in nuclease-free water was added. Paraffin processing was performed within 3 days. The slides were generated and stained with mAbs 47-10 and 133-3 as primary antibodies. Image capture of FFPE tissue sections was carried out using a Nikon 90i Microscope with an A1 confocal head with a 20× objective. As illustrated in FIGS. 13-15, mAbs 47-10 and 133-3 specifically detected CD133 expression in IFA.

Detection of CD133 in the A375 xenograft material in spite of the fact that Western blots and IFA of A375 cells grown in vitro were negative for CD133 is consistent with previous studies, which found that A375 melanoma cells, despite harboring a comparable number of CD133+ cells in xenografts, are negative for CD133 in vitro. Similar induction of CD133+ subsets from CD133 cells in vivo have been observed by others, suggesting that tumor "stemness" is a dynamic process and progenitor marker-negative cells may evolve into CSCs through proper environment cues or accumulating genetic alterations, the so-called stochastic model of CSC hypothesis. See Lai et al. 2012 "CD133$^+$ Melanoma Subpopulations Contribute to Perivascular Niche Morphogenesis and Tumorigenicity through Vasculogenic Mimicry" *Cancer Res.* 72:5111-5118. Thus, others have observed similar findings of A375 cell lines being negative for CD133, with CD133 is detected in the resulting tumor when these cell are injected into a mouse, possibly due to stimulation from the tumor microenvironment/stroma inducing the stem cell phenotype.

Example 3

Use of mAbs 47-10 and 133-3 to Detect Expression of CD133 in Non-Small Cell Lung Cancer Xenograft Tumors In vivo studies were performed in a non-small cell lung cancer xenograft model. mAbs 47-10 and 133-3 were used to detect expression of CD133 protein in non-small cell lung cancer xenograft tumors. FIG. 18 illustrates the results of the immunofluorescence staining of the samples of H596 non-small cell lung cancer xenograft tumors in mice expressing known cancer stem cell biomarkers, including CD133. Staining for EMT and/or CSC biomarkers staining of H596 tumors grown in immunocompromised hHGF$^{scid/scid}$ mice and hHGF$^{ki/ki}$ mice was performed. Immunofluorescence images suggested that CD133 was expressed in a majority of cells in H596 tumors grown in hHGF$^{scid}$ mice, but CD133 expression diminished on tumor cells that has undergone EMT transition in hHGF$^{ki/ki}$ microenvironment, as evidenced by the increased Slug staining in invading cells. Diminished CD133 expression was observed in apparently invasive H596 tumor cells that has upregulated Slug expression. Other known CSC lung biomarkers, such as CD44 and ALDH1, were found to be co-expressed with CD133 in the H596 tumor cells in tumors grown in hHGF$^{scid/scid}$. The expression of these markers appeared to be down regulated in tumors derived from or hHGF$^{ki/ki}$ mice, suggesting that these markers also became down regulated in cells undergoing EMT in hHGF$^{ki/ki}$ microenvironment, similarly to CD133.

Example 4

Use of Monoclonal Antibodies 47-10 and 133-3 to for PD Applications of Detect Changes in Expression of CD133 as a Stem Cell Marker in Xenograft Tumors In vivo PD studies are performed in a triple negative breast cancer (TNBC) xenograft model SUM149PT. Clone 47-10 and 133-3 are demonstrated to work in a slide based IFA on Formalin fixed paraffin embedded (FFPE) tumor xenograft tissues. The triple negative breast cancer (TNBC) xenograft model SUM149PT is treated with the antimicrotubule agent paclitaxel to enrich for CSC populations in tumors, followed by drug combination with either a TGFβ inhibitor (LY-215729) or FAK inhibitor (VS-6063) to show inhibition of CSC populations and tumor growth in these tumors. CD133 is used as a marker to monitor CSC tumor growth and inhibition in these models. Paclitaxel treated group shows increased CD133 staining consistent with enriched levels for CSC populations, as compared to the vehicle treated group, which was administered only the medium for delivery of the drugs ("vehicle"), such as water, saline, buffer, or other medium. Subsequent treatment or co treatment with TGFβ inhibitor (LY-215729) or FAK inhibitor (VS-6063) shows decreased CD133 levels, as compared to paclitaxel-treated group. Paclitaxel-treated group shows decreased tumor growth consistent with published data for paclitaxel treatment in this model.

Example 5

Comparison of mAbs 47-10 and 133-3 with Commercially Available Antibodies by Western Blotting and Immunofluorescence Assay MAbs 47-10 and 133-3 were compared with each other and anti-CD133 commercially available antibodies, including those available from Miltenyi Biotech. Comparison of mAbs 47-10 and 133-3 with commercially available antibodies was conducted by Western blotting and IFA.

Comparison by Western Blotting

The comparison was conducted on identical replicate Western blots of crude cell lysates. FIG. 16 illustrates the comparison of Western blots using mAbs 47-10 (panel A), 133-3 (panel B) and commercial mAbs obtained from Miltenyi Biotec (AC133—panel D: 293C3—panel E) as the primary antibodies. The samples were loaded at 50 µg/well on 4-12% Tris Bis 1.5 mm gels, and the electrophoresis was run in MOPS running at 150V. The proteins were transferred to nitrocellulose membranes for 2 hours at 4° C. The blots were blocked with Odyssey blocking buffer (Licor) and incubated with primary antibodies overnight at 4° C. at 1 µg/ml. Either goat anti-rabbit-IR-800 at 0.1 µg/ml (for clones 47-10 and 133-3) or goat anti-mouse-IR-800 at 0.1 µg/ml (for Miltenyi Biotec mAbs) were used as secondary antibodies. mAbs 47-10 and 133-3 detect CD133 specific bands with good specificity while Miltenyi monoclonal antibodies do not detect CD133 with good specificity. The results showed that mAbs 47-10 and/or 133-3 were specific for CD133, and that they were far more effective than the commercially available antibodies tested. For example, mAbs 47-10 and/or 133-3 detected CD133 in the cell lysate by Western blotting and they were therefore considered suitable for certain immunoassay applications, such as certain pharmacodynamic assays or other techniques. In contrast commercially available CD133 antibodies resulted in very weak detection and are therefore judged to be unsuitable for certain immunoassay applications, such as certain pharmacodynamic assays or other techniques.

Comparison by IFA on Cell Pellets.

FIG. 17 illustrates the comparison of mAbs 47-10 and 133-3 and commercial mAbs obtained from Miltenyi Biotec conducted by immunofluorescence staining of FFPE samples of cells representing the cell lines with varying CD133 mRNA expression levels. Antigen retrieval was performed using citrate buffer, pH 6.0, for 20 minutes and 10% normal goat serum (NGS) for blocking non-specific staining. Immunofluorescence staining was performed in a Bond-max Autostainer (Leica Microsystems) using 10 µg/ml of the above-listed CD133 antibodies as primary antibodies and either goat anti-rabbit-AF546 (for mAbs 47-10 and 133-3) or goat anti-mouse-AF546 (for Miltenyi Biotec mAbs) as secondary antibodies. DAPI was used as nuclear counterstain. Slides were imaged on a fluorescence microscope (Nikon 90i Andor Camera, NIS Elements Software). The testing showed higher sensitivity of mAbs 47-10 and 133-3, in comparison to commercially available antibodies.

Comparison by IFA on Human Tissue Tumor Micro Arrays

MAbs 47-10 and 133-3 were successfully used in several IFA assay applications. Based on the testing results (illustrated by the figures discussed below), mAbs 47-10 and 133-3 appeared to be at least equivalent to commercially available antibodies in some cases and showed more intense staining in other cases. FIG. 19 illustrates the comparison of mAbs 47-10 and 133-3 and commercial mAbs obtained from Miltenyi Biotec conducted by immunofluorescence staining of FFPE samples of a multitumor array consisting of a broad range of tumor types with varying CD133 levels (the specifications are shown in FIGS. 20A, 20B and 20C. FIG. 21 illustrates the comparison of select cores, at higher magnification than the previous figure, of mAbs 47-10 and 133-3 and commercial mAbs obtained from Miltenyi Biotec conducted by immunofluorescence staining of FFPE samples from selected cores of a multitumor array consisting of a broad range of tumor types with varying CD133.

Example 6

Use of mAbs 47-10 and 133-3 for Cancer Diagnostics

The testing was conducted to evaluate suitability of mAbs 47-10 and 133-3 for cancer diagnostics. The testing results, illustrated by the figures discussed below, indicated that mAbs 47-10 and 133-3 were suitable for cancer diagnostics. FIGS. 19, 21 and 22 illustrate the ability of mAbs 47-10 and 133-3 to stain a broad range of tumor types in an FFPE multitumor array MTU951 (Biomax, Inc.), which is described in FIGS. 20A, 20B and 20C. Selected results from FIG. 19 are shown at higher magnification in FIGS. 21 and 22.

FIG. 23 illustrates the ability of mAbs 47-10 and 133-3 to stain melanoma tumor types in an FFPE melanoma tumor array ME1004c (Biomax, Inc.) in an immunofluorescence assay. The array is described in FIGS. 24A, 24B and 24C. Selected results are shown at higher magnification in FIGS. 25 and 26. FIG. 25 illustrates the ability of mAbs 133-3 to differentially stain benign or malignant metastatic Melanoma tumors in an FFPE tumor array in an immunofluorescence assay.

Example 7

Antibody Specificity

Antibody binding is specific was demonstrated by peptide blocking experiments of FFPE HT-29 and SW620 cell pellets stained with mAbs 133-3 and 47-10. The results are shown in FIG. 27. The peptide corresponding to domain A (SEQ ID NO: 17, conjugated to BSA) specifically blocked mAb 47-10 but not mAb 133-3, while the peptide corresponding to domain B (SEQ ID NO:18, conjugated to BSA) blocked binding of mAb 133-3 but not mAb 47-10. BSA was used as a negative control and did not block the binding.

Example 8

Use of mAbs 47-10 and 133-3 in Pre-Clinical Studies In Vitro and In Vivo

In Vitro Studies

HT-29 cell lines expressing CD133 are treated with mAbs 47-10 or 133-3 (or their fragments or variants) resulting in cell kill, whereas U87 cells (negative for CD133) do not show significant changes in growth. Cells are washed twice with PBS, trypsinized and counted on a Cellometer (Nexcelom), using trypan blue to exclude dead cells.

In Vivo Studies in Mice

In vivo studies are conducted using mice engrafted with HT-29 or U87 tumors and treated with mAbs 47-10 or 133-3 (or their fragments or variants). Tumor cells are inoculated subcutaneously into female nude ($NC^{r/nu}$) mice, which are obtained from the Animal Production Area (National Cancer Institute-Frederick) in an AAALAC-accredited facility with an approved animal protocol. Treatment commences once tumors reach a weight of approximately 200 mg. Tumor weights are calculated as weight in mg=(length×width$^2$)/2. Optimal dosing and administration schedule are determined from maximum tolerated dose (MTD) and efficacy studies. NCI-Frederick is accredited by Association for the Assessment and Accreditation of Laboratory Animal Care International and follows the Public Health Service Policy for the Care and Use of Laboratory Animals. Animal care is provided in accordance with the accepted procedures. Mice engrafted with human patient derived tumors (PDx) expressing CD133 are also treated with mAbs 47-10 or 133-3 (or their fragments or variants), resulting in tumor stasis or regression.

Example 9

Use of Humanized mAbs 47-10 and 133-3 in Clinical Studies

Humanized mAbs 47-10 and 133-3 are used as therapeutic agents during a clinical study human patients. Screening for patients with high CD133 tumor levels is used for patient selection. All patients are enrolled in approved protocols and give informed consent. Clinical responses are observed in patients treated with humanized mAbs 47-10 and 133-3. Optimal dose is determined from dose escalation phase. Tumor stasis or regression is observed in some of the patients.

Example 10

Use of Humanized mAb 47-10 for Cancer Detection In Vivo

In vivo studies of mAb 47-10 for cancer detection were conducted using mice engrafted with Sum149-PT, a basal-like triple negative breast cancer tumor. Tumor cells were inoculated subcutaneously into nude mice obtained from the Biological Testing Branch, National Cancer Institute. Tumor weights were calculated as weight in mg=(length×width$^2$)/2. Optimal dosing and administration schedule were determined from maximum tolerated dose (MTD) and efficacy studies. Animal care was provided in accordance with the accepted procedures. The mice were treated with vehicle (water, 0.1 ml/10 g body wt), 67.5 mg/kg or 100 mg/kg (42 doses over 21 days) of a FAK inhibitor VS-606 (PO, BID x42), a putative inhibitor of cancer stem cells obtained from Verastem Inc. (Needham, Mass.). The tumors were collected at Day 4 after the last treatment dose. The tumors were fixed in 10% neutral buffered formalin and sectioned. The slides were prepared and stained with CD44v6 (clone 2F10, R&D Systems) and mAb 47-10 or mAb 47-10 only, followed by specific secondary antibodies, Goat anti-Rabbit IgG Alexa546 (for CD133) and Goat anti-mouse IgG Alexa 488; both antibodies from Thermo-Fisher. Stained sections were scanned by Aperio digital scanner, Leica Biosystems, Buffalo Grove, Ill., and quantified by Definiens (Carlsbad, Calif.) tissue analysis software. FIG. 28 shows the scatter graphs illustrating the results of quantitation of CD133+ CD44v6+ colocalized cells. FIG. 29 shows the scatter graphs illustrating the results of quantitation of CD133+ cell alone. Both graphs show significant decreases in CD133+ CSCs in FAK-inhibitor treated xenograft tumors.

All patents and non-patent publications and other information cited above are incorporated herein by reference in their entirety. Various embodiments of the invention have been described in fulfillment of the various objectives of the invention. It should be recognized that these embodiments are merely illustrative of the principles of the present invention. Numerous modifications and adaptations thereof will be readily apparent to those of skill in the art without departing from the spirit and scope of the invention as defined in the following claims.

The invention claimed is:

1. An anti-CD133 monoclonal antibody having an antibody binding site comprising CDR-H1 comprising residues 44-50, 44-53, 49-53 or 48-53 of SEQ ID NO:9, CDR-H2 comprising residues 70-74, 68-76, 68-83 or 65-76 of SEQ ID NO:9, CDR-H3 comprising residues 114-116 or 112-115 or SEQ ID NO:9, CDR-L1 comprising residues 46-58 or 52-60 of SEQ ID NO:11, CDR-L2 comprising residues 74-80 or 70-79 of SEQ ID NO:11, and CDR-L3 comprising residues 113-125 or 113-124 of SEQ ID NO:11.

2. The anti-CD133 monoclonal antibody of claim 1, comprising SEQ ID NO:9 or a variant thereof having 90% or more homology to SEQ ID NO:9 in its heavy chain.

3. The anti-CD133 monoclonal antibody of claim 1, comprising SEQ ID NO:11 or a variant thereof having 90% or more homology to SEQ ID NO:11 in its light chain.

4. The anti-CD133 monoclonal antibody of claim 3, further comprising SEQ ID NO:9 or a variant thereof having 90% or more homology to SEQ ID NO:9 in its heavy chain.

5. The anti-CD133 monoclonal antibody of claim 1, comprising SEQ ID NO:9 in its heavy chain.

6. The anti-CD133 monoclonal antibody of claim 1, comprising SEQ ID NO:11 in its light chain.

7. The anti-CD133 monoclonal antibody of claim 1, comprising a heavy chain of SEQ ID NO:9 and a light chain of SEQ ID NO:11.

8. The anti-CD133 monoclonal antibody of claim 1, wherein the monoclonal antibody is capable of specifically binding domain A but not domain B of a CD133 polypeptide, wherein the CD133 polypeptide is glycosylated or unglycosylated.

9. The anti-CD133 monoclonal antibody of claim 1, wherein the monoclonal antibody is recombinantly produced.

10. The anti-CD133 monoclonal antibody of claim 1, wherein the monoclonal antibody comprises a moiety not naturally occurring in a monoclonal antibody molecule.

11. A method of detecting a presence or absence of CD133 polypeptide in a sample, comprising:
contacting the sample with the monoclonal antibody of claim 1 under conditions under which specific binding of the monoclonal antibody and the CD133 polypeptide may occur;
detecting the specific binding of the monoclonal antibody to the CD133 polypeptide,
wherein the detected specific binding is indicative of the presence of the CD133 polypeptide in the sample; and,
optionally further comprising determining an amount of CD133 polypeptide present in the sample.

12. A method of isolating CD133-positive cells from a sample, comprising:
contacting a sample comprising cells with the monoclonal antibody of claim 1 under conditions under which specific binding of the monoclonal antibody and CD133 polypeptide expressed by the CD133-positive cells may occur, thereby allowing complexes the monoclonal antibody and the CD133-positive cells to form; and,
isolating the complexes of the monoclonal antibody and the CD133-positive cells from the sample.

13. The method of claim 12, wherein the sample is a blood sample or a marrow sample.

* * * * *

SEQUENCE LISTING

```
<160> NUMBER OF SEQ ID NOS: 20

<210> SEQ ID NO 1
<211> LENGTH: 865
<212> TYPE: PRT
<213> ORGANISM: Homo sapiens

<400> SEQUENCE: 1

Met Ala Leu Val Leu Gly Ser Leu Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110
```

```
Cys Val Leu Gly Leu Leu Phe Ile Ile Leu Met Pro Leu Val Gly Tyr
            115                 120                 125

Phe Phe Cys Met Cys Arg Cys Cys Asn Lys Cys Gly Gly Glu Met His
        130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
                180                 185                 190

Leu Ala Asp Ser Asn Phe Lys Asp Leu Arg Thr Leu Leu Asn Glu Thr
            195                 200                 205

Pro Glu Gln Ile Lys Tyr Ile Leu Ala Gln Tyr Asn Thr Thr Lys Asp
        210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
        435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
```

```
Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
        675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
    770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
        835                 840                 845

Asp His Val Tyr Gly Ile His Asn Pro Val Met Thr Ser Pro Ser Gln
    850                 855                 860

His
865

<210> SEQ ID NO 2
<211> LENGTH: 856
<212> TYPE: PRT
<213> ORGANISM: Gorilla gorilla gorilla

<400> SEQUENCE: 2

Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
                20                  25                  30
```

-continued

```
Asn Tyr Glu Leu Pro Ala Thr Lys Tyr Glu Thr Gln Asp Ser His Lys
             35                  40                  45
Ala Gly Pro Ile Gly Ile Leu Phe Glu Leu Val His Ile Phe Leu Tyr
 50                  55                  60
Val Val Gln Pro Arg Asp Phe Pro Glu Asp Thr Leu Arg Lys Val Ile
 65                  70                  75                  80
Gln Lys Ala Tyr Glu Ser Lys Ile Asp Tyr Asp Lys Ile Val Tyr Tyr
             85                  90                  95
Glu Ala Gly Ile Ile Leu Cys Cys Val Leu Gly Leu Leu Phe Ile Ile
            100                 105                 110
Leu Met Pro Leu Val Gly Tyr Phe Phe Cys Met Cys Arg Cys Cys Asn
            115                 120                 125
Lys Cys Gly Gly Glu Met His Gln Arg Gln Lys Glu Asn Gly Pro Phe
130                 135                 140
Leu Arg Lys Cys Phe Ala Ile Ser Leu Leu Val Ile Cys Ile Ile Ile
145                 150                 155                 160
Ser Ile Gly Ile Phe Tyr Gly Phe Val Ala Asn His Gln Val Arg Thr
                165                 170                 175
Arg Ile Lys Arg Ser Arg Lys Leu Ala Asp Ser Asn Phe Lys Asp Leu
            180                 185                 190
Arg Thr Leu Leu Asn Glu Thr Pro Glu Gln Ile Lys Tyr Ile Leu Ala
            195                 200                 205
Gln Tyr Asn Thr Thr Lys Asp Lys Ala Phe Thr Asp Leu Asn Ser Ile
            210                 215                 220
Ser Ser Val Leu Gly Gly Gly Ile Leu Asp Arg Leu Arg Pro Asn Ile
225                 230                 235                 240
Ile Pro Val Leu Asp Glu Ile Lys Ser Met Ala Thr Ala Ile Lys Glu
                245                 250                 255
Thr Lys Glu Ala Leu Glu Asn Met Asn Ser Thr Leu Lys Ser Leu His
            260                 265                 270
Gln Gln Ser Thr Gln Leu Ser Ser Ser Leu Thr Ser Val Lys Thr Ser
            275                 280                 285
Leu Arg Ser Ser Leu Asn Asp Pro Leu Cys Leu Val Arg Pro Ser Ser
290                 295                 300
Glu Thr Cys Asn Ser Ile Arg Leu Ser Leu Ser Gln Leu Asn Ser Asn
305                 310                 315                 320
Pro Glu Leu Arg Gln Leu Pro Pro Val Asp Ala Glu Leu Asp Asn Val
                325                 330                 335
Asn Asn Val Leu Arg Thr Asp Leu Asp Gly Leu Val Gln Gln Gly Tyr
            340                 345                 350
Gln Ser Leu Asn Asp Ile Pro Asp Arg Val Gln Arg Gln Thr Thr Thr
            355                 360                 365
Val Val Ala Gly Ile Lys Arg Val Leu Asn Ser Ile Gly Ser Asp Ile
370                 375                 380
Asp Asn Val Thr Gln Arg Leu Pro Ile Gln Asp Ile Leu Ser Glu Phe
385                 390                 395                 400
Ser Val Tyr Val Asn Asn Thr Glu Ser Tyr Ile His Arg Asn Leu Pro
                405                 410                 415
Thr Leu Glu Glu Tyr Asp Ser Tyr Trp Trp Leu Gly Leu Val Ile
            420                 425                 430
Cys Ser Leu Leu Thr Leu Ile Val Ile Phe Tyr Tyr Leu Gly Leu Leu
            435                 440                 445
Cys Gly Val Cys Gly Tyr Asp Arg His Ala Thr Pro Thr Thr Arg Gly
```

```
            450                 455                 460
Cys Val Ser Asn Thr Gly Gly Ile Phe Leu Met Val Gly Val Gly Leu
465                 470                 475                 480

Ser Phe Leu Phe Cys Trp Ile Leu Met Ile Ile Val Val Leu Thr Phe
                485                 490                 495

Val Phe Gly Ala Asn Val Glu Lys Leu Ile Cys Glu Pro Tyr Thr Ser
                500                 505                 510

Lys Glu Leu Phe Arg Val Leu Asp Thr Pro Tyr Leu Leu Asn Glu Asp
            515                 520                 525

Trp Glu Tyr Tyr Leu Ser Gly Lys Leu Phe Asn Lys Ser Lys Met Lys
            530                 535                 540

Leu Thr Phe Glu Gln Val Tyr Ser Asp Cys Lys Lys Asn Arg Gly Thr
545                 550                 555                 560

Tyr Gly Thr Leu His Leu Gln Asn Ser Phe Asn Ile Ser Glu Arg Leu
                565                 570                 575

Asn Ile Asn Glu His Thr Gly Ser Ile Ser Ser Glu Leu Glu Ser Leu
                580                 585                 590

Lys Val Asn Leu Asn Ile Phe Leu Leu Gly Ala Ala Gly Arg Lys Asn
            595                 600                 605

Leu Gln Asp Phe Ala Ala Cys Gly Ile Asp Arg Met Asn Tyr Asp Ser
610                 615                 620

Tyr Leu Ala Gln Thr Gly Lys Ser Pro Ala Gly Val Asn Leu Leu Ser
625                 630                 635                 640

Phe Ala Tyr Asp Leu Glu Ala Lys Ala Asn Ser Leu Pro Pro Gly Asn
                645                 650                 655

Leu Arg Asn Ser Leu Lys Arg Asp Ala Gln Thr Ile Lys Thr Ile His
                660                 665                 670

Gln Gln Arg Val Leu Pro Ile Glu Gln Ser Leu Ser Thr Leu Tyr Gln
            675                 680                 685

Ser Val Lys Ile Leu Gln Arg Thr Gly Asn Gly Leu Leu Glu Arg Val
            690                 695                 700

Thr Arg Ile Leu Ala Ser Leu Asp Phe Ala Gln Asn Phe Ile Thr Asn
705                 710                 715                 720

Asn Thr Ser Ser Val Ile Glu Glu Thr Lys Lys Tyr Gly Arg Thr
                725                 730                 735

Ile Ile Gly Tyr Phe Glu His Tyr Leu Gln Trp Ile Glu Phe Ser Ile
            740                 745                 750

Ser Glu Lys Val Ala Ser Cys Lys Pro Val Ala Thr Ala Leu Asp Thr
            755                 760                 765

Ala Val Asp Val Phe Leu Cys Ser Tyr Ile Ile Asp Pro Leu Asn Leu
770                 775                 780

Phe Trp Phe Gly Ile Gly Lys Ala Thr Val Phe Leu Leu Pro Ala Leu
785                 790                 795                 800

Ile Phe Ala Val Lys Leu Ala Lys Tyr Tyr Arg Arg Met Asp Ser Glu
                805                 810                 815

Asp Val Tyr Asp Asp Val Glu Thr Ile Pro Met Lys Asn Met Glu Asn
            820                 825                 830

Gly Asn Asn Gly Tyr His Lys Asp His Val Tyr Gly Ile His Asn Pro
            835                 840                 845

Val Met Thr Ser Pro Ser Gln His
    850                 855

<210> SEQ ID NO 3
```

```
<211> LENGTH: 865
<212> TYPE: PRT
<213> ORGANISM: Pan troglodytes

<400> SEQUENCE: 3
```

| | | | | | | | | | | | | | | | |
|---|---|---|---|---|---|---|---|---|---|---|---|---|---|---|---|
| Met | Ala | Leu | Val | Leu | Gly | Ser | Leu | Leu | Leu | Gly | Leu | Cys | Gly | Asn | |
| 1 | | | | 5 | | | | | 10 | | | | | 15 | |
| Ser | Phe | Ser | Gly | Gly | Gln | Pro | Ser | Ser | Thr | Asp | Ala | Pro | Lys | Ala | Trp |
| | | | 20 | | | | | 25 | | | | | 30 | | |
| Asn | Tyr | Glu | Leu | Pro | Ala | Thr | Asn | Tyr | Glu | Thr | Gln | Asp | Ser | His | Lys |
| | | 35 | | | | | 40 | | | | | 45 | | | |
| Ala | Gly | Pro | Ile | Gly | Ile | Leu | Phe | Glu | Leu | Val | His | Ile | Phe | Leu | Tyr |
| | 50 | | | | | 55 | | | | | 60 | | | | |
| Val | Val | Gln | Pro | Arg | Asp | Phe | Pro | Glu | Asp | Thr | Leu | Arg | Lys | Val | Ile |
| 65 | | | | | 70 | | | | | 75 | | | | | 80 |
| Gln | Lys | Ala | Tyr | Glu | Ser | Lys | Ile | Asp | Tyr | Asp | Lys | Pro | Glu | Thr | Val |
| | | | | 85 | | | | | 90 | | | | | 95 | |
| Ile | Leu | Gly | Leu | Lys | Ile | Val | Tyr | Tyr | Glu | Ala | Gly | Ile | Ile | Leu | Cys |
| | | | 100 | | | | | 105 | | | | | 110 | | |
| Cys | Val | Leu | Gly | Leu | Leu | Phe | Ile | Ile | Leu | Met | Pro | Leu | Val | Gly | Tyr |
| | | 115 | | | | | 120 | | | | | 125 | | | |
| Phe | Phe | Cys | Met | Cys | Arg | Cys | Cys | Asn | Lys | Cys | Gly | Gly | Glu | Met | His |
| | 130 | | | | | 135 | | | | | 140 | | | | |
| Gln | Arg | Gln | Lys | Glu | Asn | Gly | Pro | Phe | Leu | Arg | Lys | Cys | Phe | Ala | Ile |
| 145 | | | | | 150 | | | | | 155 | | | | | 160 |
| Ser | Leu | Leu | Val | Ile | Cys | Ile | Ile | Ile | Ser | Ile | Gly | Ile | Phe | Tyr | Gly |
| | | | | 165 | | | | | 170 | | | | | 175 | |
| Phe | Val | Ala | Asn | His | Gln | Val | Arg | Thr | Arg | Ile | Lys | Arg | Ser | Arg | Lys |
| | | | 180 | | | | | 185 | | | | | 190 | | |
| Leu | Ala | Asp | Ser | Asn | Phe | Lys | Asp | Leu | Arg | Thr | Leu | Leu | Asn | Glu | Thr |
| | | | 195 | | | | | 200 | | | | | 205 | | |
| Pro | Glu | Gln | Ile | Lys | Tyr | Ile | Leu | Ala | Gln | Tyr | Asn | Thr | Thr | Lys | Asp |
| | 210 | | | | | 215 | | | | | 220 | | | | |
| Lys | Ala | Phe | Thr | Asp | Leu | Asn | Ser | Ile | Asn | Ser | Val | Leu | Gly | Gly | Gly |
| 225 | | | | | 230 | | | | | 235 | | | | | 240 |
| Ile | Leu | Asp | Arg | Leu | Arg | Pro | Asn | Ile | Ile | Pro | Val | Leu | Asp | Glu | Ile |
| | | | | 245 | | | | | 250 | | | | | 255 | |
| Lys | Ser | Met | Ala | Thr | Ala | Ile | Lys | Glu | Thr | Lys | Glu | Ala | Leu | Glu | Asn |
| | | | 260 | | | | | 265 | | | | | 270 | | |
| Met | Asn | Ser | Thr | Leu | Lys | Ser | Leu | His | Gln | Gln | Ser | Thr | Gln | Leu | Ser |
| | | 275 | | | | | 280 | | | | | 285 | | | |
| Ser | Ser | Leu | Thr | Ser | Val | Lys | Thr | Ser | Leu | Arg | Ser | Ser | Leu | Asn | Asp |
| | 290 | | | | | 295 | | | | | 300 | | | | |
| Pro | Leu | Cys | Leu | Val | Arg | Pro | Ser | Ser | Glu | Ile | Cys | Asn | Ser | Ile | Arg |
| 305 | | | | | 310 | | | | | 315 | | | | | 320 |
| Leu | Ser | Leu | Ser | Gln | Leu | Asn | Ser | Asn | Pro | Glu | Leu | Arg | Gln | Leu | Pro |
| | | | | 325 | | | | | 330 | | | | | 335 | |
| Pro | Val | Asp | Ala | Glu | Leu | Asp | Asn | Val | Asn | Asn | Val | Leu | Arg | Thr | Asp |
| | | | 340 | | | | | 345 | | | | | 350 | | |
| Leu | Asp | Gly | Leu | Val | Gln | Gln | Gly | Tyr | Gln | Ser | Leu | Asn | Asp | Ile | Pro |
| | | 355 | | | | | 360 | | | | | 365 | | | |
| Asp | Arg | Val | Gln | Arg | Gln | Thr | Thr | Thr | Val | Val | Ala | Gly | Ile | Lys | Arg |
| | 370 | | | | | 375 | | | | | 380 | | | | |
| Val | Leu | Asn | Ser | Ile | Gly | Ser | Asp | Ile | Asp | Asn | Val | Thr | Gln | Arg | Leu |

```
            385                 390                 395                 400
        Pro Ile Gln Asp Ile Leu Ser Glu Phe Ser Val Tyr Val Asn Asn Thr
                        405                 410                 415

Glu Ser Tyr Ile His Arg Asn Leu Pro Thr Leu Glu Glu Tyr Asp Ser
                        420                 425                 430

Tyr Trp Trp Leu Gly Gly Leu Val Ile Cys Ser Leu Leu Thr Leu Ile
                        435                 440                 445

Val Ile Phe Tyr Tyr Leu Gly Leu Leu Cys Gly Val Cys Gly Tyr Asp
                        450                 455                 460

Arg His Ala Thr Pro Thr Thr Arg Gly Cys Val Ser Asn Thr Gly Gly
        465                 470                 475                 480

Val Phe Leu Met Val Gly Val Gly Leu Ser Phe Leu Phe Cys Trp Ile
                        485                 490                 495

Leu Met Ile Ile Val Val Leu Thr Phe Val Phe Gly Ala Asn Val Glu
                        500                 505                 510

Lys Leu Ile Cys Glu Pro Tyr Thr Ser Lys Glu Leu Phe Gln Val Leu
                        515                 520                 525

Asp Thr Pro Tyr Leu Leu Asn Glu Asp Trp Glu Tyr Tyr Leu Ser Gly
                        530                 535                 540

Lys Leu Phe Asn Lys Ser Lys Met Lys Leu Thr Phe Glu Gln Val Tyr
        545                 550                 555                 560

Ser Asp Cys Lys Lys Asn Arg Gly Thr Tyr Gly Thr Leu His Leu Gln
                        565                 570                 575

Asn Ser Phe Asn Ile Ser Glu Arg Leu Asn Ile Asn Glu His Thr Gly
                        580                 585                 590

Ser Ile Ser Ser Glu Leu Glu Ser Leu Lys Val Asn Leu Asn Ile Phe
                        595                 600                 605

Leu Leu Gly Ala Ala Gly Arg Lys Asn Leu Gln Asp Phe Ala Ala Cys
                        610                 615                 620

Gly Ile Asp Arg Met Asn Tyr Asp Ser Tyr Leu Ala Gln Thr Gly Lys
        625                 630                 635                 640

Ser Pro Ala Gly Val Asn Leu Leu Ser Phe Ala Tyr Asp Leu Glu Ala
                        645                 650                 655

Lys Ala Asn Ser Leu Pro Pro Gly Asn Leu Arg Asn Ser Leu Lys Arg
                        660                 665                 670

Asp Ala Gln Thr Ile Lys Thr Ile His Gln Gln Arg Val Leu Pro Ile
                        675                 680                 685

Glu Gln Ser Leu Ser Thr Leu Tyr Gln Ser Val Lys Ile Leu Gln Arg
                        690                 695                 700

Thr Gly Asn Gly Leu Leu Glu Arg Val Thr Arg Ile Leu Ala Ser Leu
        705                 710                 715                 720

Asp Phe Ala Gln Asn Phe Ile Thr Asn Thr Ser Ser Val Ile Ile
                        725                 730                 735

Glu Glu Thr Lys Lys Tyr Gly Arg Thr Ile Ile Gly Tyr Phe Glu His
                        740                 745                 750

Tyr Leu Gln Trp Ile Glu Phe Ser Ile Ser Glu Lys Val Ala Ser Cys
                        755                 760                 765

Lys Pro Val Ala Thr Ala Leu Asp Thr Ala Val Asp Val Phe Leu Cys
                        770                 775                 780

Ser Tyr Ile Ile Asp Pro Leu Asn Leu Phe Trp Phe Gly Ile Gly Lys
        785                 790                 795                 800

Ala Thr Val Phe Leu Leu Pro Ala Leu Ile Phe Ala Val Lys Leu Ala
                        805                 810                 815
```

-continued

Lys Tyr Tyr Arg Arg Met Asp Ser Glu Asp Val Tyr Asp Val Glu
                820                 825                 830

Thr Ile Pro Met Lys Asn Met Glu Asn Gly Asn Asn Gly Tyr His Lys
            835                 840                 845

Asp His Val Tyr Gly Ile His Asn Pro Val Met Thr Ser Pro Ser Gln
850                 855                 860

His
865

<210> SEQ ID NO 4
<211> LENGTH: 839
<212> TYPE: PRT
<213> ORGANISM: Canis lupus familiaris

<400> SEQUENCE: 4

Met Ala Leu Leu Leu Gly Phe Leu Leu Leu Glu Leu Cys Trp Asp
1               5                   10                  15

Thr Ser Ala Leu Gly Pro Leu Ser Ser Thr Lys Gly Ser Asp Gly Leu
            20                  25                  30

Glu Phe Glu Leu Pro Ala Thr Asn Tyr Glu Thr Lys Asp Ser Asn Gln
        35                  40                  45

Ala Gly Pro Ile Ser Val Leu Phe Gln Ile Val Gln Val Phe Leu Gln
    50                  55                  60

Val Val Gln Pro His Pro Phe Pro Glu Asp Ile Leu Arg Lys Ile Leu
65                  70                  75                  80

Gln Lys Lys Phe Asp Phe Ser Thr Asp Tyr Asp Lys Ile Ile Tyr Tyr
                85                  90                  95

Glu Ile Gly Ile Ile Ile Cys Ala Val Leu Gly Leu Leu Phe Val Ile
            100                 105                 110

Leu Met Pro Leu Val Gly Phe Cys Leu Gly Leu Cys Arg Cys Cys Asn
        115                 120                 125

Lys Cys Gly Gly Glu Met His Gln Arg Gln Lys Lys Asn Gly Ala Phe
130                 135                 140

Leu Arg Lys Tyr Phe Thr Val Ser Leu Leu Val Ile Cys Ile Phe Ile
145                 150                 155                 160

Ser Val Gly Ile Ile Tyr Gly Phe Val Ala Asn His His Leu Arg Thr
                165                 170                 175

Arg Ile Glu Lys Thr Arg Lys Leu Ala Glu Ser Asn Leu Lys Asp Leu
            180                 185                 190

Arg Thr Leu Leu Ile Gly Thr Pro Ala Gln Ile Asn Tyr Val Leu Ser
        195                 200                 205

Gln Tyr Ala Ser Thr Lys Glu Lys Ala Phe Ser Asp Leu Asp Asn Ile
    210                 215                 220

Lys Ser Leu Leu Gly Gly Gly Ile His Asp Gln Leu Arg Pro Lys Val
225                 230                 235                 240

Ile Pro Val Leu Asp Asp Ile Lys Ala Met Ala Glu Ala Ile Lys Glu
                245                 250                 255

Thr Arg Glu Ala Leu Leu Asn Val Asn Asn Thr Leu Lys Glu Leu Lys
            260                 265                 270

Met Ser Thr Ala Gln Leu Asn Thr Ser Leu Ser Asp Val Lys Arg Asn
        275                 280                 285

Leu Glu Gln Ser Leu Asn Asp Pro Met Cys Ser Val Pro Pro Val Ala
    290                 295                 300

Thr Thr Cys Asn Asn Ile Arg Met Ser Leu Gly Gln Leu Asp Asp Asn

```
            305                 310                 315                 320
        Thr Asn Leu Gly Gln Leu Pro Ser Leu Asp Lys Gln Ile Asp Asn Ile
                        325                 330                 335

Asn Asn Val Leu Gln Thr Asp Leu Ser Ser Leu Val Gln Lys Gly Tyr
                        340                 345                 350

Lys Ser Phe Asn Asp Ile Pro Glu Met Val Gln Asn Gln Thr Thr Asp
                        355                 360                 365

Ile Val Ser Asp Val Lys Arg Thr Leu Asn Ser Leu Gly Ser Asp Ile
                370                 375                 380

Glu Asn Met Ser Glu Gln Ile Pro Ile Gln Asp Lys Leu Ser Asp Phe
        385                 390                 395                 400

Ile Gly Tyr Ile Asn Asp Thr Glu Thr Tyr Ile His Arg Asn Leu Pro
                        405                 410                 415

Thr Leu Glu Glu Tyr Asp Ser Tyr Arg Trp Leu Gly Gly Leu Ile Val
                        420                 425                 430

Cys Cys Leu Leu Thr Leu Ile Val Val Phe Tyr Tyr Leu Gly Leu Met
                        435                 440                 445

Cys Gly Thr Phe Gly Tyr Asp Arg His Ala Thr Pro Thr Arg Arg Gly
                        450                 455                 460

Cys Val Ser Asn Thr Gly Gly Ile Phe Leu Met Val Gly Val Gly Ile
        465                 470                 475                 480

Ser Phe Leu Phe Cys Trp Ile Leu Met Thr Ile Val Val Leu Thr Phe
                        485                 490                 495

Val Ile Gly Gly Asn Met Glu Lys Leu Val Cys Glu Pro Tyr Gln Asn
                        500                 505                 510

Arg Lys Leu Phe Gln Ile Leu Asp Thr Pro Tyr Leu Leu Asn Glu Asn
                        515                 520                 525

Trp Lys Tyr Tyr Leu Ser Gly Met Val Leu Asn Lys Pro Asp Ile Asn
                        530                 535                 540

Leu Thr Phe Glu Gln Val Tyr Ser Asp Cys Lys Glu Asn Lys Gly Ile
        545                 550                 555                 560

Tyr Ser Thr Leu Lys Leu Glu Asn Thr Tyr Asn Ile Ser Glu His Leu
                        565                 570                 575

Asn Ile Gln Glu His Ala Arg Asn Leu Ser Asn Asp Phe Lys Asn Met
                        580                 585                 590

Asn Val Asn Ile Asp Asn Ile Val Leu Leu Asp Ala Ala Gly Arg Lys
                        595                 600                 605

Asn Leu Met Asp Phe Ser Ser Ser Gly Val Asp Thr Ile Asp Tyr Asn
                610                 615                 620

Val Tyr Leu Ala Glu Met Gly Lys Thr Pro Thr Lys Val Asn Leu Leu
        625                 630                 635                 640

Ser Phe Ala Asp Asp Leu Asp Thr Lys Ala Asn Asn Leu Pro Gln Gly
                        645                 650                 655

Ser Leu Lys Gln Ser Leu Lys Asn Asn Val Gln Asn Leu Lys Thr Ile
                        660                 665                 670

His His Gly Gln Val Met Pro Leu Glu Gln Ser Met Ser Thr Ile Asn
                        675                 680                 685

Gln Ser Ile Lys Glu Leu Gln His Lys Ser Ser Gly Leu Arg Val Lys
                        690                 695                 700

Val Ala Asn Ile Leu Ser Ser Leu Asp Ser Ala Gln Asp Phe Leu Gln
        705                 710                 715                 720

Thr Arg Ile Ser Ser Val Ile Val Lys Glu Ser Ser Lys Tyr Gly Asn
                        725                 730                 735
```

```
Met Ile Ile Gly Tyr Phe Glu His Tyr Leu Gln Trp Val Lys Ile Ser
            740                 745                 750

Ile Thr Glu Gln Ile Ala Ala Cys Lys Pro Val Ala Thr Ala Leu Asp
        755                 760                 765

Ser Ala Val Asp Val Phe Leu Cys Ser Tyr Ile Ile Asp Pro Met Asn
770                 775                 780

Leu Phe Trp Phe Gly Ile Gly Lys Ala Thr Ile Phe Leu Leu Pro Ala
785                 790                 795                 800

Ile Ile Phe Ala Val Lys Leu Ala Lys Tyr Tyr Arg Arg Met Asp Ser
                805                 810                 815

Glu Asp Val Tyr Asp Asp Met Glu Asn Gly Asn Ile Gly Phe His Arg
            820                 825                 830

His His Ser Thr Gln Thr Val
            835

<210> SEQ ID NO 5
<211> LENGTH: 842
<212> TYPE: PRT
<213> ORGANISM: Mus musculus

<400> SEQUENCE: 5

Met Ala Leu Val Phe Ser Ala Leu Leu Leu Gly Leu Cys Gly Lys
1               5                   10                  15

Ile Ser Ser Glu Gly Gln Pro Ala Phe His Asn Thr Pro Gly Ala Met
            20                  25                  30

Asn Tyr Glu Leu Pro Thr Thr Lys Tyr Glu Thr Gln Asp Thr Phe Asn
        35                  40                  45

Ala Gly Ile Val Gly Pro Leu Tyr Lys Met Val His Ile Phe Leu Asn
    50                  55                  60

Val Val Gln Pro Asn Asp Phe Pro Leu Asp Leu Ile Lys Lys Leu Ile
65                  70                  75                  80

Gln Asn Lys Asn Phe Asp Ile Ser Val Asp Ser Lys Glu Pro Glu Ile
                85                  90                  95

Ile Val Leu Ala Leu Lys Ile Ala Leu Tyr Glu Ile Gly Val Leu Ile
            100                 105                 110

Cys Ala Ile Leu Gly Leu Leu Phe Ile Ile Leu Met Pro Leu Val Gly
        115                 120                 125

Cys Phe Phe Cys Met Cys Arg Cys Cys Asn Lys Cys Gly Gly Glu Met
    130                 135                 140

His Gln Arg Gln Lys Gln Asn Ala Pro Cys Arg Arg Lys Cys Leu Gly
145                 150                 155                 160

Leu Ser Leu Leu Val Ile Cys Leu Leu Met Ser Leu Gly Ile Ile Tyr
                165                 170                 175

Gly Phe Val Ala Asn Gln Gln Thr Arg Thr Arg Ile Lys Gly Thr Gln
            180                 185                 190

Lys Leu Ala Lys Ser Asn Phe Arg Asp Phe Gln Thr Leu Leu Thr Glu
        195                 200                 205

Thr Pro Lys Gln Ile Asp Tyr Val Val Glu Gln Tyr Thr Asn Thr Lys
    210                 215                 220

Asn Lys Ala Phe Ser Asp Leu Asp Gly Ile Gly Ser Val Leu Gly Gly
225                 230                 235                 240

Arg Ile Lys Asp Gln Leu Lys Pro Lys Val Thr Pro Val Leu Glu Glu
                245                 250                 255

Ile Lys Ala Met Ala Thr Ala Ile Lys Gln Thr Lys Asp Ala Leu Gln
```

```
                260                 265                 270
Asn Met Ser Ser Ser Leu Lys Ser Leu Gln Asp Ala Ala Thr Gln Leu
            275                 280                 285
Asn Thr Asn Leu Ser Ser Val Arg Asn Ser Ile Glu Asn Ser Leu Ser
        290                 295                 300
Ser Ser Asp Cys Thr Ser Asp Pro Ala Ser Lys Ile Cys Asp Ser Ile
305                 310                 315                 320
Arg Pro Ser Leu Ser Ser Leu Gly Ser Ser Leu Asn Ser Ser Gln Leu
                325                 330                 335
Pro Ser Val Asp Arg Glu Leu Asn Thr Val Thr Glu Val Asp Lys Thr
            340                 345                 350
Asp Leu Glu Ser Leu Val Lys Arg Gly Tyr Thr Thr Ile Asp Glu Ile
        355                 360                 365
Pro Asn Thr Ile Gln Asn Gln Thr Val Asp Val Ile Lys Asp Val Lys
        370                 375                 380
Asn Thr Leu Asp Ser Ile Ser Ser Asn Ile Lys Asp Met Ser Gln Ser
385                 390                 395                 400
Ile Pro Ile Glu Asp Met Leu Leu Gln Val Ser His Tyr Leu Asn Asn
                405                 410                 415
Ser Asn Arg Tyr Leu Asn Gln Glu Leu Pro Lys Leu Glu Glu Tyr Asp
            420                 425                 430
Ser Tyr Trp Trp Leu Gly Gly Leu Ile Val Cys Phe Leu Leu Thr Leu
        435                 440                 445
Ile Val Thr Phe Phe Phe Leu Gly Leu Leu Cys Gly Val Phe Gly Tyr
        450                 455                 460
Asp Lys His Ala Thr Pro Thr Arg Arg Gly Cys Val Ser Asn Thr Gly
465                 470                 475                 480
Gly Ile Phe Leu Met Ala Gly Val Gly Phe Gly Phe Leu Phe Cys Trp
                485                 490                 495
Ile Leu Met Ile Leu Val Val Leu Thr Phe Val Val Gly Ala Asn Val
            500                 505                 510
Glu Lys Leu Leu Cys Glu Pro Tyr Glu Asn Lys Lys Leu Leu Gln Val
        515                 520                 525
Leu Asp Thr Pro Tyr Leu Leu Lys Glu Gln Trp Gln Phe Tyr Leu Ser
        530                 535                 540
Gly Met Leu Phe Asn Asn Pro Asp Ile Asn Met Thr Phe Glu Gln Val
545                 550                 555                 560
Tyr Arg Asp Cys Lys Arg Gly Arg Gly Ile Tyr Ala Ala Phe Gln Leu
                565                 570                 575
Glu Asn Val Val Asn Val Ser Asp His Phe Asn Ile Asp Gln Ile Ser
            580                 585                 590
Glu Asn Ile Asn Thr Glu Leu Glu Asn Leu Asn Val Asn Ile Asp Ser
        595                 600                 605
Ile Glu Leu Leu Asp Asn Thr Gly Arg Lys Ser Leu Glu Asp Phe Ala
        610                 615                 620
His Ser Gly Ile Asp Thr Ile Asp Tyr Ser Thr Tyr Leu Lys Glu Thr
625                 630                 635                 640
Glu Lys Ser Pro Thr Glu Val Asn Leu Leu Thr Phe Ala Ser Thr Leu
                645                 650                 655
Glu Ala Lys Ala Asn Gln Leu Pro Glu Gly Lys Leu Lys Gln Ala Phe
            660                 665                 670
Leu Leu Asp Val Gln Asn Ile Arg Ala Ile His Gln His Leu Leu Pro
        675                 680                 685
```

-continued

```
Pro Val Gln Gln Ser Leu Lys Phe Val Arg Val Arg Asn Thr Leu Arg
    690                 695                 700

Gln Ser Val Trp Thr Leu Gln Thr Ser Asn Lys Leu Pro Glu Lys
705                 710                 715                 720

Val Lys Lys Ile Leu Ala Ser Leu Asp Ser Val Gln His Phe Leu Thr
                725                 730                 735

Asn Asn Val Ser Leu Ile Val Ile Gly Glu Thr Lys Lys Phe Gly Lys
                740                 745                 750

Thr Ile Leu Gly Tyr Phe Glu His Tyr Leu His Trp Val Phe Tyr Ala
                755                 760                 765

Ile Thr Glu Lys Met Thr Ser Cys Lys Pro Met Ala Thr Ala Met Asp
    770                 775                 780

Ser Ala Val Asn Gly Ile Leu Cys Gly Tyr Val Ala Asp Pro Leu Asn
785                 790                 795                 800

Leu Phe Trp Phe Gly Ile Gly Lys Ala Thr Val Leu Leu Pro Ala
                805                 810                 815

Val Ile Ile Ala Ile Lys Leu Ala Lys Tyr Tyr Arg Arg Met Asp Ser
                820                 825                 830

Glu Asp Val Tyr Asp Asp Pro Ser Arg Tyr
                835                 840

<210> SEQ ID NO 6
<211> LENGTH: 857
<212> TYPE: PRT
<213> ORGANISM: Rattus norvegicus

<400> SEQUENCE: 6

Met Ala Leu Val Phe Ser Val Leu Leu Leu Gly Leu Cys Gly Lys
1               5                   10                  15

Met Ala Ser Gly Gly Gln Pro Ala Phe Asp Asn Thr Pro Gly Ala Leu
                20                  25                  30

Asn Tyr Glu Leu Pro Thr Thr Glu Tyr Glu Thr Gln Asp Thr Phe Asn
            35                  40                  45

Ala Gly Ile Ile Asp Pro Leu Tyr Gln Met Val His Ile Phe Leu Asn
    50                  55                  60

Val Val Gln Pro Asn Asp Phe Pro Gln Asp Leu Val Lys Lys Leu Ile
65                  70                  75                  80

Gln Lys Arg Phe Asp Ile Ser Val Asp Thr Lys Glu Val Ala Ile Tyr
                85                  90                  95

Glu Ile Gly Val Leu Ile Cys Val Ile Leu Gly Leu Leu Phe Ile Phe
                100                 105                 110

Leu Met Pro Leu Val Gly Phe Phe Cys Met Cys Arg Cys Cys Asn
                115                 120                 125

Lys Cys Gly Gly Glu Met His Gln Arg Gln Lys Gln Asn Glu Ser Cys
    130                 135                 140

Arg Arg Lys Cys Leu Ala Ile Ser Leu Leu Ile Cys Leu Leu Met
145                 150                 155                 160

Ser Leu Gly Ile Ala Phe Gly Phe Val Ala Asn Gln Gln Thr Arg Thr
                165                 170                 175

Arg Ile Gln Arg Thr Gln Lys Leu Ala Glu Ser Asn Tyr Arg Asp Leu
            180                 185                 190

Arg Ala Leu Leu Thr Glu Ala Pro Lys Gln Ile Asp Tyr Ile Leu Gly
        195                 200                 205

Gln Tyr Asn Thr Thr Lys Asn Lys Ala Phe Ser Asp Leu Asp Ser Ile
```

```
            210                 215                 220
Asp Ser Val Leu Gly Gly Arg Ile Lys Gly Gln Leu Lys Pro Lys Val
225                 230                 235                 240

Thr Pro Val Leu Glu Glu Ile Lys Ala Met Ala Thr Ala Ile Arg Gln
                245                 250                 255

Thr Lys Asp Ala Leu Gln Asn Met Ser Ser Leu Lys Ser Leu Arg
            260                 265                 270

Asp Ala Ser Thr Gln Leu Ser Thr Asn Leu Thr Ser Val Arg Asn Ser
            275                 280                 285

Ile Glu Asn Ser Leu Asn Ser Asn Asp Cys Ala Ser Asp Pro Ala Ser
            290                 295                 300

Lys Ile Cys Asp Ser Leu Arg Pro Gln Leu Ser Asn Leu Gly Ser Asn
305                 310                 315                 320

His Asn Gly Ser Gln Leu Pro Ser Val Asp Arg Glu Leu Asn Thr Val
                325                 330                 335

Asn Asp Val Asp Arg Thr Asp Leu Glu Ser Leu Val Lys Arg Gly Tyr
                340                 345                 350

Met Ser Ile Asp Glu Ile Pro Asn Met Ile Gln Asn Gln Thr Gly Asp
            355                 360                 365

Val Ile Lys Asp Val Lys Lys Thr Leu Asp Ser Val Ser Ser Lys Val
370                 375                 380

Lys Asn Met Ser Gln Ser Ile Pro Val Glu Glu Val Leu Leu Gln Phe
385                 390                 395                 400

Ser His Tyr Leu Asn Asp Ser Asn Arg Tyr Ile His Glu Ser Leu Pro
                405                 410                 415

Arg Val Glu Glu Tyr Asp Ser Tyr Trp Trp Leu Gly Gly Leu Ile Val
                420                 425                 430

Cys Phe Leu Leu Thr Leu Ile Val Thr Phe Phe Tyr Leu Gly Leu Leu
            435                 440                 445

Cys Gly Val Phe Gly Tyr Asp Lys Arg Ala Thr Pro Thr Arg Arg Gly
            450                 455                 460

Cys Val Ser Asn Thr Gly Gly Ile Phe Leu Met Ala Gly Val Gly Phe
465                 470                 475                 480

Ser Phe Leu Phe Cys Trp Ile Leu Met Ile Leu Val Val Leu Thr Phe
                485                 490                 495

Val Val Gly Ala Asn Val Glu Lys Leu Leu Cys Glu Pro Tyr Glu Asn
                500                 505                 510

Lys Lys Leu Leu Gln Val Leu Asp Thr Pro Tyr Leu Leu Asn Asp Gln
                515                 520                 525

Trp Gln Phe Tyr Leu Ser Gly Ile Leu Leu Lys Asn Pro Asp Ile Asn
            530                 535                 540

Met Thr Phe Glu Gln Val Tyr Arg Asp Cys Lys Arg Gly Arg Gly Val
545                 550                 555                 560

Tyr Ala Thr Phe Gln Leu Glu Asn Val Phe Asn Ile Thr Glu Asn Phe
                565                 570                 575

Asn Ile Glu Arg Leu Ser Glu Asp Ile Val Lys Glu Leu Glu Lys Leu
            580                 585                 590

Asn Val Asn Ile Asp Ser Ile Glu Leu Leu Asp Lys Thr Gly Arg Lys
            595                 600                 605

Ser Leu Glu Asp Phe Ala Gln Ser Gly Ile Asp Arg Ile Asn Tyr Ser
            610                 615                 620

Met Tyr Leu Gln Glu Ala Glu Lys Pro Pro Thr Lys Val Asp Leu Leu
625                 630                 635                 640
```

Thr Phe Ala Ser Phe Leu Glu Thr Glu Ala Asn Gln Leu Pro Asp Gly
                645                 650                 655

Asn Leu Lys Gln Ala Phe Leu Met Asp Ala Gln Asn Ile Arg Ala Ile
            660                 665                 670

His Gln Gln His Val Pro Val Gln Gln Ser Leu Asn Ser Leu Lys
        675                 680                 685

Gln Ser Val Trp Ala Leu Lys Gln Thr Ser Ser Lys Leu Pro Glu Glu
    690                 695                 700

Val Lys Lys Val Leu Ala Ser Leu Asp Ser Ala Gln His Phe Leu Thr
705                 710                 715                 720

Ser Asn Leu Ser Ser Ile Val Ile Gly Glu Thr Lys Lys Phe Gly Arg
                725                 730                 735

Thr Ile Ile Gly Tyr Phe Glu His Tyr Leu Gln Trp Val Leu Tyr Ala
            740                 745                 750

Ile Thr Glu Lys Met Thr Ser Cys Lys Pro Met Ile Thr Ala Met Asp
        755                 760                 765

Ser Ala Val Asn Gly Ile Leu Cys Ser Tyr Val Ala Asp Pro Leu Asn
    770                 775                 780

Leu Phe Trp Phe Gly Ile Gly Lys Ala Thr Met Leu Leu Pro Ala
785                 790                 795                 800

Val Ile Ile Ala Ile Lys Leu Ala Lys Tyr Tyr Arg Arg Met Asp Ser
                805                 810                 815

Glu Asp Val Tyr Asp Val Glu Thr Val Pro Met Lys Asn Leu Glu
            820                 825                 830

Asn Gly Ser Asn Gly Tyr His Lys Asp His Leu Tyr Gly Val His Asn
        835                 840                 845

Pro Val Met Thr Ser Pro Ser Arg Tyr
    850                 855

<210> SEQ ID NO 7
<211> LENGTH: 852
<212> TYPE: PRT
<213> ORGANISM: Homo sapiens

<400> SEQUENCE: 7

Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile

-continued

```
            145                 150                 155                 160
Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
                180                 185                 190

Leu Ala Asp Ser Asn Phe Lys Asp Leu Arg Thr Leu Asn Glu Thr
                195                 200                 205

Pro Glu Gln Ile Lys Tyr Ile Leu Ala Gln Tyr Asn Thr Thr Lys Asp
            210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
                260                 265                 270

Met Asn Ser Thr Leu Lys Ser Leu His Gln Gln Ser Thr Gln Leu Ser
                275                 280                 285

Ser Ser Leu Thr Ser Val Lys Thr Ser Leu Arg Ser Ser Leu Asn Asp
            290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
                340                 345                 350

Leu Asp Gly Leu Val Gln Gln Gly Tyr Gln Ser Leu Asn Asp Ile Pro
            355                 360                 365

Asp Arg Val Gln Arg Gln Thr Thr Thr Val Val Ala Gly Ile Lys Arg
            370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
                420                 425                 430

Tyr Trp Trp Leu Gly Gly Leu Val Ile Cys Ser Leu Leu Thr Leu Ile
                435                 440                 445

Val Ile Phe Tyr Tyr Leu Gly Leu Leu Cys Gly Val Cys Gly Tyr Asp
            450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
            530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575
```

```
Asn Ser Phe Asn Ile Ser Glu His Leu Asn Ile Asn Glu His Thr Gly
            580                 585                 590
Ser Ile Ser Ser Glu Leu Glu Ser Leu Lys Val Asn Leu Asn Ile Phe
        595                 600                 605
Leu Leu Gly Ala Ala Gly Arg Lys Asn Leu Gln Asp Phe Ala Ala Cys
    610                 615                 620
Gly Ile Asp Arg Met Asn Tyr Asp Ser Tyr Leu Ala Gln Thr Gly Lys
625                 630                 635                 640
Ser Pro Ala Gly Val Asn Leu Ser Phe Ala Tyr Asp Leu Glu Ala
            645                 650                 655
Lys Ala Asn Ser Leu Pro Pro Gly Asn Leu Arg Asn Ser Leu Lys Arg
                660                 665                 670
Asp Ala Gln Thr Ile Lys Thr Ile His Gln Gln Arg Val Leu Pro Ile
            675                 680                 685
Glu Gln Ser Leu Ser Thr Leu Tyr Gln Ser Val Lys Ile Leu Gln Arg
        690                 695                 700
Thr Gly Asn Gly Leu Leu Glu Arg Val Thr Arg Ile Leu Ala Ser Leu
705                 710                 715                 720
Asp Phe Ala Gln Asn Phe Ile Thr Asn Asn Thr Ser Ser Val Ile Ile
                725                 730                 735
Glu Glu Thr Lys Lys Tyr Gly Arg Thr Ile Ile Gly Tyr Phe Glu His
            740                 745                 750
Tyr Leu Gln Trp Ile Glu Phe Ser Ile Ser Glu Lys Val Ala Ser Cys
        755                 760                 765
Lys Pro Val Ala Thr Ala Leu Asp Thr Ala Val Asp Val Phe Leu Cys
    770                 775                 780
Ser Tyr Ile Ile Asp Pro Leu Asn Leu Phe Trp Phe Gly Ile Gly Lys
785                 790                 795                 800
Ala Thr Val Phe Leu Leu Pro Ala Leu Ile Phe Ala Val Lys Leu Ala
                805                 810                 815
Lys Tyr Tyr Arg Arg Met Asp Ser Glu Asp Val Tyr Asp Asp Ser Ser
            820                 825                 830
Trp Val Thr Ser Val Gln Val Asn Phe Phe Leu Val Leu Ile Phe
        835                 840                 845
Leu Tyr Leu Phe
    850

<210> SEQ ID NO 8
<211> LENGTH: 851
<212> TYPE: PRT
<213> ORGANISM: Canis lupus familiaris

<400> SEQUENCE: 8

Met Ala Leu Leu Leu Gly Phe Leu Leu Leu Leu Glu Leu Cys Trp Asp
1               5                   10                  15
Thr Ser Ala Leu Gly Pro Leu Ser Thr Lys Gly Ser Asp Gly Leu
            20                  25                  30
Glu Phe Glu Leu Pro Ala Thr Asn Tyr Glu Thr Lys Asp Ser Asn Gln
        35                  40                  45
Ala Gly Pro Ile Ser Val Leu Phe Gln Ile Val Gln Val Phe Leu Gln
    50                  55                  60
Val Val Gln Pro His Pro Phe Pro Glu Asp Ile Leu Arg Lys Ile Leu
65                  70                  75                  80
Gln Lys Lys Phe Asp Phe Ser Thr Asp Tyr Asp Lys Pro Glu Asn Val
```

```
                    85                  90                  95
Val Leu Thr Leu Lys Ile Ile Tyr Tyr Glu Ile Gly Ile Ile Ile Cys
                100                 105                 110

Ala Val Leu Gly Leu Leu Phe Val Ile Leu Met Pro Leu Val Gly Phe
                115                 120                 125

Cys Phe Gly Leu Cys Arg Cys Cys Asn Lys Cys Gly Gly Glu Met His
                130                 135                 140

Gln Arg Gln Lys Lys Asn Gly Ala Phe Leu Arg Lys Tyr Phe Thr Val
145                 150                 155                 160

Ser Leu Leu Val Ile Cys Ile Phe Ile Ser Val Gly Ile Ile Tyr Gly
                165                 170                 175

Phe Val Ala Asn His His Leu Arg Thr Arg Ile Glu Lys Thr Arg Lys
                180                 185                 190

Leu Ala Glu Ser Asn Leu Lys Asp Leu Arg Thr Leu Leu Ile Gly Thr
                195                 200                 205

Pro Ala Gln Ile Asn Tyr Val Leu Ser Gln Tyr Ala Ser Thr Lys Glu
                210                 215                 220

Lys Ala Phe Ser Asp Leu Asp Asn Ile Lys Ser Leu Leu Gly Gly Gly
225                 230                 235                 240

Ile His Asp Gln Leu Arg Pro Lys Val Ile Pro Val Leu Asp Asp Ile
                245                 250                 255

Lys Ala Met Ala Glu Ala Ile Lys Glu Thr Arg Glu Ala Leu Leu Asn
                260                 265                 270

Val Asn Asn Thr Leu Lys Glu Leu Lys Met Ser Thr Ala Gln Leu Asn
                275                 280                 285

Thr Ser Leu Ser Asp Val Lys Arg Asn Leu Glu Gln Ser Leu Asn Asp
                290                 295                 300

Pro Met Cys Ser Val Pro Pro Val Ala Thr Thr Cys Asn Asn Ile Arg
305                 310                 315                 320

Met Ser Leu Gly Gln Leu Asp Asp Asn Thr Asn Leu Gly Gln Leu Pro
                325                 330                 335

Ser Leu Asp Lys Gln Ile Asp Asn Ile Asn Asn Val Leu Gln Thr Asp
                340                 345                 350

Leu Ser Ser Leu Val Gln Lys Gly Tyr Lys Ser Phe Asn Asp Ile Pro
                355                 360                 365

Glu Met Val Gln Asn Gln Thr Thr Asp Ile Val Ser Ala Leu Pro Tyr
                370                 375                 380

Val Lys Arg Thr Leu Asn Ser Leu Gly Ser Asp Ile Glu Asn Met Ser
385                 390                 395                 400

Glu Gln Ile Pro Ile Gln Asp Lys Leu Ser Asp Phe Ile Gly Tyr Ile
                405                 410                 415

Asn Asp Thr Glu Thr Tyr Ile His Arg Asn Leu Pro Thr Leu Glu Glu
                420                 425                 430

Tyr Asp Ser Tyr Arg Trp Leu Gly Gly Leu Ile Val Cys Cys Leu Leu
                435                 440                 445

Thr Leu Ile Val Val Phe Tyr Tyr Leu Gly Leu Met Cys Gly Thr Phe
                450                 455                 460

Gly Tyr Asp Arg His Ala Thr Pro Thr Arg Arg Gly Cys Val Ser Asn
465                 470                 475                 480

Thr Gly Gly Ile Phe Leu Met Val Gly Val Gly Ile Ser Phe Leu Phe
                485                 490                 495

Cys Trp Ile Leu Met Thr Ile Val Val Leu Thr Phe Val Ile Gly Gly
                500                 505                 510
```

-continued

Asn Met Glu Lys Leu Val Cys Glu Pro Tyr Gln Asn Arg Lys Leu Phe
        515                 520                 525
Gln Ile Leu Asp Thr Pro Tyr Leu Leu Asn Glu Asn Trp Lys Tyr Tyr
    530                 535                 540
Leu Ser Gly Met Val Leu Asp Lys Pro Asp Ile Asn Leu Thr Phe Glu
545                 550                 555                 560
Gln Val Tyr Ser Asp Cys Lys Glu Asn Lys Gly Ile Tyr Ser Thr Leu
                565                 570                 575
Lys Leu Glu Asn Thr Tyr Asn Ile Ser Glu His Leu Asn Ile Gln Glu
            580                 585                 590
His Ala Arg Asn Leu Ser Asn Asp Phe Lys Asn Met Asn Val Asn Ile
        595                 600                 605
Asp Asn Ile Val Leu Leu Asp Ala Ala Gly Arg Lys Asn Leu Met Asp
    610                 615                 620
Phe Ser Ser Ser Gly Val Asp Thr Ile Asp Tyr Asn Val Tyr Leu Ala
625                 630                 635                 640
Glu Met Gly Lys Thr Pro Thr Lys Val Asn Leu Leu Ser Phe Ala Asp
                645                 650                 655
Asp Leu Asp Thr Lys Ala Asn Asn Leu Pro Gln Gly Ser Leu Lys Gln
            660                 665                 670
Ser Leu Lys Asn Asn Ala Gln Asn Leu Lys Thr Ile His His Gly Gln
        675                 680                 685
Val Met Pro Leu Glu Gln Ser Met Lys Tyr Gly Lys Ala Arg Ser Thr
    690                 695                 700
Ile Asn Gln Ser Ile Lys Glu Leu Gln His Lys Ser Ser Gly Leu Arg
705                 710                 715                 720
Val Lys Val Ala Asn Ile Leu Ser Ser Leu Asp Ser Ala Gln Asp Phe
                725                 730                 735
Leu Gln Thr Arg Ile Ser Ser Val Ile Val Lys Glu Ser Ser Lys Tyr
            740                 745                 750
Gly Asn Met Ile Ile Gly Tyr Phe Glu His Tyr Leu Gln Trp Val Lys
        755                 760                 765
Ile Ser Ile Thr Glu Gln Ile Ala Ala Cys Lys Pro Val Ala Thr Ala
    770                 775                 780
Leu Asp Ser Ala Val Asp Val Phe Leu Cys Ser Tyr Ile Ile Asp Pro
785                 790                 795                 800
Met Asn Leu Phe Trp Phe Gly Ile Gly Lys Ala Thr Ile Phe Leu Leu
                805                 810                 815
Pro Ala Ile Ile Phe Ala Val Lys Leu Ala Lys Tyr Tyr Arg Arg Met
            820                 825                 830
Asp Ser Glu Asp Val Tyr Asp Asp Ser Ser Val Leu Gly Thr Trp His
        835                 840                 845
Phe Thr Leu
    850

<210> SEQ ID NO 9
<211> LENGTH: 450
<212> TYPE: PRT
<213> ORGANISM: Artificial Sequence
<220> FEATURE:
<223> OTHER INFORMATION: synthetic polypolypeptide of mAb47-10 heavy
      chain

<400> SEQUENCE: 9

Met Glu Thr Gly Leu Arg Trp Leu Leu Leu Val Ala Val Leu Lys Gly

-continued

```
  1               5                   10                  15
Val Gln Cys Gln Ser Val Glu Glu Ser Gly Gly Arg Leu Val Thr Pro
             20                  25                  30
Gly Thr Pro Leu Thr Leu Thr Cys Thr Val Ser Gly Ile Asp Leu Asn
             35                  40                  45
Asn Tyr Asn Met Gln Trp Val Arg Gln Ala Pro Gly Lys Gly Leu Glu
             50                  55                  60
Trp Ile Gly Ala Thr Phe Gly Ser Asp Ser Ile Tyr Tyr Ala Thr Trp
 65                  70                  75                  80
Ala Lys Gly Arg Phe Thr Ile Ser Lys Thr Ser Thr Thr Val Asp Leu
                 85                  90                  95
Lys Met Thr Ser Leu Thr Thr Glu Asp Thr Ala Thr Tyr Phe Cys Ala
                100                 105                 110
Arg Gly Gly Leu Trp Gly Pro Gly Thr Leu Val Thr Val Ser Ser Gly
                115                 120                 125
Gln Pro Lys Ala Pro Ser Val Phe Pro Leu Ala Pro Cys Cys Gly Asp
            130                 135                 140
Thr Pro Ser Ser Thr Val Thr Leu Gly Cys Leu Val Lys Gly Tyr Leu
145                 150                 155                 160
Pro Glu Pro Val Thr Val Thr Trp Asn Ser Gly Thr Leu Thr Asn Gly
                165                 170                 175
Val Arg Thr Phe Pro Ser Val Arg Gln Ser Ser Gly Leu Tyr Ser Leu
                180                 185                 190
Ser Ser Val Val Ser Val Thr Ser Ser Ser Gln Pro Val Thr Cys Asn
                195                 200                 205
Val Ala His Pro Ala Thr Asn Thr Lys Val Asp Lys Thr Val Ala Pro
            210                 215                 220
Ser Thr Cys Ser Lys Pro Thr Cys Pro Pro Pro Glu Leu Leu Gly Gly
225                 230                 235                 240
Pro Ser Val Phe Ile Phe Pro Pro Lys Pro Lys Asp Thr Leu Met Ile
                245                 250                 255
Ser Arg Thr Pro Glu Val Thr Cys Val Val Val Asp Val Ser Gln Asp
                260                 265                 270
Asp Pro Glu Val Gln Phe Thr Trp Tyr Ile Asn Asn Glu Gln Val Arg
            275                 280                 285
Thr Ala Arg Pro Pro Leu Arg Glu Gln Gln Phe Asn Ser Thr Ile Arg
            290                 295                 300
Val Val Ser Thr Leu Pro Ile Ala His Gln Asp Trp Leu Arg Gly Lys
305                 310                 315                 320
Glu Phe Lys Cys Lys Val His Asn Lys Ala Leu Pro Ala Pro Ile Glu
                325                 330                 335
Lys Thr Ile Ser Lys Ala Arg Gly Gln Pro Leu Glu Pro Lys Val Tyr
                340                 345                 350
Thr Met Gly Pro Pro Arg Glu Glu Leu Ser Ser Arg Ser Val Ser Leu
            355                 360                 365
Thr Cys Met Ile Asn Gly Phe Tyr Pro Ser Asp Ile Ser Val Glu Trp
            370                 375                 380
Glu Lys Asn Gly Lys Ala Glu Asp Asn Tyr Lys Thr Thr Pro Ala Val
385                 390                 395                 400
Leu Asp Ser Asp Gly Ser Tyr Phe Leu Tyr Ser Lys Leu Ser Val Pro
                405                 410                 415
Thr Ser Glu Trp Gln Arg Gly Asp Val Phe Thr Cys Ser Val Met His
            420                 425                 430
```

Glu Ala Leu His Asn His Tyr Thr Gln Lys Ser Ile Ser Arg Ser Pro
        435                 440                 445

Gly Lys
    450

<210> SEQ ID NO 10
<211> LENGTH: 1342
<212> TYPE: DNA
<213> ORGANISM: Artificial Sequence
<220> FEATURE:
<223> OTHER INFORMATION: synthetic polynucleotide encoding mAb47-10
      heavy chain

<400> SEQUENCE: 10

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | caccctgac | actcacctgc | 120 |
| accgtctctg | gaatcgacct | caataactat | aacatgcaat | gggtccgcca | ggctccaggg | 180 |
| aaggggctgg | aatggatcgg | ggccactttt | ggtagtgata | gtatatacta | cgcgacctgg | 240 |
| gcgaaaggcc | gattcaccat | ctccaaaacc | tcgaccacgg | tggatctgaa | aatgaccagt | 300 |
| ctgacaaccg | aggacacggc | cacctatttc | tgtgccagag | tggtctctg | gggcccaggc | 360 |
| accctggtca | ccgtctcctc | agggcaacct | aaggctccat | cagtcttccc | actggccccc | 420 |
| tgctgcgggg | acacacccag | ctccacggtg | accctgggct | gcctggtcaa | agggtacctc | 480 |
| ccggagccag | tgaccgtgac | ctggaactcg | ggcaccctca | ccaatggggt | acgcaccttc | 540 |
| ccgtccgtcc | ggcagtcctc | aggcctctac | tcgctgagca | gcgtggtgag | cgtgacctca | 600 |
| agcagccagc | ccgtcacctg | caacgtggcc | cacccagcca | ccaacaccaa | agtggacaag | 660 |
| accgttgcgc | cctcgacatg | cagcaagccc | acgtgcccac | ccctgaact | cctgggggga | 720 |
| ccgtctgtct | tcatcttccc | cccaaaaccc | aaggacaccc | tcatgatctc | acgcaccccc | 780 |
| gaggtcacat | gcgtggtggt | ggacgtgagc | caggatgacc | ccgaggtgca | gttcacatgg | 840 |
| tacataaaca | acgagcaggt | gcgcaccgcc | cggccgccgc | tacgggagca | gcagttcaac | 900 |
| agcacgatcc | gcgtggtcag | caccctcccc | atcgcgcacc | aggactggct | gaggggcaag | 960 |
| gagttcaagt | gcaaagtcca | acaaggca | ctcccggccc | catcgagaa | aaccatctcc | 1020 |
| aaagccagag | ggcagcccct | ggagccgaag | gtctacacca | tgggccctcc | ccggaggag | 1080 |
| ctgagcagca | ggtcggtcag | cctgacctgc | atgatcaacg | gcttctaccc | ttccgacatc | 1140 |
| tcggtggagt | gggagaagaa | cgggaaggca | gaggacaact | acaagaccac | gccggccgtg | 1200 |
| ctggacagcg | acggctccta | cttcctctac | agcaagctct | cagtgcccac | gagtgagtgg | 1260 |
| cagcggggcg | acgtcttcac | ctgctccgtg | atgcacgagg | ccttgcacaa | ccactacacg | 1320 |
| cagaagtcca | tctcccgctc | tc | | | | 1342 |

<210> SEQ ID NO 11
<211> LENGTH: 239
<212> TYPE: PRT
<213> ORGANISM: Artificial Sequence
<220> FEATURE:
<223> OTHER INFORMATION: synthetic polypolypeptide of mAb47-10 light
      chain

<400> SEQUENCE: 11

Met Asp Thr Arg Ala Pro Thr Gln Leu Leu Gly Leu Leu Leu Leu Trp
1               5                   10                  15

Leu Pro Gly Val Thr Phe Ala Gln Val Leu Thr Gln Thr Ala Ser Pro

```
            20                  25                  30
Val Ser Ala Ala Val Gly Ala Thr Val Thr Ile Asn Cys Gln Ser Ser
            35                  40                  45

Gln Ser Val Tyr Asn Asn Tyr Leu Ala Trp Phe Gln Gln Lys Pro
        50                  55                  60

Gly Gln Pro Pro Lys Leu Leu Ile Tyr Arg Ala Ser Thr Leu Ala Ser
65                  70                  75                  80

Gly Val Ser Ser Arg Phe Lys Gly Ser Gly Ser Gly Thr Gln Phe Ala
                85                  90                  95

Leu Thr Ile Ser Gly Val Gln Cys Asp Asp Ala Gly Thr Tyr Tyr Cys
            100                 105                 110

Gln Gly Glu Phe Ser Cys Asp Ser Ala Asp Cys Ala Ala Phe Gly Gly
            115                 120                 125

Gly Thr Glu Val Val Lys Gly Asp Pro Val Ala Pro Thr Val Leu
        130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 12
<211> LENGTH: 717
<212> TYPE: DNA
<213> ORGANISM: Artificial Sequence
<220> FEATURE:
<223> OTHER INFORMATION: synthetic polynucleotide encoding mAb47-10
      light chain

<400> SEQUENCE: 12
atggacacga gggcccccac tcagctgctg gggctcctgc tgctctggct cccaggtgtc    60
acatttgccc aagtgctgac ccagactgca tcgcccgtgt ctgcagctgt gggcgccacc   120
gtcaccatca actgccagtc cagtcagagt gtttataata caactactt agcctggttt    180 cagcagaaac agggcagcc tcccaagctc ctgatctaca gggcatccac tctggcttct    240
ggggtctcat cgcggttcaa aggcagtgga tctgggacac agttcgctct caccatcagc    300
ggcgtgcagt gtgacgatgc tggcacttac tattgtcaag gcgaatttag ttgtgatagt    360
gctgattgtg ctgctttcgg cggagggacc gaggtggtgg tcaaaggtga tccagttgca    420
cctactgtcc tcatcttccc accagctgct gatcaggtgg caactggaac agtcaccatc    480
gtgtgtgtgg cgaataaata ctttcccgat gtcaccgtca cctgggaggt ggatggcacc    540
acccaaacaa ctggcatcga gaacagtaaa acaccgcaga attctgcaga ttgtacctac    600
aacctcagca gcactctgac actgaccagc acacagtaca acagccacaa agagtacacc    660
tgcaaggtga cccagggcac gacctcagtc gtccagagct tcaatagggg tgactgt       717

<210> SEQ ID NO 13
<211> LENGTH: 454
```

<212> TYPE: PRT
<213> ORGANISM: Artificial Sequence
<220> FEATURE:
<223> OTHER INFORMATION: synthetic polypolypeptide of mAb133-3 heavy
      chain

<400> SEQUENCE: 13

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Arg Tyr Ala Met Ser Trp Val Arg Gln Ala Pro Gly Lys Gly Leu Asp
    50                  55                  60

Trp Ile Gly Tyr Ile Asp Ile Gly Gly Ala Tyr Tyr Ala Ser Trp
65                  70                  75                  80

Ala Lys Gly Arg Phe Thr Ile Ser Glu Thr Ser Thr Thr Val Tyr Leu
                85                  90                  95

Lys Val Asn Ser Pro Thr Thr Glu Asp Thr Ala Thr Tyr Phe Cys Ala
            100                 105                 110

Arg Gly Val Ala Asn Ser Asp Ile Trp Gly Pro Gly Thr Leu Val Thr
            115                 120                 125

Val Ser Ser Gly Gln Pro Lys Ala Pro Ser Val Phe Pro Leu Ala Pro
130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
        195                 200                 205

Val Thr Cys Asn Val Ala His Pro Ala Thr Asn Thr Lys Val Asp Lys
    210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
    290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
        355                 360                 365

Ser Val Ser Leu Thr Cys Met Ile Asn Gly Phe Tyr Pro Ser Asp Ile
    370                 375                 380
```

```
Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Ser Lys
            405                 410                 415

Leu Ser Val Pro Thr Ser Glu Trp Gln Arg Gly Asp Val Phe Thr Cys
        420                 425                 430

Ser Val Met His Glu Ala Leu His Asn His Tyr Thr Gln Lys Ser Ile
    435                 440                 445

Ser Arg Ser Pro Gly Lys
    450

<210> SEQ ID NO 14
<211> LENGTH: 1362
<212> TYPE: DNA
<213> ORGANISM: Artificial Sequence
<220> FEATURE:
<223> OTHER INFORMATION: synthetic polynucleotide encoding mAb133-3
      heavy chain

<400> SEQUENCE: 14
atggagactg ggctgcgctg gcttctcctg gtcgctgtgc tcaaaggtgt ccagtgtcag      60
tcggtggagg agtccggggg tcgcctggtc acgcctggga cacccctgac actcacctgc     120
acagtctctg gattctccct cagtaggtat gcaatgagct gggtccgcca ggctccaggg     180
aagggactgg actggatcgg gtatattgat attggtggtg gcgcatacta cgcgagctgg     240
gcgaaaggtc gattcaccat ctccgagacc tcgaccacgg tgtacctgaa agtcaacagt     300
ccgacaaccg aggacacggc cacctatttc tgtgccagag gtgttgctaa tagtgacatc     360
tggggcccag gcaccctggt caccgtctcc tcagggcaac taaggctcc atcagtcttc      420 ccactggccc cctgctgcgg ggacacaccc agctccacgg tgaccctggg ctgcctggtc     480
aaagggtacc tcccggagcc agtgaccgtg acctggaact cgggcaccct caccaatggg     540
gtacgcacct tcccgtccgt ccggcagtcc tcaggcctct actcgctgag cagcgtggtg     600
agcgtgacct caagcagcca gcccgtcacc tgcaacgtgg cccacccagc caccaacacc     660
aaagtggaca gaaccgttgc gcctcgaca tgcagcaagc cacgtgccc acccctgaa        720 ctcctggggg gaccgtctgt cttcatcttc ccccaaaac ccaaggacac cctcatgatc      780
tcacgcaccc ccgaggtcac atgcgtggtg gtggacgtga gccaggatga ccccgaggtg     840
cagttcacat ggtacataaa caacgagcag gtgcgcaccg cccggccgcc gctacgggag     900
cagcagttca cagcacgat ccgcgtggtc agcaccctcc ccatcgcgca ccaggactgg      960
ctgaggggca aggagttcaa gtgcaaagtc acaacaagg cactcccggc ccccatcgag     1020 aaaccatct ccaaagccag agggcagccc ctggagccga aggtctacac catgggccct      1080
ccccgggagg agctgagcag caggtcggtc agcctgacct gcatgatcaa cggcttctac     1140
ccttccgaca tctcggtgga gtgggagaag aacgggaagg cagaggacaa ctacaagacc     1200
acgccggccg tgctggacag cgacggctcc tacttcctct acagcaagct ctcagtgccc     1260
acgagtgagt ggcagcgggg cgacgtcttc acctgctccg tgatgcacga ggccttgcac     1320
aaccactaca cgcagaagtc catctcccgc tctccgggta aa                        1362

<210> SEQ ID NO 15
<211> LENGTH: 238
<212> TYPE: PRT
<213> ORGANISM: Artificial Sequence
<220> FEATURE:
```

<223> OTHER INFORMATION: synthetic polypolypeptide of mAb133-3 light
      chain

<400> SEQUENCE: 15

Met Asp Thr Arg Ala Pro Thr Gln Leu Leu Gly Leu Leu Leu Trp
1               5                   10                  15

Leu Pro Gly Ala Arg Cys Ala Leu Val Met Thr Gln Thr Pro Ser Pro
                20                  25                  30

Val Ser Ala Ala Val Gly Gly Thr Val Thr Ile Asn Cys Gln Ser Ser
            35                  40                  45

Gln Ser Val Phe Asn Asn Lys Trp Leu Ser Trp Tyr Gln Gln Lys Pro
        50                  55                  60

Gly Gln Pro Pro Lys Leu Leu Ile Tyr Phe Val Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Ser Asp Tyr Ser Ser Gly Trp Tyr Ser Pro Phe Gly Gly Gly
        115                 120                 125

Thr Glu Val Val Val Glu Gly Asp Pro Val Ala Pro Thr Val Leu Ile
    130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 16
<211> LENGTH: 714
<212> TYPE: DNA
<213> ORGANISM: Artificial Sequence
<220> FEATURE:
<223> OTHER INFORMATION: synthetic polynucleotide encoding mAb133-3
      light chain

<400> SEQUENCE: 16
atggacacga gggcccccac tcagctgctg gggctcctgc tgctctggct cccaggtgcc      60
agatgtgccc ttgtgatgac ccagactcca tccccgtgt ctgcagctgt gggaggcaca     120
gtcaccatca attgccagtc cagtcagagt gttttaata taaatggtt atcctggtat      180 cagcagaaac agggcagcc tcccaagctc ctgatctatt ttgtatccac tctggcatct     240
ggggtcccat cgcggttcaa aggcagtgga tctgggacac agttcactct caccatcagc     300
ggcgtgcagt gtgacgatgc tgccacttac tactgtcaag cagtgatta tagtagtggt     360 tggtatagtc ctttcggcgg agggaccgag gtggtggtcg aaggtgatcc agttgcacct     420
actgtcctca tcttcccacc agctgctgat caggtggcaa ctggaacagt caccatcgtg     480
tgtgtggcga ataaatactt tcccgatgtc accgtcacct gggaggtgga tggcaccacc     540

```
caaacaactg gcatcgagaa cagtaaaaca ccgcagaatt ctgcagattg tacctacaac    600
ctcagcagca ctctgacact gaccagcaca cagtacaaca gccacaaaga gtacacctgc    660
aaggtgaccc agggcacgac ctcagtcgtc cagagcttca ataggggtga ctgt          714
```

```
<210> SEQ ID NO 17
<211> LENGTH: 35
<212> TYPE: PRT
<213> ORGANISM: Artificial Sequence
<220> FEATURE:
<223> OTHER INFORMATION: synthetic domain A immunogenic polypeptide

<400> SEQUENCE: 17

Lys Thr Ser Leu Arg Ser Ser Leu Asn Asp Pro Leu Cys Leu Val His
1               5                   10                  15

Pro Ser Ser Glu Thr Cys Asn Ser Ile Arg Leu Ser Leu Ser Gln Leu
            20                  25                  30

Asn Ser Asn
        35

<210> SEQ ID NO 18
<211> LENGTH: 30
<212> TYPE: PRT
<213> ORGANISM: Artificial Sequence
<220> FEATURE:
<223> OTHER INFORMATION: synthetic CD133 domain B immunogenic
      polypeptide

<400> SEQUENCE: 18

Arg Lys Asn Leu Gln Asp Phe Ala Ala Cys Gly Ile Asp Arg Met Asn
1               5                   10                  15

Tyr Asp Ser Tyr Leu Ala Gln Thr Gly Lys Ser Pro Ala Lys
            20                  25                  30

<210> SEQ ID NO 19
<211> LENGTH: 245
<212> TYPE: PRT
<213> ORGANISM: Artificial Sequence
<220> FEATURE:
<223> OTHER INFORMATION: synthetic recombinant CD133 domain A
      immunogenic polypeptide

<400> SEQUENCE: 19

Met His His His His His His Ser Ser Gly Val Asp Leu Gly Thr Glu
1               5                   10                  15

Asn Leu Tyr Phe Gln Ser Asn Ala Asn His Gln Val Arg Thr Arg Ile
            20                  25                  30

Lys Arg Ser Arg Lys Leu Ala Asp Ser Asn Phe Lys Asp Leu Arg Thr
        35                  40                  45

Leu Leu Asn Glu Thr Pro Glu Gln Ile Lys Tyr Ile Leu Ala Gln Tyr
    50                  55                  60

Asn Thr Thr Lys Asp Lys Ala Phe Thr Asp Leu Asn Ser Ile Asn Ser
65                  70                  75                  80

Val Leu Gly Gly Gly Ile Leu Asp Arg Leu Arg Pro Asn Ile Ile Pro
                85                  90                  95

Val Leu Asp Glu Ile Lys Ser Met Ala Thr Ala Ile Lys Glu Thr Lys
            100                 105                 110

Glu Ala Leu Glu Asn Met Asn Ser Thr Leu Lys Ser Leu His Gln Gln
        115                 120                 125

Ser Thr Gln Leu Ser Ser Ser Leu Thr Ser Val Lys Thr Ser Leu Arg
    130                 135                 140
```

```
Ser Ser Leu Asn Asp Pro Leu Cys Leu Val His Pro Ser Ser Glu Thr
145                 150                 155                 160

Cys Asn Ser Ile Arg Leu Ser Leu Ser Gln Leu Asn Ser Asn Pro Glu
                165                 170                 175

Leu Arg Gln Leu Pro Pro Val Asp Ala Glu Leu Asp Asn Val Asn Asn
            180                 185                 190

Val Leu Arg Thr Asp Leu Asp Gly Leu Val Gln Gln Gly Tyr Gln Ser
        195                 200                 205

Leu Asn Asp Ile Pro Asp Arg Val Gln Arg Gln Thr Thr Thr Val Val
    210                 215                 220

Ala Gly Ile Lys Arg Val Leu Asn Ser Ile Gly Ser Asp Ile Asp Asn
225                 230                 235                 240

Val Thr Gln Arg Leu
                245

<210> SEQ ID NO 20
<211> LENGTH: 255
<212> TYPE: PRT
<213> ORGANISM: Artificial Sequence
<220> FEATURE:
<223> OTHER INFORMATION: synthetic recombinant CD133 domain B
      immunogenic polypeptide

<400> SEQUENCE: 20

Met His His His His His Ser Ser Gly Val Asp Leu Gly Thr Glu
1               5                   10                  15

Asn Leu Tyr Phe Gln Ser Asn Ala Ile Cys Glu Pro Tyr Thr Ser Lys
                20                  25                  30

Glu Leu Phe Arg Val Leu Asp Thr Pro Tyr Leu Leu Asn Glu Asp Trp
            35                  40                  45

Glu Tyr Tyr Leu Ser Gly Lys Leu Phe Asn Lys Ser Lys Met Lys Leu
        50                  55                  60

Thr Phe Glu Gln Val Tyr Ser Asp Cys Lys Lys Asn Arg Gly Thr Tyr
65                  70                  75                  80

Gly Thr Leu His Leu Gln Asn Ser Phe Asn Ile Ser Glu His Leu Asn
                85                  90                  95

Ile Asn Glu His Thr Gly Ser Ile Ser Ser Glu Leu Glu Ser Leu Lys
                100                 105                 110

Val Asn Leu Asn Ile Phe Leu Leu Gly Ala Ala Gly Arg Lys Asn Leu
            115                 120                 125

Gln Asp Phe Ala Ala Cys Gly Ile Asp Arg Met Asn Tyr Asp Ser Tyr
        130                 135                 140

Leu Ala Gln Thr Gly Lys Ser Pro Ala Gly Val Asn Leu Leu Ser Phe
145                 150                 155                 160

Ala Tyr Asp Leu Glu Ala Lys Ala Asn Ser Leu Pro Pro Gly Asn Leu
                165                 170                 175

Arg Asn Ser Leu Lys Arg Asp Ala Gln Thr Ile Lys Thr Ile His Gln
            180                 185                 190

Gln Arg Val Leu Pro Ile Glu Gln Ser Leu Ser Thr Leu Tyr Gln Ser
        195                 200                 205
```

-continued

```
Val Lys Ile Leu Gln Arg Thr Gly Asn Gly Leu Leu Glu Arg Val Thr
    210                 215                 220

Arg Ile Leu Ala Ser Leu Asp Phe Ala Gln Asn Phe Ile Thr Asn Asn
225                 230                 235                 240

Thr Ser Ser Val Ile Ile Glu Glu Thr Lys Lys Tyr Gly Arg Thr
                245                 250                 255
```